United States Patent
Jackson et al.

(10) Patent No.: US 6,452,044 B2
(45) Date of Patent: Sep. 17, 2002

(54) BENZENEDICARBOXYLIC ACID DERIVATIVES

(75) Inventors: Paul F. Jackson, White House Station, NJ (US); Takashi Tsukamoto, Ellicott City, MD (US); Barbara S. Slusher, Kingsville, MD (US); Eric Wang, Ellicott City, MD (US)

(73) Assignee: Guilford Pharmaceuticals Inc., Baltimore, MD (US)

( * ) Notice: Subject to any disclaimer, the term of this patent is extended or adjusted under 35 U.S.C. 154(b) by 0 days.

(21) Appl. No.: 09/866,758

(22) Filed: May 30, 2001

Related U.S. Application Data

(60) Provisional application No. 60/207,402, filed on May 30, 2000.

(51) Int. Cl.$^7$ ............... C07C 321/10; A61K 31/095
(52) U.S. Cl. ............... 562/432; 514/706; 562/405; 562/434; 562/435
(58) Field of Search ............... 562/432, 405, 562/434, 435; 514/706

(56) References Cited

U.S. PATENT DOCUMENTS

| | | | |
|---|---|---|---|
| 3,898,266 A | * | 8/1975 | Feit et al. ............... 260/465 |
| 3,950,380 A | * | 4/1976 | Feit et al. ............... 260/465 |
| 4,250,182 A | | 2/1981 | Gorvin |
| 4,863,636 A | | 9/1989 | Chang et al. |
| 5,498,784 A | | 3/1996 | Arnold et al. |
| 5,672,592 A | | 9/1997 | Jackson et al. |
| 5,795,877 A | | 8/1998 | Jackson et al. |
| 5,804,602 A | | 9/1998 | Slusher et al. |
| 5,807,688 A | | 9/1998 | Blackburn et al. |
| 5,824,662 A | | 10/1998 | Slusher et al. |
| 5,863,536 A | | 1/1999 | Jackson et al. |
| 5,880,112 A | | 3/1999 | Jackson et al. |
| 5,880,309 A | | 3/1999 | Suzuki et al. |
| 5,902,817 A | | 5/1999 | Jackson et al. |
| 5,962,521 A | | 10/1999 | Jackson et al. |
| 5,968,915 A | | 10/1999 | Jackson et al. |

(List continued on next page.)

FOREIGN PATENT DOCUMENTS

| | | |
|---|---|---|
| CL | 651-91 | 2/1998 |
| EP | 0745673 | 12/1996 |
| JP | 2-204754 | 8/1990 |
| JP | 2-208666 | 8/1990 |
| JP | 11-269182 | 10/1999 |
| JP | 2000-95788 | 4/2000 |
| JP | 2000-159984 | 6/2000 |
| NL | 6606892 | 7/1967 |

OTHER PUBLICATIONS

C.A. 66:3730 (Abstract of NL 6606892).
C.A. 79:147536 (Abstract of M. Erickson et al., Acta Chem. Scand. (1973), 27(5), 1673–8).

(List continued on next page.)

*Primary Examiner*—Floyd D. Higel
*Assistant Examiner*—Golam M. M. Shameem
(74) *Attorney, Agent, or Firm*—Lyon & Lyon LLP

(57) ABSTRACT

New benzenedicarboxylic acid derivative compounds; pharmaceutical compositions, diagnostic methods, and diagnstic kits that include those compounds; and methods of using those compounds for inhibiting NAALADase enzyme activity, detecting diseases where NAALADase levels are altered, effecting neuronal activity, effecting TGF-β activity, inhibiting angiogenesis, and treating glutamate abnormalities, neutopathy, pain, compulsive disorders, prostate diseases, cancers, and glaucoma.

38 Claims, 18 Drawing Sheets

TGF-β1 in Cell Cultures Treated with Compound C During 20 minute Ischemia

U.S. PATENT DOCUMENTS

| | | |
|---|---|---|
| 5,977,090 A | 11/1999 | Slusher et al. |
| 5,981,209 A | 11/1999 | Slusher et al. |
| 5,985,855 A | 11/1999 | Slusher et al. |
| 6,004,946 A | 12/1999 | Slusher et al. |
| 6,011,021 A | 1/2000 | Slusher et al. |
| 6,017,903 A | 1/2000 | Slusher et al. |
| 6,025,344 A | 2/2000 | Jackson et al. |
| 6,025,345 A | 2/2000 | Jackson et al. |
| 6,028,216 A | 2/2000 | Morales et al. |
| 6,046,180 A | 4/2000 | Jackson et al. |
| 6,054,444 A | 4/2000 | Jackson et al. |
| 6,071,965 A | 6/2000 | Jackson et al. |
| 6,121,252 A | 9/2000 | Jackson et al. |
| 6,228,888 B1 | 5/2001 | Slusher |

OTHER PUBLICATIONS

C.A. 85:177080 (Abstract of V. Kudlacek et al., CS 162594).

C.A. 94:214626 (Abstract of US 4250182).

C.A. 105:190584 (Abstract of A. El–Maghraby et al., Egypt. J. Pharm. Sci. (1985), vol. Date 1983, 24(1–4).

C.A. 124:219572 (Abstract of P. Wentworth et al., Proc. Natl. Acad. Sci. USA (1996), 93(2), 799–803).

C.A. 126:70131 (Abstract of EP 0745673).

C.A. 129:81601 (Abstract of M. Pickert et al., Arch. Pharm. (1998), 331(5), 177–192).

Watson, S., et al., "TiPS Receptor and Ion Channel Nomenclature Supplement 1995," pp. 1 and 30–32, *Elsevier Trends Journals*, $6^{th}$ Ed., United Kingdom (ISBN 1357–485X).

Wentworth, et al., "Antibody Catalysis of BAC2 Aryl Carbamate Ester Hydrolysis: A Highly Disfavored Chemical Process," *Journal of the American Chemical Society*, 1997, vol. 119, No. 9, pp. 2315–2316.

Wentworth, et al., "Toward antibody–directed 'abzyme' prodrug therapy, ADAPT: Carbamate prodrug activation by a catalytic antibody and its in vitro application to human tumor cell killing," Proceedings of the National Academy of Sciences of the United States of America, 1996, vol. 93, No. 2, pp. 799–803.

WPINDEX Abstract for JP–2–204754.
WPINDEX Abstract for JP–2–208666.
WPINDEX Abstract for JP–11–269182.
WPINDEX Abstract for JP–2000–95788.
WPINDEX Abstract for JP–2000–159984.

* cited by examiner

BENZENEDICARBOXYLIC ACID DERIVATIVES

This application claims the benefit of U.S. Provisional Application No. 60/207,402, filed May 30, 2000.

The present invention relates to new compounds, pharmaceutical compositions comprising such compounds, and methods of using such compounds to inhibit NAALADase enzyme activity, detecting diseases where NAALADase levels are altered, inhibit angiogenesis, effect neuronal activity, and treat glutamate abnormalities, neuropathy, pain, prostate diseases, cancers, TGF-β abnormalities, compulsive disorders, and glaucoma.

The NAALADase enzyme, also known as prostate specific membrane antigen ("PSM" or "PSMA") and human glutamate carboxypeptidase II ("GCP II"), catalyzes the hydrolysis of the neuropeptide N-acetyl-aspartyl-glutamate ("NAAG") to N-acetyl-aspartate ("NAA") and glutamate. Based upon amino acid sequence homology, NAALADase has been assigned to the M28 family of peptidases.

Studies suggest NAALADase inhibitors may be effective in treating ischemia, spinal cord injury, demyelinating diseases, Parkinson's disease, Amyotrophic Lateral Sclerosis ("ALS"), alcohol dependence, nicotine dependence, cocaine dependence, cancer, diabetic neuropathy, pain and schizophrenia, and in inhibiting angiogenesis. In view of their broad range of potential applications, a need exists for new NAALADase inhibitors and pharmaceutical compositions comprising such compounds.

SUMMARY OF THE INVENTION

Specifically, the present invention relates to a compound of formula I

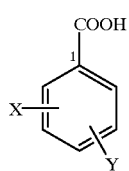

I or a pharmaceutically acceptable equivalent, wherein:
X is —W—Z;
W is a bond or a linking group;
Z is a terminal group; and
Y is —COOH oriented meta or para relative to C-1.

Additionally, the present invention relates to a method for inhibiting NAALADase enzyme activity, treating a glutamate abnormality, effecting a neuronal activity (e.g., treating peripheral neuropathy or neuropathic pain), treating a prostate disease, treating cancer, inhibiting angiogenesis, or effecting a TGF-β activity, comprising administering to a mammal in need of such inhibition, treatment, or effect, an effective amount of a compound of formula I, as described above.

The present invention further relates to method for detecting a disease, disorder, or condition where NAALADase levels are altered, comprising:
(i) contacting a sample of bodily tissue or fluid with a compound of formula I, as defined above, wherein said compound binds to any NAALADase in said sample; and
(ii) measuring the amount of any NAALADase bound to said sample, wherein the amount of NAALADase is diagnostic for said disease, disorder or condition.

The present invention further relates to a method for detecting a disease, disorder or condition where NAALADase levels are altered in an animal or a mammal, comprising:
(i) labeling a compound of formula I, as defined above, with an imaging reagent;
(ii) administering to said animal or mammal an effective amount of the labeled compound;
(iii) allowing said labeled compound to localize and bind to NAALADase present in said animal or mammal; and
(iv) measuring the amount of NAALADase bound to said labeled compound, wherein the amount of NAALADase is diagnostic for said disease, disorder or condition.

The present invention further relates to a diagnostic kit for detecting a disease, disorder or condition where NAALADase levels are altered, comprising a compound of formula I, as defined above, labeled with a marker.

The invention further relates to a pharmaceutical composition comprising:
(i) an effective amount of a compound of formula I or a pharmaceutically acceptable equivalent; and
(ii) a pharmaceutically acceptable carrier.

DETAILED DESCRIPTION

Definitions

Figure 1:
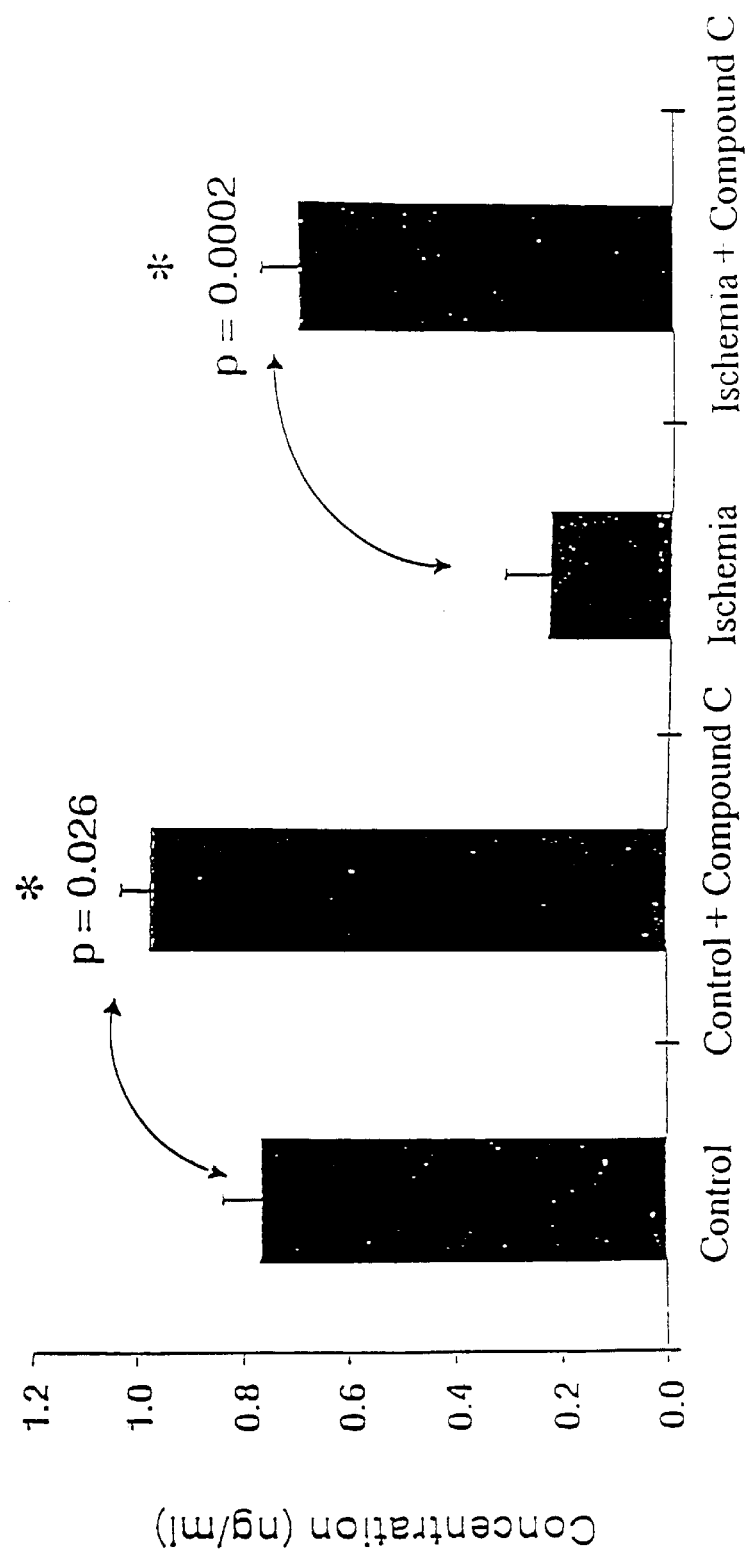
FIG. 1 is a bar graph showing the effect of Compound C on TGF-β1 concentrations in ischemic cell cultures.

"Compound A" refers to 2-[[(2,3,4,5,6-pentafluorobenzyl)hydroxyphosphinyl]methyl]pentanedioic acid.

"Compound B" refers to 2-(3-sulfanylpropyl)pentanedioic acid.

"Compound C" refers to 2-(phosphonomethyl)pentanedioic acid ("PMPA").

"Compound D" refers to 2-(2-sulfanylethyl)pentanedioic acid.

"Alkyl" refers to a branched or unbranched saturated hydrocarbon chain comprising a designated number of carbon atoms. For example, $C_1$–$C_9$ alkyl is a straight or branched hydrocarbon chain containing 1 to 9 carbon atoms, and includes but is not limited to substituents such as methyl, ethyl, propyl, iso-propyl, butyl, iso-butyl, tert-butyl, n-pentyl, n-hexyl, and the like, unless otherwise indicated.

"Alkenyl" refers to a branched or unbranched unsaturated hydrocarbon chain comprising a designated number of carbon atoms. For example, $C_2$–$C_9$ alkenyl is a straight or branched hydrocarbon chain containing 2 to 9 carbon atoms having at least one double bond, and includes but is not limited to substituents such as ethenyl, propenyl, iso-propenyl, butenyl, iso-butenyl, tert-butenyl, n-pentenyl, n-hexenyl, and the like, unless otherwise indicated.

"Alkoxy" refers to the group —OR wherein R is alkyl as herein defined. Preferably, R is a branched or unbranched saturated hydrocarbon chain containing 1 to 9 carbon atoms.

"Carbocycle" refers to a hydrocarbon, cyclic moiety having one or more closed ring(s) that is/are alicyclic, aromatic, fused and/or bridged. Examples include cyclopropane, cyclobutane, cyclopentane, cyclohexane, cycloheptane, cyclopentene, cyclohexene, cycloheptene, cyclooctene, benzyl, naphthene, anthracene, phenanthracene, biphenyl and pyrene.

"Aryl" refers to an aromatic, hydrocarbon cyclic moiety having one or more closed rings. Examples include, without limitation, phenyl, benzyl, naphthyl, anthracenyl, phenanthracenyl, biphenyl, furanyl, and pyrenyl.

"Heterocycle" refers to a cyclic moiety having one or more closed rings that is/are alicyclic, aromatic, fused and/or bridged, with one or more heteroatoms (for example, sulfur, nitrogen or oxygen) in at least one of the rings. Examples include, without limitation, pyrrolidine, pyrrole, thiazole, thiophene, piperidine, pyridine, isoxazolidine and isoxazole.

"Heteroaryl" refers to an aromatic, cyclic moiety having one or more closed rings with one or more heteroatoms (for example, sulfur, nitrogen or oxygen) in at least one of the rings. Examples include, without limitation, pyrrole, thiophene, pyridine and isoxazole.

"Linking group" refers to a moiety that connects the metal binding group with the benzene ring in the compound of formula I, without compromising the pharmacological or biological activity of the overall compound.

"Metal binding group" refers to a functional group capable of interacting with metal ion(s), such as $Co^{2+}$, $Ni^{2+}$, $Mn^{2+}$, $Cu^{2+}$, $Zn^{2+}$, $Mg^{2+}$, $Fe^{2+}$, $Fe^{3+}$ or $Al^{3+}$. Metal binding groups include without limitation amines (e.g., ethylenediamine), aldehydes, ketones, carboxylic acids (e.g., ethylenediaminetetraacetic acid ("EDTA")), thiols, phosphorus derivatives and hydroxamic acids.

"Derivative" refers to a substance produced from another substance either directly or by modification or partial substitution.

"Effective amount" refers to the amount required to inhibit NAALADase enzyme activity, treat a glutamate abnormality, effect a neuronal activity, treat diabetic neuropathy, pain, prostate disease, and cancer, inhibit angiogenesis, and treat a TGF-β abnormality, a compulsive disorder, and glaucoma.

"Electromagnetic radiation" includes without limitation radiation having a wavelength of $10^{-20}$ to $10^0$ m. Examples include, without limitation, gamma radiation ($10^{-20}$ to $10^{-13}$ m), x-ray radiation ($10^{-11}$ to $10^{-9}$ m), ultraviolet light (10 nm to 400 nm), visible light (400 nm to 700 nm), infrared radiation (700 nm to 1.0 mm) and microwave radiation (1 mm to 30 cm).

"Halo" refers to at least one fluoro, chloro, bromo, or iodo moiety.

"Isosteres" refer to elements, functional groups, substitutents, molecules or ions having different molecular formulae but exhibiting similar or identical physical properties. For example, tetrazole is an isostere of carboxylic acid because it mimics the properties of carboxylic acid even though they have different molecular formulae. Typically, two isosteric molecules have similar or identical volumes and shapes. Ideally, isosteric compounds should be isomorphic and able to co-crystallize. Other physical properties that isosteric compounds usually share include boiling point, density, viscosity and thermal conductivity. However, certain properties may be different: dipolar moments, polarity, polarization, size and shape since the external orbitals may be hybridized differently. The term "isosteres" encompass "bioisosteres."

"Bioisosteres" are isosteres that, in addition to their physical similarities, share some common biological properties. Typically, bioisosteres interact with the same recognition site or produce broadly similar biological effects.

"Carboxylic acid isosteres" include without limitation direct derivatives such as hydroxamic acids, acylcyanamides and acylsulfonamides; planar acidic heterocycles such as tetrazoles, mercaptoazoles, sulfinylazoles, sulfonylazoles, isoxazoles; isothiazoles, hydroxythiadiazoles and hydroxychromes; and non-planar sulfur- or phosphorus-derived acidic functions such as phosphinates, phosphonates, phosphonamides, sulphonates, sulphonamides, and acylsulphonamides.

"Metabolite" refers to a substance produced by metabolism or by a metabolic process.

"NAAG" refers to N-acetyl-aspartyl-glutamate, an important peptide component of the brain, with levels comparable to the major inhibitor neurotransmitter gamma-aminobutyric acid ("GABA"). NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate. In addition, NAAG is an agonist at group II metabotropic glutamate receptors, specifically $mGluR_3$ receptors; when attached to a moiety capable of inhibiting NAALADase, it is expected that metabotropic glutamate receptor ligands will provide potent and specific NAALADase inhibitors.

"NAALADase" refers to N-acetylated a-linked acidic dipeptidase, a membrane bound metallopeptidase which catabolizes NAAG to N-acetylaspartate ("NAA") and glutamate ("GLU"):

Catabolism of NAAG by NAALADase

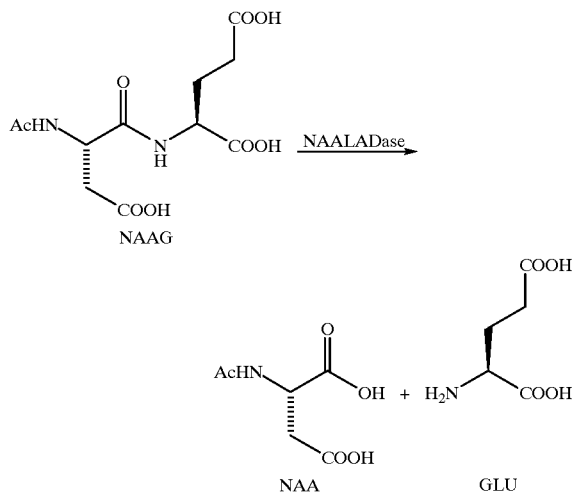

NAALADase has been assigned to the M28 peptidase family and is also called PSM, PSMA, or GCP II, EC number 3.4.17.21. It is believed that NAALADase is a co-catalytic zinc/zinc metallopeptidase. NAALADase shows a high affinity for NAAG with a Km of 540 nM. If NAAG is a bioactive peptide, then NAALADase may serve to inactivate NAAG's synaptic action. Alternatively, if NAAG functions as a precursor for glutamate, the primary function of NAALADase may be to regulate synaptic glutamate availability.

"Pharmaceutically acceptable carrier" refers to any carrier, diluent, excipient, wetting agent, buffering agent, suspending agent, lubricating agent, adjuvant, vehicle, delivery system, emulsifier, disintegrant, absorbent, preservative, surfactant, colorant, flavorant, or sweetener, preferably non-toxic, that would be suitable for use in a pharmaceutical composition.

"Pharmaceutically acceptable equivalent" includes, without limitation, pharmaceutically acceptable salts, hydrates, metabolites, prodrugs and isosteres. Many pharmaceutically acceptable equivalents are expected to have the same or similar in vitro or in vivo activity as the compounds of the invention.

"Pharmaceutically acceptable salt" refers to a salt of the inventive compounds which possesses the desired pharmacological activity and which is neither biologically nor otherwise undesirable. The salt can be formed with acids that include, without limitation, acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. The basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Prodrug" refers to a derivative of the inventive compounds that undergoes biotransformation, such as metabolism, before exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by *Burger's Medicinal Chemistry and Drug Chemistry*, Fifth Ed., Vol. 1, pp. 172–178, 949–982 (1995).

"Radiosensitizer" refers to a low molecular weight compound administered to animals in therapeutically effective amounts to promote the treatment of diseases that are treatable with electromagnetic radiation. Diseases that are treatable with electromagnetic radiation include, without limitation, neoplastic diseases, benign and malignant tumors, and cancerous cells. Electromagnetic radiation treatment of other diseases not listed herein are also contemplated by the present invention.

"Inhibition," in the context of enzymes, refers to reversible enzyme inhibition such as competitive, uncompetitive, and non-competitive inhibition. Competitive, uncompetitive, and non-competitive inhibition can be distinguished by the effects of an inhibitor on the reaction kinetics of an enzyme. Competitive inhibition occurs when the inhibitor combines reversibly with the enzyme in such a way that it competes with a normal substrate for binding at the active site. The affinity between the inhibitor and the enzyme may be measured by the inhibitor constant, $K_i$, which is defined as:

$$K_i = \frac{[E][I]}{[EI]}$$

wherein [E] is the concentration of the enzyme, [I] is the concentration of the inhibitor, and [EI] is the concentration of the enzyme-inhibitor complex formed by the reaction of the enzyme with the inhibitor. Unless otherwise specified, $K_i$ as used herein refers to the affinity between the inventive compounds and NAALADase.

"$IC_{50}$" is a related term used to define the concentration or amount of a compound that is required to cause a 50% inhibition of the target enzyme.

"NAALADase inhibitor" refers to any compound that inhibits NAALADase enzyme activity. Preferably, a NAALADase inhibitor exhibits a $K_i$ of less than 100 µM, more preferably less than 10 µM, and even more preferably less than 1 µM, as determined using any appropriate assay known in the art.

"Isomers" refer to compounds having the same number and kind of atoms, and hence the same molecular weight, but differing with respect to the arrangement or configuration of the atoms.

"Stereoisomers" are isomers that differ only in the arrangement of the atoms in space.

"Optical isomers" refer to diastereoisomers or enantiomers.

"Diastereoisomers" are stereoisomers that are not mirror images of each other. Diastereoisomers occur in compounds having two or more asymmetric carbon atoms; thus, such compounds have $2^n$ optical isomers, where n is the number of asymmetric carbon atoms.

"Enantiomers" are a pair of stereoisomers that are non-superimposable mirror images of each other. Enantiomers result from the presence of one or more asymmetric carbon atoms in the compound (e.g. glyceraldehyde, lactic acid, sugars, tartaric acid, amino acids).

"Enantiomer-enriched" refers to a mixture in which one enantiomer predominates.

"Racemic mixture" means a mixture containing equal amounts of individual enantiomers.

"Non-racemic" mixture containing unequal amounts of enantiomers.

"Angiogenesis" refers to the process whereby new capillaries are formed. "Inhibition" of angiogenesis may be measured by many parameters in accordance with the present invention and, for instance, may be assessed by delayed appearance of neovascular structures, slowed development of neovascular structures, decreased occurrence of neovascular structures, slowed or decreased severity of angiogenesis dependent disease effects, arrested angiogenic growth, or regression of previous angiogenic growth. In the extreme, complete inhibition is referred to herein as prevention. In relation to angiogenesis or angiogenic growth, "prevention" refers ti ni substantial angiogenesis or angiogenic growth if none had previously occurred, or no substantial further angiogenesis or angiogenic growth if growth had previously occurred.

"Angiogenesis-dependent disease" includes, without limitation, rheumatoid arthritis, cardiovascular diseases, neovascular diseases of the eye, peripheral vascular disorders, dermatologic ulcers and cancerous tumor growth, invasion, and metastasis.

"Animal" refers to a living organism having sensation and the power of voluntary movement, and which requires for its existence oxygen and organic food. Examples include, without limitation, members of the human, equine, porcine, bovine, murine, canine, or feline species. In the case of a human, an "animal" may also be referred to as a "patient."

"Mammal" refers to a warm-blooded vertebrate animal.

"Anxiety" includes without limitation the unpleasant emotional state consisting of psychophysiological responses to anticipation of unreal or imagined danger, ostensibly resulting from unrecognized intrapsychic conflict. Physiological concomitants include increased heart rate, altered respiration rate, sweating, trembling, weakness, and fatigue; psychological concomitants include feelings of impending danger, powerlessness, apprehension, and tension. *Dorland 's Illustrated Medical Dictionary,* 27th ed. (W.B. Saunders Co. 1988).

"Anxiety Disorder" includes without limitation mental disorders in which anxiety and avoidance behavior predominate. *Dorland 's Illustrated Medical Dictionary,* 27th ed. (W.B. Saunders Co. 1988). Examples include without limitation panic attack, agoraphobia, panic disorder, acute stress disorder, chronic stress disorder, specific phobia, simple phobia, social phobia, substance induced anxiety disorder, organic anxiety disorder, obsessive compulsive disorder, post-traumatic stress disorder, generalized anxiety disorder, and anxiety disorder NOS. Other anxiety disorders are characterized in *Diagnostic and Statistical Manual of Mental Disorders,* 4th ed. (American Psychiatric Association 1994).

"Attention Deficit Disorder" ("ADD") refers to a disorder characterized by developmentally inappropriate inattention and impulsiveness, with or without hyperactivity. Inattention means a failure to finish tasks started, easily distracted, seeming lack of attention, and difficulty concentrating on tasks requiring sustained attention. Impulsiveness means acting before thinking, difficulty taking turns, problems organizing work, and constant shifting from one activity to another. Hyperactivity means difficulty staying seated and sitting still, and running or climbing excessively.

"Cancer" includes, without limitation, ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, prostate cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

"Compulsive disorder" refers to any disorder characterized by irresistible impulsive behavior. Examples of compulsive disorders include without limitation drug dependence, eating disorders, pathological gambling, ADD, and Tourette's syndrome.

"Demyelinating disease" refers to any disease involving damage to or removal of the myelin sheath naturally surrounding nerve tissue, such as that defined in U.S. Pat. No. 5,859,046 and International Publication No. WO 98/03178, herein incorporated by reference. Examples include without limitation peripheral demyelinating diseases (such as Guillain-Barre syndrome, peripheral neuropathies and Charcot-Marie Tooth disease) and central demyelinating diseases (such as multiple sclerosis).

"Disease" refers to any deviation from or interruption of the normal structure or function of any part, organ or system (or combinations) of the body that is manifested by a characteristic set of symptoms and signs and whose etiology, pathology, and prognosis may be known or unknown. *Dorland's Illustrated Medical Dictionary*, 27th ed. (W.B. Saunders Co. 1988).

"Disorder" refers to any derangement or abnormality of function; a morbid physical or mental state. *Dorland's Illustrated Medical Dictionary*, 27th ed. (W.B. Saunders Co. 1988).

"Substance dependence" refers to a psychologic addiction or a physical tolerance to a substance. Tolerance means a need to increase the dose progressively in order to produce the effect originally achieved by smaller amounts.

"Eating disorder" refers to compulsive overeating, obesity, or severe obesity. Obesity means body weight of 20% over standard height-weight tables. Severe obesity means over 100% overweight.

"Glaucoma" includes without limitation chronic (idiopathic) open-angle glaucomas (e.g., high-pressure, normal-pressure); pupillary block glaucomas (e.g., acute angle-closure, subacute angle-closure, chronic angle-closure, combined-mechanism); developmental glaucomas (e.g., congenital (infantile), juvenile, Anxenfeld-Rieger syndrome, Peters' anomaly, Aniridia); glaucomas associated with other ocular disorders (e.g., glaucomas associated with disorders of the corneal endothelium, iris, ciliary body, lens, retina, choroid and vitreous); glaucomas associated with elevated episcleral venous pressure (e.g., systemic diseases with associated elevated intraocular pressure and glaucoma, corticosteroid-induced glaucoma); glaucomas associated with inflammation and trauma (e.g., glaucomas associated with keratitis, episcleritis, scleritis, uveitis, ocular trauma and hemorrhage); glaucomas following intraocular surgery, e.g., ciliary block (malignant) glaucoma, glaucomas in aphakia and pseudophakia, glaucomas associated with corneal surgery, glaucomas associated with vitreoretinal surgery.

"Glutamate abnormality" refers to any disease, disorder, or condition in which glutamate is implicated, including pathological conditions involving elevated levels of glutamate. Examples of glutamate abnormalities include, without limitation, glaucoma, spinal cord injury, epilepsy, stroke, Alzheimer's disease, Parkinson's disease, ALS, Huntington's disease, schizophrenia, pain, ischemia, peripheral neuropathy (including but not limited to diabetic neuropathy), traumatic brain injury, neuronal insult, inflammatory diseases, anxiety, anxiety disorders, memory impairment, and compulsive disorders.

"Ischemia" refers to localized tissue anemia due to obstruction of the inflow of arterial blood. Global ischemia occurs when blood flow ceases for a period of time, as may result from cardiac arrest. Focal ischemia occurs when a portion of the body, such as the brain, is deprived of its normal blood supply, such as may result from thromboembolytic occlusion of a cerebral vessel, traumatic head injury, edema or brain tumor. Even if transient, both global and focal ischemia can produce widespread neuronal damage. Although nerve tissue damage occurs over hours or even days following the onset of ischemia, some permanent nerve tissue damage may develop in the initial minutes following cessation of blood flow to the brain. Much of this damage is attributed to glutamate toxicity and secondary consequences of reperfusion of the tissue, such as the release of vasoactive products by damaged endothelium, and the release of cytotoxic products, such as free radicals and leukotrienes, by the damaged tissue.

"Memory impairment" refers to a diminished mental registration, retention or recall of past experiences, knowledge, ideas, sensations, thoughts or impressions. Memory impairment may affect short and long-term information retention, facility with spatial relationships, memory (rehearsal) strategies, and verbal retrieval and production. Common causes of memory impairment are age, severe head trauma, brain anoxia or ischemia, alcoholic-nutritional diseases, drug intoxications and neurodegenerative diseases. For example, memory impairment is a common feature of neurodegenerative diseases such as Alzheimer's disease and senile dementia of the Alzheimer type. Memory impairment also occurs with other kinds of dementia such as multi-infarct dementia, a senile dementia caused by cerebrovascular deficiency, and the Lewy-body variant of Alzheimer's disease with or without association with Parkinson's disease. Creutzfeldt-Jakob disease is a rare dementia with which memory impairment is associated. It is a spongiform encephalopathy caused by the prion protein; it may be transmitted from other sufferers or may arise from gene mutations. Loss of memory is also a common feature of brain-damaged patients. Brain damage may occur, for example, after a classical stroke or as a result of an anaesthetic accident, head trauma, hypoglycemia, carbon monoxide poisoning, lithium intoxication, vitamin ($B_1$, thiamine, and $B_{12}$) deficiency, or excessive alcohol use. Korsakoff's amnesic psychosis is a rare disorder characterized by profound memory loss and confabulation, whereby the patient invents stories to conceal his or her memory loss. It is frequently associated with excessive alcohol intake. Memory impairment may furthermore be age-associated; the ability to recall information such as names, places and words seems to decrease with increasing age. Transient memory loss may also occur in patients, suffering from a major depressive disorder, after electro-convulsive therapy.

"Mental disorder" refers to any clinically significant behavioral or psychological syndrome characterized by the presence of distressing symptoms or significant impairment of functioning. Mental disorders are assumed to result from some psychological or organic dysfunction of the individual; the concept does not include disturbances that are essentially conflicts between the individual and society (social deviance).

"Metastasis" refers to "[t]he ability of cells of a cancer to disseminate and form new foci of growth at noncontiguous sites (i.e., to form metastases)." See Hill, R. P, "Metastasis", *The Basic Science of Oncology*, Tannock et al., Eds., pp. 178–195 (McGraw-Hill 1992), herein incorporated by reference. "The transition from in situ tumor growth to metastatic disease is defined by the ability of tumor cells of the primary site to invade local tissues and to cross tissue barriers . . . . To initiate the metastatic process, carcinoma cells must first penetrate the epithelial basement membrane and then invade the interstitial stroma . . . . For distant metastases, intravasation requires tumor cell invasion of the subendothelial basement membrane that must also be negotiated during tumor cell extravasation . . . . The development of malignancy is also associated with tumor-induced angiogenesis [which] not only allows for expansion of the primary tumors, but also permits easy access to the vascular compartment due to defects in the basement membranes of newly formed vessels." See Aznavoorian et al., *Cancer* (1993) 71:1368–1383, herein incorporated by reference.

"Nervous insult" refers to any damage to nervous tissue and any disability or death resulting therefrom. The cause of nervous insult may be metabolic, toxic, neurotoxic, iatrogenic, thermal or chemical, and includes without limitation ischemia, hypoxia, cerebrovascular accident, trauma, surgery, pressure, mass effect, hemorrhage, radiation, vasospasm, neurodegenerative disease, neurodegenerative process, infection, Parkinson's disease, ALS, myelination/ demyelination processes, epilepsy, cognitive disorder, glutamate abnormality and secondary effects thereof.

"Nervous tissue" refers to the various components that make up the nervous system, including without limitation neurons, neural support cells, glia, Schwann cells, vasculature contained within and supplying these structures, the central nervous system, the brain, the brain stem, the spinal cord, the junction of the central nervous system with the peripheral nervous system, the peripheral nervous system and allied structures.

"Neuropathy" refers to any disease or malfunction of the nerves. Neuropathy includes, without limitation, peripheral neuropathy, diabetic neuropathy, autonomic neuropathy and mononeuropathy. Peripheral neuropathy may be idiopathic or induced by any causes including diseases (for example, amyloidosis, alcoholism, HIV, syphilis, virus, autoimmune disorder, cancer, porphyria, arachnoiditis, post herpetic neuralgia, Guillain-Barre syndrome, diabetes including Type I and Type II diabetes), chemicals (for example, toxins, lead, dapsone, vitamins, paclitaxel chemotherapy, HAART therapy) and physical injuries to a particular nerve or nerve plexus (for example, trauma, compression, constriction).

"Neuroprotective" refers to the effect of reducing, arresting or ameliorating nervous insult, and protecting, resuscitating or reviving nervous tissue that has suffered nervous insult.

"Pain" refers to localized sensations of discomfort, distress or agony, resulting from the stimulation of specialized nerve endings. It serves as a protective mechanism insofar as it induces the sufferer to remove or withdraw from the source. *Dorland's Illustrated Medical Dictionary*, 27th ed. (W.B. Saunders Co. 1988). Examples of pain include, without limitation, acute, chronic, cancer, burn, incisional, inflammatory, diabetic neuropathic, and back pain.

"Neuropathic pain" refers to a condition of pain associated with a nerve injury. Depending on the particular syndrome, the pain may be due to alterations of the brain or spinal cord or may be due to abnormalities in the nerve itself. Neuropathic pain may be idiopathic or induced by any causes including diseases (for example, amyloidosis, alcoholism, HIV, syphilis, virus, autoimmune disorder, cancer, porphyria, arachnoiditis, post herpetic neuralgia, Guillain-Barre' syndrome, and diabetes, including Type I and Type II diabetes), chemicals (for example, toxins, lead, dapsone, vitamins, paclitaxel chemotherapy, and HAART therapy) and physical injuries to a particular nerve or nerve plexus (for example, trauma, compression, and constriction).

"Pathological gambling" refers to a condition characterized by a preoccupation with gambling. Similar to psychoactive substance abuse, its effects include development of tolerance with a need to gamble progressively larger amounts of money, withdrawal symptoms, and continued gambling despite severe negative effects on family and occupation.

"Prostate disease" refers to any disease affecting the prostate. Examples of prostate disease include without limitation prostate cancer such as adenocarcinoma and metastatic cancers of the prostate; and conditions characterized by abnormal growth of prostatic epithelial cells such as benign prostatic hyperplasia.

"Schizophrenia" refers to a mental disorder or group of mental disorders characterized by disturbances in form and content of thought (loosening of associations, delusions, hallucinations), mood (blunted, flattened, inappropriate affect), sense of self and relationship to the external world (loss of ego boundaries, dereistic thinking, and autistic withdrawal), and behavior (bizarre, apparently purposeless, and stereotyped activity or inactivity). Examples of schizophrenia include, without limitation, acute, ambulatory, borderline, catatonic, childhood, disorganized, hebephrenic, latent, nuclear, paranoid, paraphrenic, prepsychotic, process, pseudoneurotic, pseudopsychopathic, reactive, residual, schizo-affective and undifferentiated schizophrenia. *Dorland's Illustrated Medical Dictionary*, 27th ed. (W.B. Saunders Co. 1988).

"TGF-β" refers to transforming growth factor beta. TGF-β is recognized as a prototype of multifunctional growth factors. It regulates various cell and tissue functions, including cell growth and differentiation, angiogenesis, wound healing, immune function, extracellular matrix production, cell chemotaxis, apoptosis and hematopoiesis.

"TGF-βabnormality" refers to any disease, disorder or condition in which TGF-β is implicated, including diseases disorders and conditions characterized by an abnormal level of TGF-β.

"Abnormal level of TGF-β" refers to a measurable variance from normal levels of TGF-β, as determined by one of ordinary skill in the art using known techniques.

"Therapeutic window of opportunity" or "window" refers, in relation to stroke, to the maximal delay between the onset of stroke and the initiation of efficacious therapy.

"Tourette's syndrome" refers to an autosomal multiple tic disorder characterized by compulsive swearing, multiple muscle tics and loud noises. Tics are brief, rapid, involuntary movements that can be simple or complex; they are stereotyped and repetitive, but not rhythmic. Simple tics, such as eye blinking, often begin as nervous mannerisms. Complex tics often resemble fragments of normal behavior.

"Treating" refers to:
 (i) preventing a disease, disorder or condition from occurring in an animal that may be predisposed to the disease, disorder and/or condition but has not yet been diagnosed as having it;
 (ii) inhibiting the disease, disorder or condition, i.e., arresting its development; and/or
 (iii) relieving the disease, disorder or condition, i.e., causing regression of the disease, disorder and/or condition.

"Treating substance dependence" refers to suppressing the psychologic addiction or physical tolerance to the drug of abuse, and/or relieving and/or preventing a withdrawal syndrome resulting from the drug dependence.

"Dependence" refers to a maladaptive pattern of substance use, leading to clinically significant impairment or distress. Dependence is typically characterized by tolerance and/or withdrawal. Substances for which dependence may be developed include, without limitation, depressants (opioids, synthetic narcotics, barbiturates, glutethimide, methyprylon, ethchlorvynol, methaqualone, alcohol); anxiolytics (diazepam, chlordiazepoxide, alprazolam, oxazepam, temazepam); stimulants (amphetamine, methamphetamine, cocaine); and hallucinogens (LSD, mescaline, peyote, marijuana).

"Tolerance" refers to an acquired reaction to a substance characterized by diminished effect with continued use of the same dose and/or a need for increased doses to achieve intoxication or desired effect previously achieved by lower doses. Both physiological and psychosocial factors may contribute to the development of tolerance. With respect to physiological tolerance, metabolic and/or functional tolerance may develop. By increasing the rate of metabolism of the substance, the body may be able to eliminate the substance more readily. Functional tolerance is defined as a decrease in sensitivity of the central nervous system to the substance.

"Withdrawal" refers to a syndrome characterized by untoward physical changes that occur following cessation of or reduction in substance use, or administration of a pharmacologic antagonist.

One of ordinary skill in the art will recognize that there are alternative nomenclatures, nosologies and classification systems for the diseases, disorders and conditions defined above, and that such systems evolve with medical scientific progress.

Unless the context clearly dictates otherwise, the definitions of singular terms may be extrapolated to apply to their plural counterparts as they appear in the application; likewise, the definitions of plural terms may be extrapolated to apply to their singular counterparts as they appear in the application.

COMPOUNDS OF THE INVENTION

Specifically, the present invention relates to a compound of formula I

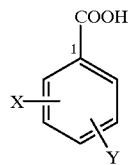

or a pharmaceutically acceptable equivalent, wherein:

X is —W—Z;

W is a bond or a linking group;

Z is a terminal group; and

Y is —COOH oriented meta or para relative to C-1.

Linking groups include without limitation divalent hydrocarbon chains, ethers, sulfides and amines, wherein the hydrocarbon chain, whether alone or part of the ether, sulfide or amine, may be saturated or unsaturated, straight or branched, open or closed, unsubstituted or substituted with one or more substituent(s), preferably, independently selected from the group consisting of $C_1$–$C_6$ alkoxy, $C_2$–$C_6$ alkenyloxy, phenoxy, benzyloxy, hydroxy, carboxy, carbamido, carbamoyl, carbamyl, carbonyl, carbozoyl, amino, hydroxyamino, formamido, formyl, guanyl, cyano, cyanoamino, isocyano, isocyanato, diazo, azido, hydrazino, triazano, nitrilo, isonitrilo, nitro, nitroso, isonitroso, nitrosamino, imino, nitrosimino, oxo, $C_1$–$C_6$ alkylthio, sulfamino, sulfamoyl, sulfeno, sulfhydryl, sulfinyl, sulfo, sulfonyl, sulfoxy, thiocarboxy, thiocyano, isothiocyano, thioformamido, halo, haloalkyl, chlorosyl, chloryl, perchloryl, trifluoromethyl, iodosyl, iodyl, phosphino, phosphinyl, phospho, phosphono, arsino, selanyl, diselanyl, siloxy, silyl and silylene.

Preferably, W is a bond, —$(CR_1R_2)_n$—, —$(CR_1R_2)_nO(CR_3R_4)_m$—, —$(CR_1R_2)_nS(CR_3R_4)_m$— or —$(CR_1R_2)_nNR(CR_3R_4)_m$—, wherein m and n are independently 0–9, and R, $R_1$, $R_2$, $R_3$ and $R_4$ are independently hydrogen, $C_1$–$C_6$ alkyl, $C_2$–$C_6$ alkenyl, $C_2$–$C_6$ alkynyl, $C_6$–$C_{14}$ aryl, heteroaryl, $C_6$–$C_{14}$ carbocycle, heterocycle, halo, hydroxy, sulfhydryl, nitro, amino or $C_1$–$C_6$ alkoxy, and said alkyl, alkenyl, alkynyl, aryl, heteroaryl, carbocycle, heterocycle or alkoxy is independently unsubstituted or substituted with one or more substituent(s). More preferably, R, $R_1$, $R_2$, $R_3$ and $R_4$ are each hydrogen and the total number of carbon atoms in W is 2–6.

Preferably, Z is a metal binding group. More preferably, Z is —COOH, —$COR_5$, —$OR_5$, —$CF_3$, —CN, —F, —Cl, —Br, —I, —NO, —$NO_2$, —C(O)($NR_5OR_6$), —C(O)($NR_5PO_3H_2$), —C(O)($NR_5R_6$), =NOH, —$NR_5$ (P(O)($R_6$)OH), =$NR_5$, —N=$NR_5$, —N($R_5$)CN, —$NR_5(CR_6R_7)_p$COOH, —$NR_5$(CO)$NR_6R_7$, —$NR_5$(COOR$_6$), —$NR_5$(CO)$R_6$, —$NR_5$(OR$_6$), —$NR_5R_6$, —$NR_5$(SO$_2R_6$), —O(CO)$R_5$, —$OR_5$, —$SO_2$(OR$_5$), —$SO_2$($NR_5R_6$), —$SO_2R_5$, —$SO_3R_5$, —$SNR_5$(OR$_6$), —S($NR_5R_6$), —$SR_5$, —$SSR_5$, —P(O)(OH)$OR_5$, —P(O)(OH)$R_5$ or —P$R_5R_6$, wherein p is 0–6, and $R_5$, $R_6$ and $R_7$ are independently hydrogen, $C_1$–$C_9$ alkyl, $C_2$–$C_9$ alkenyl, $C_2$–$C_9$ alkynyl, $C_6$–$C_{14}$ aryl, heteroaryl, $C_6$–$C_{14}$ carbocycle, heterocycle, halo, hydroxy, sulfhydryl, nitro, amino or $C_1$–$C_9$ alkoxy, and said alkyl, alkenyl, alkynyl, aryl, heteroaryl, carbocycle, heterocycle or alkoxy is independently unsubstituted or substituted with one or more substituent(s). More preferably, Z is —NH($CR_6R_7)_p$COOH, —PO(OH)$OR_5$, —PO(OH)$R_5$, —$NR_5$(P(O)(OH)$R_6$), —CON($R_5$)(OH) or —SH.

In a preferred embodiment of formula I, X is —$SO_2$-aryl, carboxy, S-aryl, nitro, halo, amino, —$SO_3$H, —$(CR_1R_2)_n$CO$_2R_3$, —$NR_5(CR_1R_2)CO_2R_3$, —(C=O)-aryl, —(C=O)-phenoxy-aryl, —(C=O)$NR_5$-aryl, —O$(CR_1R_2)_n$—S—S—$(CR_3R_4)_m$O-aryl, hydroxy, —$(CR_1R_2)_nNR_5(CR_3R_4)_m$-heteroaryl, —NR—(C=O)-alkyl, and $NR_5$—(C=O)-aryl; wherein m and n are independently 0–9; $R_1$, $R_2$, $R_3$, $R_4$, and $R_5$ are independently hydrogen, $C_1$–$C_6$ alkyl, $C_2$–$C_6$ alkenyl, $C_2$–$C_6$ alkynyl, $C_6$–$C_{14}$ aryl, heteroaryl, $C_6$–$C_{14}$ carbocycle, heterocycle, halo, hydroxy, sulfhydryl, nitro, amino or $C_1$–$C_6$ alkoxy; wherein said alkyl, alkenyl, alkynyl, aryl, heteroaryl, carbocycle, heterocycle or alkoxy is independently unsubstituted or substituted with one or more substituent(s).

In another preferred embodiment of formula I:

X is —$(CR_1R_2)_nNH(CR_3R_4)_m$COOH, —PO(OH)$OR_5$, —$(CR_1R_2)_nP(O)(OH)OR_5$, —NH—$(CR_3R_4)_m$-heteroaryl, —NH(P(O)(OH)$R_6$), —$(CR_1R_2)_nNH(P(O)(OH)R_6)$, —CON($R_5$)(OH), —$(CR_1R_2)_n$CON($R_5$)(OH), —$(CR_1R_2)_n$SH, —O$(CR_3R_4)_m$SH, —$SO_2$NH-aryl, —$NR_5$(C=O)—$(CR_1R_2)_n$(C=O)-aryl, —$SO_2$NH-aryl-N(C=O)—$CH_2$(C=O)-aryl, —O-aryl wherein aryl in —O-aryl is substituted by at least one of nitro or carboxy, or

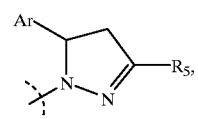

wherein X is oriented meta or para to C-1;

m and n are independently 1–3, provided that when X is —O$(CR_3R_4)_m$SH, then m is 2 or 3;

$R_1$, $R_2$, $R_3$, $R_4$, $R_5$, and $R_6$ are independently hydrogen, $C_1$–$C_6$ alkyl, $C_2$–$C_6$ alkenyl, $C_2$–$C_6$ alkynyl, $C_6$–$C_{14}$ aryl, heteroaryl, $C_6$–$C_{14}$ carbocycle, heterocycle, halo, hydroxy, sulfhydryl, nitro, amino or $C_1$–$C_6$ alkoxy, wherein said alkyl, alkenyl, alkynyl, aryl, heteroaryl, carbocycle, heterocycle or alkoxy is independently unsubstituted or substituted with one or more substituent(s); and Y is -COOH oriented meta or para relative to C-1;

and preferably, when X is —PO(OH)OR$_5$ or —(CR$_1$R$_2$)$_n$P(O)(OH)OR$_5$, then R$_5$ is not H or methyl; when X is —NH(P(O)(OH)R$_6$) or —(CR$_1$R$_2$)$_n$NH(P(O)(OH)R$_6$), then R$_6$ is not benzyl unsubstituted or substituted with amino; and when X is —CON(R$_5$)(OH), then R$_5$ is not H or methyl.

Possible substituents of said alkyl, alkenyl, alkynyl, aryl, heteroaryl, carbocycle, heterocycle and alkoxy include, without limitation, $C_1$–$C_6$ alkyl, $C_2$–$C_6$ alkenyl, $C_2$–$C_6$ alkynyl, $C_1$–$C_6$ alkoxy, $C_2$–$C_6$ alkenyloxy, phenoxy, benzyloxy, hydroxy, carboxy, hydroperoxy, carboxy, carbamido, carbamoyl, carbamyl, carbonyl, carbozoyl, amino, hydroxyamino, formamido, formyl, guanyl, cyano, cyanoamino, isocyano, isocyanato, diazo, azido, hydrazino, triazano, nitrilo, isonitrilo, nitro, nitroso, isonitroso, nitrosamino, imino, nitrosimino, oxo, $C_1$–$C_6$ alkylthio, sulfamino, sulfamoyl, sulfeno, sulfhydryl, sulfinyl, sulfo, sulfonyl, sulfoxy, thiocarboxy, thiocyano, isothiocyano, thioformamido, halo, haloalkyl, chlorosyl, chloryl, perchloryl, trifluoromethyl, iodosyl, iodyl, phosphino, phosphinyl, phospho, phosphono, arsino, selanyl, diselanyl, siloxy, silyl, silylene and carbocyclic and heterocyclic moieties. Carbocyclic moieties include alicyclic and aromatic structures.

Examples of carbocyclic and heterocyclic moieties include, without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

In a preferred embodiment of formula I, X is oriented meta relative to C-1, and Y is oriented ortho relative to X and para relative to C-1. More preferably, W is a bond, —(CH$_2$)$_n$—NH—(CH$_2$)$_m$— or —(CH$_2$)$_n$—; m is 1–3; n is 0–3; and Z is -CO$_2$H, —NO$_2$, —NH$_2$, —SO$_3$H, halo, $C_5$–$C_6$ heteroaryl, carboxyphenylthio, or mono- or dicarboxyphenylsulfonyl.

Examples of this embodiment are set forth below in Table I.

TABLE I

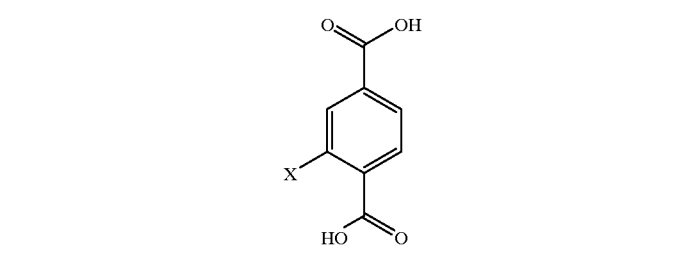

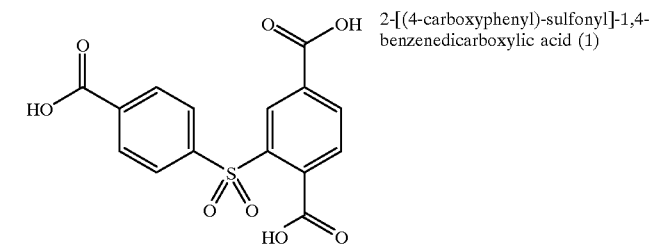

2-[(4-carboxyphenyl)-sulfonyl]-1,4-benzenedicarboxylic acid (1)

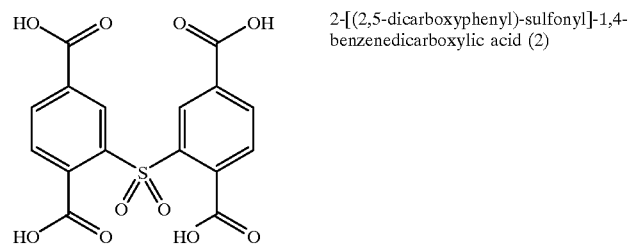

2-[(2,5-dicarboxyphenyl)-sulfonyl]-1,4-benzenedicarboxylic acid (2)

TABLE I-continued
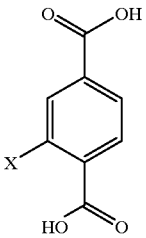
| | |
|---|---|
| 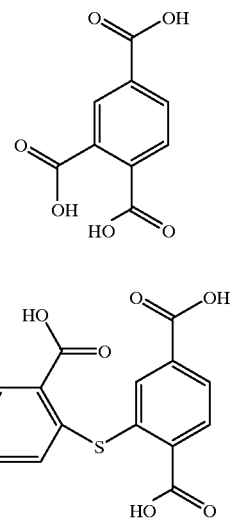 | 1,2,4-benzenetricarboxylic acid (3) |
| 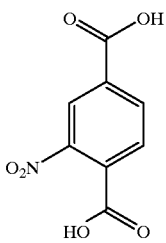 | 2-[(2-carboxyphenyl)thio]-1,4-benzenedicarboxylic acid (4) |
| 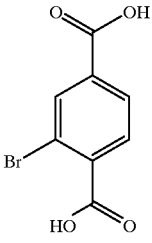 | 2-nitro-1,4-benzenedicarboxylic acid (5) |
| 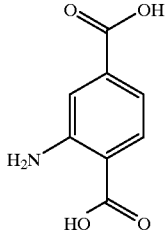 | 2-bromo-1,4-benzenedicarboxylic acid (6) |
|  | 2-amino-1,4-benzenedicarboxylic acid (7) |

TABLE I-continued

| Structure | Name |
|---|---|
| (benzene ring with CO₂H at positions 1 and 4, X at position 2) | |
| (benzene ring with CO₂H at positions 1 and 4, NaO₃S at position 2) | 2-sulfoterephthalic acid, monosodium salt (8) |
| (benzene ring with CO₂H at positions 1 and 4, CH₂CO₂H at position 2) | 2-carboxymethyl-1,4-benzenedicarboxylic acid (9) |
| (benzene ring with CO₂H at positions 1 and 4, NH-CH₂-(2-furanyl) at position 2) | 2-[(2-furanylmethyl)-amino]-1,4-benzenedicarboxylic acid (10) |
| (benzene ring with CO₂H at positions 1 and 4, NH-CH₂-CO₂H at position 2) | 2-[(carboxymethyl)amino]-1,4-benzenedicarboxylic acid (11) |

In another preferred embodiment of formula I, X is oriented ortho relative to C-1, and Y is oriented para relative to X and meta relative to C-1.

More preferably, (1) when W is a bond, then Z is —CO$_2$H, —OH, —NO$_2$, —C(O)(NHR$_5$), —SR$_5$, —COR$_5$, or —NH(CH$_2$R$_5$), and R$_5$ is an aryl or a heteroaryl that is independently unsubstituted or substituted with one or more alkyl, nitro or carboxy group(s); and (2) when W is —(CH$_2$)$_n$— and n is 1–3, then Z is —SH.

Examples of this embodiment are set forth below in Table II.

TABLE II

| (structure: benzene with X at 4-position, COOH at 1 and 3 positions) | |
|---|---|
| (4-nitrobenzoyl substituted structure) | 4-(4-nitrobenzoyl)-1,3-benzenedicarboxylic acid (12) |
| (bis-dicarboxybenzoyl phenoxy structure) | 4-[4-(2,4-dicarboxybenzoyl)phenoxy]-1,2-benzenedicarboxylic acid (13) |
| (2,4,6-trimethylphenyl amide structure) | 4-[[(2,4,6-trimethylphenyl)amino]-carbonyl]-1,3-benzenedicarboxylic acid (14) |
| (4-nitro substituted structure) | 4-nitro-1,3-benzenedicarboxylic acid (15) |
| (1-naphthalenyl amide structure) | 4-[(1-naphthalenylamino)-carbonyl]-1,3-benzenedicarboxylic acid (16) |
| (1,2,4-benzenetricarboxylic acid structure) | 1,2,4-benzenetricarboxylic acid (17) |

TABLE II-continued

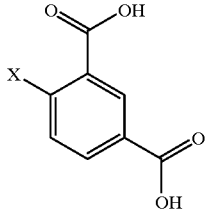

4-[(2-carboxyphenyl)thio]-1,3-benzenedicarboxylic acid (18)

4-[3-[[3-(2,4-dicarboxyphenoxy)propyl]-dithio]propoxy]-1,3-benzenedicarboxylic acid (19)

4-hydroxy-1,3-benzenedicarboxylic acid (20)

4-[(2-furanylmethyl)amino]-1,3-benzenedicarboxylic acid (21)

4-(2-mercaptoethyl)-1,3-benzenedicarboxylic acid (22)

In another preferred embodiment of formula I, X is oriented meta relative to C-1, and Y is oriented meta relative to C-1.

More preferably, (1) when W is a bond, —$(CH_2)_n$— or —$O(CH_2)_m$— and m and n are independently 0–3, then Z is —$SO_3H$, —$NO_2$, —$NH_2$, —$CO_2H$, —OH, —$PO_3H$, —CO (NHOH) or —SH; (2) when W is —(CH$_2$)$_m$NH(CH$_2$)$_m$— and m and n are independently 0–3, then Z is —CO$_2$H or C$_5$–C$_6$ heteroaryl; and (3) when W is a bond, then Z is either (a) a heteroaryl that is unsubstituted or substituted with an aryl that is unsubstituted or substituted with one or more C$_1$–C$_3$ alkyl, halo, nitro or hydroxy group(s), or (b) —SO$_2$(NHR$_6$) or —NH(COR$_6$), wherein R$_6$ is an aryl that is unsubstituted or substituted with one or more nitro, amino, halo or hydroxy group(s).

Examples of this embodiment are set forth below in Table III.

TABLE III

| Structure | Name |
|---|---|
| (5-X-substituted 1,3-benzenedicarboxylic acid core structure) | |
| (structure of compound 23) | 5-[4,5-dihydro-5-(4-hydroxyphenyl)-3-phenyl-1H-pyrazol-1-yl]-1,3-benzenedicarboxylic acid (23) |
| (structure of compound 24) | 5-(4,5-dihydro-3-methyl-5-phenyl-1H-pyrazol-1-yl)-1,3-benzenedicarboxylic acid (24) |
| (structure of compound 25) | 5-[[(4-chloro-3-nitrophenyl)amino]sulfonyl]-1,3-benzenedicarboxylic acid (25) |

TABLE III-continued
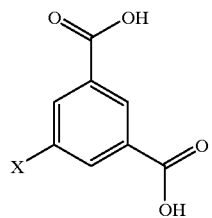
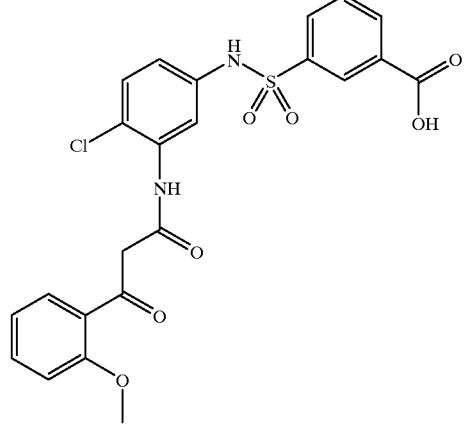
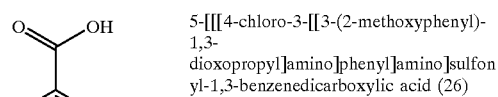
5-[[[4-chloro-3-[[3-(2-methoxyphenyl)-1,3-dioxopropyl]amino]phenyl]amino]sulfonyl-1,3-benzenedicarboxylic acid (26)
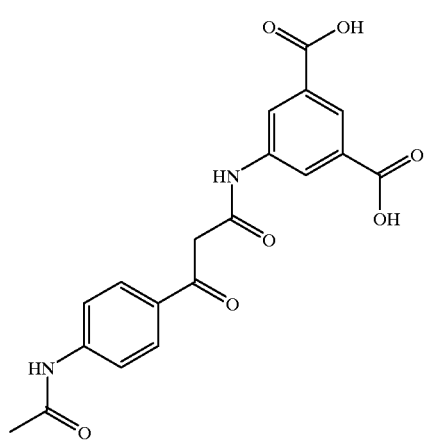
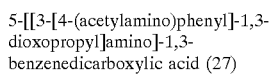
5-[[3-[4-(acetylamino)phenyl]-1,3-dioxopropyl]amino]-1,3-benzenedicarboxylic acid (27)
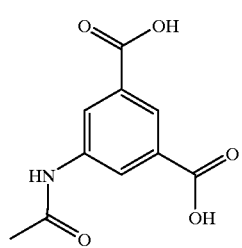
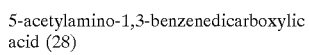
5-acetylamino-1,3-benzenedicarboxylic acid (28)

TABLE III-continued
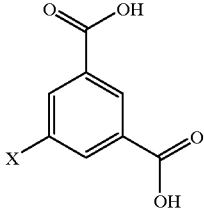
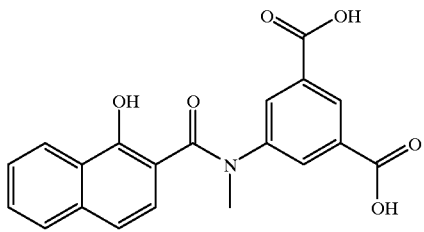
5-[[(1-hydroxy-2-naphthalenyl)carbonyl]-methylamino]-1,3-benzenedicarboxylic acid (29)
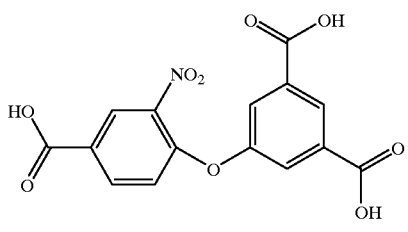
5-(4-carboxy-2-nitrophenoxy)-1,3-benzenedicarboxylic acid (30)
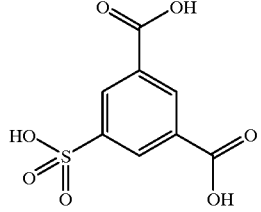
5-sulfo-1,3-benzenedicarboxylic acid (31)
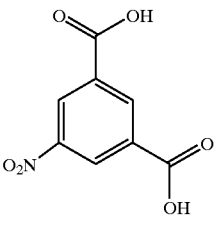
5-nitro-1,3-benzenedicarboxylic acid (32)
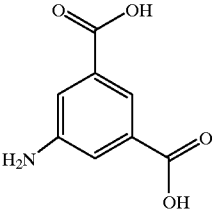
5-amino-1,3-benzenedicarboxylic acid (33)

TABLE III-continued
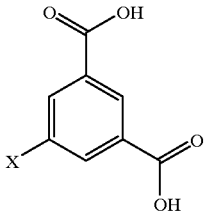
| | |
|---|---|
| 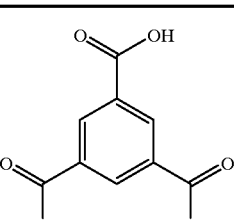 | 1,3,5-benzenetricarboxylic acid (34) |
| 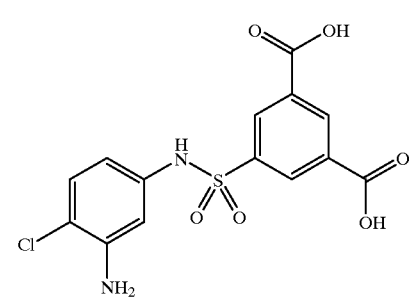 | 5-[[(3-amino-4-chlorophenyl)amino]sulfonyl]-1,3-benzenedicarboxylic acid (35) |
| 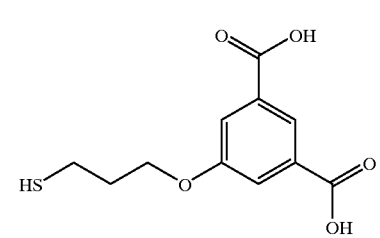 | 5-(3-mercaptopropoxy)-1,3-benzenedicarboxylic acid (36) |
| 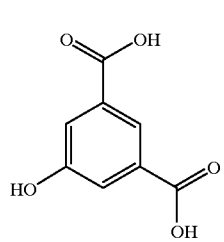 | 5-hydroxy-1,3-benzenedicarboxylic acid (37) |
| 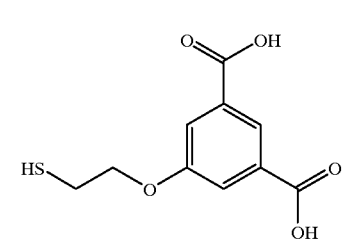 | 5-(2-mercaptoethoxy)-1,3-benzenedicarboxylic acid (38) |

TABLE III-continued
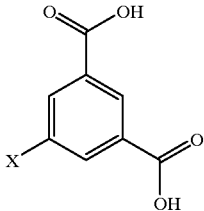
| | |
|---|---|
| 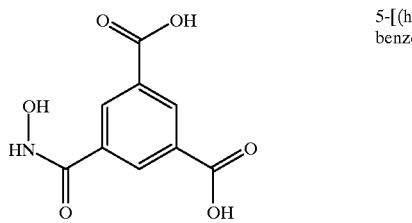 | 5-[(hydroxyamino)-carbonyl]-1,3-benzenedicarboxylic acid (39) |
| 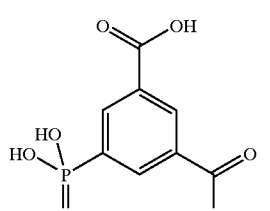 | 5-phosphono-1,3-benzenedicarboxylic acid (40) |
| 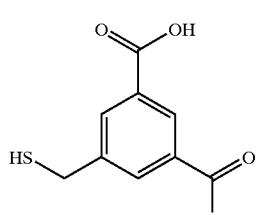 | 5-mercaptomethyl-1,3-benzenedicarboxylic acid (41) |
| 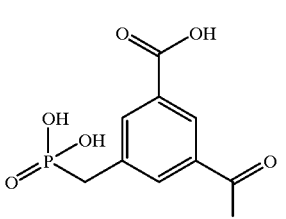 | 5-phosphonomethyl-1,3-benzenedicarboxylic acid (42) |
| 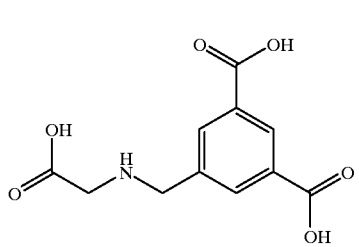 | 5-[[(carboxymethyl)amino]-methyl]-1,3-benzenedicarboxylic acid (43) |
| 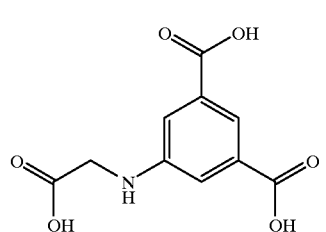 | 5-[(carboxymethyl)amino]-1,3-benzenedicarboxylic acid (44) |

TABLE III-continued

| Structure | Name |
|---|---|
| (X-substituted 1,3-benzenedicarboxylic acid core) | |
| 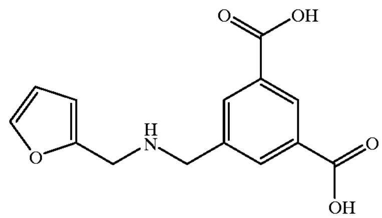 | 5-[[(2-furanylmethyl)amino]-methyl]-1,3-benzenedicarboxylic acid (45) |
| 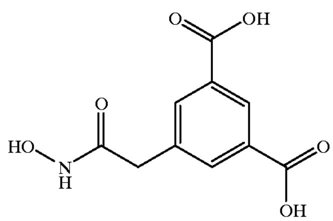 | 5-[2-(hydroxyamino)-2-oxoethyl]-1,3-benzenedicarboxylic acid (46) |
| 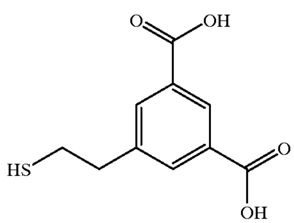 | 5-(2-mercaptoethyl)-1,3-benzenedicarboxylic acid (47) |

The compounds of formula I possess one or more asymmetric carbon center(s) and are thus capable of existing in the form of optical isomers as well as in the form of racemic or non-racemic mixtures of optical isomers. The optical isomers can be obtained by resolution of the racemic mixtures according to conventional processes well known in the art, for example by formation of diastereoisomeric salts by treatment with an optically active acid or base and then separation of the mixture of diastereoisomers by crystallization followed by liberation of the optically active bases from these salts. Examples of appropriate acids are tartaric, diacetyltartaric, dibenzoyltartaric, ditoluoyltartaric, and camphorsulfonic acid.

A different process for separating optical isomers involves the use of a chiral chromatography column optimally chosen to maximize the separation of the enantiomers. Still another available method involves synthesis of covalent diastereoisomeric molecules, for example, esters, amides, acetals, ketals, and the like, by reacting compounds used in the inventive methods and pharmaceutical compositions with an optically active acid in an activated form, an optically active diol or an optically active isocyanate. The synthesized diastereoisomers can be separated by conventional means such as chromatography, distillation, crystallization or sublimation, and then hydrolyzed to deliver the enantiomerically pure compound. In some cases hydrolysis to the parent optically active drug is not necessary prior to dosing the patient since the compound can behave as a prodrug. The optically active compounds of the present invention can likewise be obtained by utilizing optically active starting materials.

It is understood that the compounds of formula I encompass individual optical isomers as well as racemic and non-racemic mixtures.

METHODS OF THE INVENTION

Methods for Inhibiting NAALADase Enzyme Activity

The present invention relates to a method for inhibiting NAALADase enzyme activity in an animal or a mammal comprising administering to said animal or mammal an effective amount of a compound of formula I, as defined above.

Methods for Treating Glutamate Abnormalities

The present invention further relates to a method for treating a glutamate abnormality in an animal or a mammal, comprising administering to said animal or mammal an effective amount of a compound of formula I, as defined above.

Preferred glutamate abnormalities to be treated are compulsive disorders, stroke, demyelinating disease, schizophrenia, Parkinson's disease, ALS, diabetic neuropathy, pain, anxiety, anxiety disorders, glaucoma, and memory impairment. More preferably, the compulsive disorder is alcohol, nicotine or cocaine dependence.

Stroke patients often experience a significant temporal delay between the onset of ischemia and the time to initiation of therapy. Thus, there is a need for neuroprotectants with a long therapeutic window of opportunity. It is expected that the compounds of formula I have a therapeutic window of opportunity of at least 1 hour. Accordingly, when the glutamate abnormality is stroke, the compound of formula I may be administered to said animal or mammal 60 minutes, 120 minutes, or more following onset of stroke.

Without being bound to any particular mechanism of action, preferred compounds of the present invention are expected to be those that block glutamate release pre-synaptically without interacting with post-synaptic glutamate receptors. Such compounds would be devoid of the behavioral toxicities associated with post-synaptic glutamate antagonists.

Methods for Effecting a Neuronal Activity

The present invention further relates to a method for effecting a neuronal activity in an animal or a mammal, comprising administering to said animal or mammal an effective amount of a compound of formula I, as defined above.

The neuronal activity that is effected by the inventive method may be stimulation of damaged neurons, promotion of neuronal regeneration, prevention of neurodegeneration, or treatment of a neurological disorder.

Examples of neurological disorders that are treatable by the methods of the present invention include without limitation: trigeminal neuralgia; glossopharyngeal neuralgia; Bell's Palsy, myasthenia gravis; muscular dystrophy; Amyotrophic Lateral Sclerosis ("ALS"); progressive muscular atrophy; progressive bulbar inherited muscular atrophy; herniated, ruptured or prolapsed invertebrate disk syndromes; cervical spondylosis; plexus disorders; thoracic outlet destruction syndromes; neuropathy; pain; Alzheimer's disease; Parkinson's disease; ALS; and Huntington's disease.

The inventive method is particularly useful for treating peripheral neuropathy and neuropathic pain such as peripheral neuropathy or neuropathic pain induced by HIV, chemicals (for example, toxins, lead, dapsone, vitamins, paclitaxel chemotherapy, HAART therapy), or diabetes such as type 1 and type 2 diabetes.

The inventive method is also particularly useful for treating traumatic brain injury, physical damage to spinal cord, stroke associated with brain damage, demyelinating disease, and neurological disorders relating to neurodegeneration such as Alzheimer's disease, Parkinson's disease, and ALS.

When the neurological disorder is pain, the compound of formula I is preferably administered in combination with an effective amount of morphine.

Methods for Treating Prostate Diseases

The present invention further relates to a method for treating a prostate disease in an animal or a mammal, comprising administering to said animal or mammal an effective amount of a compound of formula I, as defined above.

Methods for Treating Cancers

The present invention further relates to a method for treating cancer in an animal or a mammal, comprising administering to said animal or mammal an effective amount of a compound of formula I, as defined above.

Preferred cancers to be treated are those in tissues where NAALADase resides, including without limitation the brain, kidney, and testis.

Methods for Inhibiting Angiogenesis

The present invention further relates to a method for inhibiting angiogenesis in an animal or a mammal, comprising administering to said animal or mammal an effective amount of a compound of formula I, as defined above.

Angiogenesis may be necessary for fertility or metastasis of cancer tumors, or may be related to an angiogenic-dependent disease. Thus, the inventive methods may also be useful for treating an angiogenic-dependent disease including, without limitation, rheumatoid arthritis, cardiovascular diseases, neovascular diseases of the eye, peripheral vascular disorders, dermatologic ulcers, and cancerous tumor growth, invasion, and metastasis.

Methods for Treating Tgf-β Abnormalities

The present invention further relates to a method for treating a TGF-β abnormality in an animal or a mammal, comprising administering to said animal or mammal an effective amount of a compound of formula I, as defined above. Preferred TGF-β abnormalities to be treated are neurodegenerative disorders, extra-cellular matrix formation disorders, cell-growth related diseases, infectious diseases, immune related diseases, epithelial tissue scarring, collagen vascular diseases, fibroproliferative disorders, connective tissue disorders, inflammation, inflammatory diseases, respiratory distress syndrome, and infertility.

Preferred neurodegenerative disorders to be treated are neural tissue damage resulting from ischemia reperfusion injury, myelination, and neurodegeneration.

Preferred cell-growth related disorders to be treated are those affecting kidney cells, hematopoietic cells, lymphocytes, epithelial cells, and endothelial cells.

Preferred infectious diseases to be treated are those caused by a macrophage pathogen, particularly a macrophage pathogen such as bacteria, yeast, fungi, viruses, protozoa, *Trypanosoma cruzi, Histoplasma capsulatum, Candida albicans, Candida parapsilosis, Cryptococcus neoformans*, Salmonella, Pneumocystis, Toxoplasma, Listeria, Mycobacteria, Rickettsia, and Leishmania. Mycobacteria include without limitation *Mycobacterium tuberculosis* and *Mycobacterium leprae*. Toxoplasma includes without limitation *Toxoplasma gondii*. Rickettsia includes without limitation *R. prowazekii, R. coronii*, and *R. tsutsugamushi*.

Other preferred infectious diseases to be treated are single or multiple cutaneous lesions, mucosal disease, Chagas' disease, acquired immunodeficiency syndrome ("AIDS"), toxoplasmosis, leishmaniasis, trypanosomiasis, shistosomiasis, cryptosporidiosis, Mycobacterium avium infections, *Pneumocystis carinii* pneumonia, and leprosy.

Preferred immune related diseases to be treated are autoimmune disorders; impaired immune function; and immunosuppression associated with an infectious disease, particularly, trypanosomal infection, viral infection, human immunosuppression virus, human T cell lymphotropic virus ("HTLV-1"), lymphocytic choriomeningitis virus, or hepatitis.

Preferred collagen vascular diseases to be treated include progressive systemic sclerosis ("PSS"), polymyositis, scleroderma, dermatomyositis, eosinophilic fascitis, morphea, Raynaud's syndrome, interstitial pulmonary fibrosis, scleroderma, and systemic lupus erythematosus.

Preferred fibroproliferative disorders to be treated include diabetic nephropathy, kidney disease, proliferative vitreoretinopathy, liver cirrhosis, biliary fibrosis, and myelofibrosis. Especially preferred kidney diseases include mesangial proliferative glomerulonephritis, crescentic glomerulonephritis, diabetic neuropathy, renal interstitial fibrosis, renal fibrosis in transplant patients receiving cyclosporin, and HIV-associated nephropathy.

Preferred connective tissue disorders to be treated include scleroderma, myelofibrosis, and hepatic, intraocular and pulmonary fibrosis.

Preferred inflammatory diseases to be treated are associated with PSS, polymyositis, scleroderma, dermatomyositis, eosinophilic fascitis, morphea, Raynaud's syndrome, interstitial pulmonary fibrosis, scleroderma, systemic lupus erythematosus, diabetic nephropathy, kidney disease, proliferative vitreoretinopathy, liver cirrhosis, biliary fibrosis, myelofibrosis, mesangial proliferative glomerulonephritis, crescentic glomerulonephritis, diabetic neuropathy, renal interstitial fibrosis, renal fibrosis in transplant patients receiving cyclosporin, or HIV-associated nephropathy.

Without being limited to anyparticular mechanism of action, preferred compounds of the present invention treat inflammatory diseases by regulating TGF-β and/or inhibiting myeloperoxidase.

Other uses associated with the compounds' TGF-β regulating properties include:

- stimulating growth of tissue, glands or organs, particularly growth that would enhance milk production or weight gain;
- stimulating cell proliferation, particularly proliferation of fibroblasts, mesenchymal cells, or epithelial cells;
- inhibiting cell growth, particularly of epithelial cells, endothelial cells, T and B lymphocytes, and thymocytes;
- inhibiting expression of adipose, skeletal muscle and hematopoietic phenotypes, neoplasms, non-cytocidal viral or other pathogenic infections and autoimmune disorders;
- mediating disease resistance and susceptibility;
- suppressing cellular immune response;
- inhibiting scar tissue formation, preferably in skin or other epithelial tissue that has been damaged by wounds resulting from accidental injury, surgical operations, trauma-induced lacerations or other trauma, or wounds involving the peritoneum for which the excessive connective tissue formation is abdominal adhesions;
- increasing the effectiveness of a vaccine, particularly a vaccine for an allergy towards, e.g., dust or hayfever; and
- inhibiting polyp formation.

Diagnostic Methods and Kits

The compounds of the present invention are useful for in vitro and in vivo diagnostic methods for detecting diseases, disorders and conditions where NAALADase levels are altered including, without limitation, neurological disorders, glutamate abnormalities, neuropathy, pain, compulsive disorders, prostate diseases, cancers and TGF-β abnormalities.

Accordingly, the present invention also relates to a method for detecting a disease, disorder or condition where NAALADase levels are altered, comprising:

(i) contacting a sample of bodily tissue or fluid with a compound of the invention, as defined above, wherein said compound binds to any NAALADase in said sample; and (ii) measuring the amount of any NAALADase bound to said sample, wherein the amount of NAALADase is diagnostic for said disease, disorder or condition.

The present invention further relates to a method for detecting a disease, disorder or condition where NAALADase levels are altered in an animal or a mammal, comprising:

(i) labeling a compound of the invention, as defined above, with an imaging reagent;

(ii) administering to said animal or mammal an effective amount of the labeled compound;

(iii) allowing said labeled compound to localize and bind to NAALADase present in said animal or mammal; and (iv) measuring the amount of NAALADase bound to said labeled compound, wherein the amount of NAALADase is diagnostic for said disease, disorder or condition.

The present invention further relates to a diagnostic kit for detecting a disease, disorder or condition where NAALADase levels are altered, comprising a compound of the invention, as defined above, labeled with a marker. The kit may further comprise buffering agents, agents for reducing background interference, control reagents andlor apparatus for conducting the test.

Examples of bodilytissues and fluids include, without limitation, prostate tissue, ejaculate, seminal vesicle fluid, prostatic fluid, urine, blood, saliva, tears, sweat, lymph and sputum.

The compound may be labeled with a marker using techniques known in the art. Useful markers include, without limitation, enzymatic markers and imaging reagents. Examples of imaging reagents include radiolabels such as $^{131}I$, $^{111}In$, $^{123}I$, $^{99}Tc$, $^{32}P$, $^{125}I$, $^{3}H$ and $^{14}C$; fluorescent labels such as fluorescein and rhodamine; and chemiluminescers such as luciferin.

The amount of NAALADase can be measured using techniques known in the art including, without limitation, assays (such as immunometric, calorimetric, densitometric, spectrographic and chromatographic assays) and imaging techniques (such as magnetic resonance spectroscopy (MRS), magnetic resonance imaging (MRI), single-photon emission computed tomography (SPECT) and positron emission tomography (PET)).

The amount of NAALADase can be measured in vivo using known imaging techniques, as described above.

INCORPORATION BY REFERENCE

The relationship between NAALADase inhibitors and glutamate, and the effectiveness of NAALADase inhibitors in treating and detecting various diseases, disorders and conditions have been discussed in U.S. Pat. Nos. 5,672,592; 5,795,877; 5,804,602; 5,824,662; 5,863,536; 5,977,090; 5,981,209; 6,011,021; 6,017,903; 6,025,344; 6,025,345; 6,046,180; and 6,228,888; allowed U.S. Patent Application No. 09/228,391, for which the issue fee has been paid; International Publication Nos. WO 00/01668 and WO 00/38785; a U.S. Provisional Application filed on Jan. 17, 2001; and other references generally known in the art. The present inventors hereby incorporate by reference, as though set forth herein in full, the entire contents of the aforementioned patents, patent applications, and publications, particularly their discussions, figures and data regarding the effectiveness of NAALADase inhibitors in inhibiting angiogenesis, in effecting TGF-β activity, in diagnosing diseases, and in treating ischemia, spinal cord injury, demyelinating diseases, Parkinson's disease, ALS, alcohol dependence, nicotine dependence, cocaine dependence, prostate disease, cancer, diabetic neuropathy, pain, schizophrenia, anxiety, anxiety disorder, and memory impairment. The present inventors have discovered that the inventive compounds are effective NAALADase inhibitors. Thus, the inventive compounds are expected to have the same uses as the NAALADase inhibitors disclosed in the patents, patent applications, and publications that are incorporated by reference.

PHARMACEUTICAL COMPOSITIONS OF THE PRESENT INVENTION

The present invention also relates to a pharmaceutical composition comprising:

(i) an effective amount of a compound of formula I; and (ii) a pharmaceutically acceptable carrier.

Preferred compounds of formula I are set forth above.

Preferably, the compound of formula I is present in an effective amount for inhibiting NAALADase enzyme activity, treating glutamate abnormalities, effecting neuronal activity, treating diabetic neuropathy, pain, prostate diseases, and cancers, inhibiting angiogenesis, and treating TGF-β abnormalities, compulsive disorders, and glaucoma.

Route of Administration

In the inventive methods, the compounds will generally be administered to a patient in the form of a pharmaceutical formulation. Such formulation preferably includes, in addition to the active agent, a physiologically acceptable carrier and/or diluent. The compounds may be administered by any means known to an ordinarily skilled artisan. For example, the compounds may be administered orally, parenterally, by inhalation spray, topically, rectally, nasally, buccally, vaginally, or via an implanted reservoir in dosage formulations containing conventional non-toxic pharmaceutically acceptable carriers, adjuvants, and vehicles. The term "parenteral" as used herein includes subcutaneous, intravenous, intramuscular, intraperitoneal, intrathecal, intraventricular, intrasternal, intracranial, or intraosseous injection and infusion techniques. The exact administration protocol will vary depending upon various factors including the age, body weight, general health, sex and diet of the patient; the determination of specific administration procedures would be routine to an ordinarily skilled artisan.

To be effective therapeutically as central nervous system targets, the compounds should readily penetrate the blood-brain barrier when peripherally administered. Compounds that cannot penetrate the blood-brain barrier can be effectively administered by an intraventricular route or by other methods recognized in the art. See, e.g., U.S. Pat. Nos. 5,846,565; 5,651,986; and 5,626,862.

Dosage

The compounds and compositions of the present invention may be administered by a single dose, multiple discrete doses, or continuous infusion. The compounds are well suited to continuous infusion. Pump means, particularly subcutaneous pump means, are preferred for continuous infusion.

Dose levels on the order of about 0.001 to about 10,000 mg/kg of the active ingredient compound are useful in the treatment of the above conditions, with preferred levels being about 0.1 to about 1,000 mg/kg, and more preferred levels being about 1 to about 100 mg/kg. The specific dose level for any particular patient will vary depending upon a variety of factors, including the activity and the possible toxicity of the specific compound employed; the age, body weight, general health, sex, and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

Administration Regimen

For the methods of the present invention, any administration regimen well known to an ordinarily skilled artisan for regulating the timing and sequence of drug delivery can be used and repeated as necessary to effect treatment. Such regimen may include pretreatment and/or co-administration with additional therapeutic agents.

Co-administration with Other Treatments

The compounds and compositions of the present invention may be used alone or in combination with one or more additional agent(s) for simultaneous, separate, or sequential use.

The additional agent(s) may be any therapeutic agent(s) known to an ordinarily skilled artisan, including without limitation: one or more compound(s) of formula I; steroids, for example, hydrocortisomes such as methylprednisolone; anti-inflammatory or anti-immune drugs, such as methotrexate, azathioprine, cyclophospharnide or cyclosporin A; interferon-β; antibodies, such as anti-CD4 antibodies; agents which can reduce the risk of a second ischemic event, such as ticlopidine; chemotherapeutic agents; immunotherapeutic compositions; electromagnetic radiosensitizers; and morphine.

The compounds of the present invention can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of a compound of the present invention, as well as one or more pharmaceutical excipients, such as wetting, emulsifying, and pH buffering agents.

Preparation of Compounds

The compounds of the present invention can be readily prepared by standard techniques of organic chemistry, utilizing the general synthetic pathways depicted below in Schemes I, II, and III. Precursor compounds may be purchased from commercial sources or prepared by methods known in the art.

SCHEME I

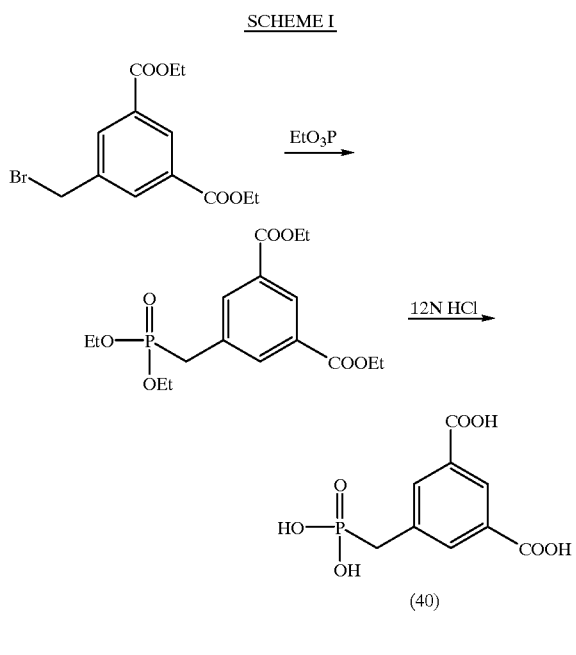

SCHEME II

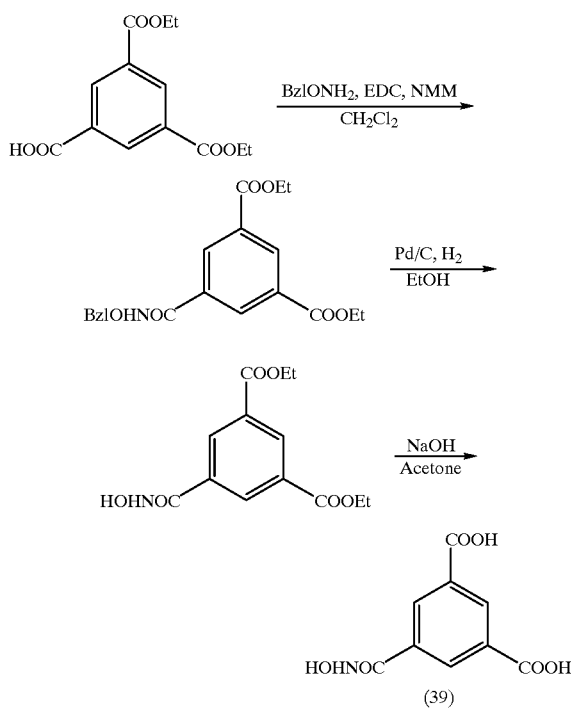

SCHEME III

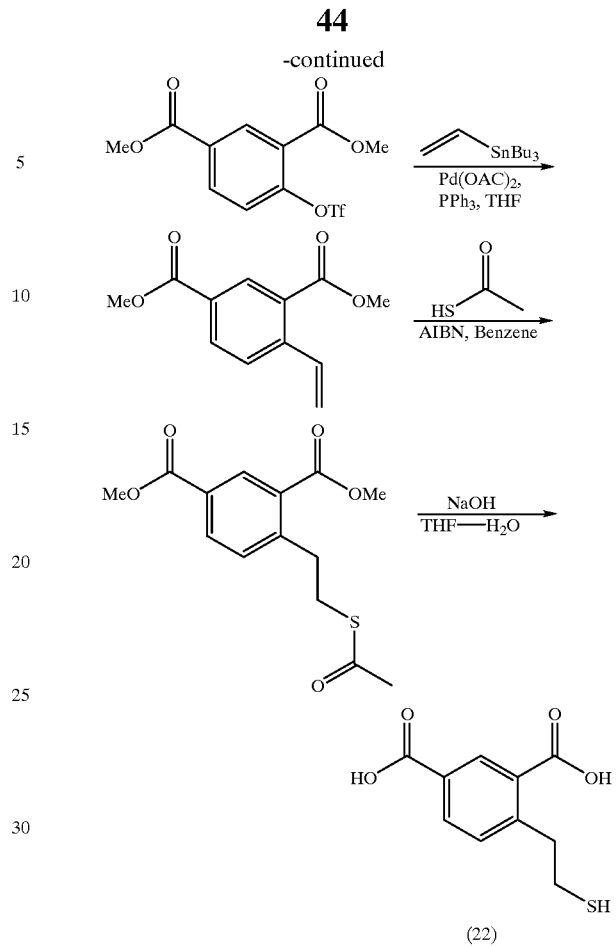

EXAMPLES

The following examples are illustrative of the present invention and are not intended to be limitation thereon. Unless otherwise indicated, all percentages are based upon 100% by weight of the final composition.

Example 1

Preparation of 5-phosphonomethyl-1,3-benzenedicarboxylic Acid (Scheme L Compound 40)

Preparation of diethyl-5-[(diethoxyphosphinyl)methyl]-1,3-benzenedicarboxylate

A solution of 5-bromomethyl-1,3-benzenedicarboxylate (Collman et al., *J. Am. Chem. Soc.*, 116(14) (1994) 6245–6251; 0.315 g, 1.0 mmol) in triethylphosphite (3.0 mL) was heated at 15° C. for 5 hours. The solvent was removed under reduced pressure and the residual oil was purified by chromatography to give 0.248 g of colorless oil (67% yield).

$^1$HNMR: (CDCl$_3$) δ 1.28 (t, 3H), 1.42 (t, 3H), 3.26 (d, 2H), 4.06 (q, 2H), 4.41 (q, 2H), 8.17 (s, 2H), 8.58 (s, 1H).

TLC: R$_f$ 0.10 (EtOAc/Hexanes 1/1).

Preparation of 5-phosphonomethyl-1 3-benzenedicarboxylic acid (40)

A solution of diethyl 5-[(diethoxyphosphinyl)methyl]-1,3-benzenedicarboxylate (0.186 g, 0.5 mmol) in 12 N HCl (2.5 mL) was heated at 100° C. for 24 hours. The resulting precipitate was washed with water and dried under vacuum to give 0.057 g of white powder (41% yield).

$^1$HNMR: (D$_2$O) δ 3.11 (d, 2H), 7.93 (s, 2H), 8.19 (s, 1H).

TLC: R$_f$ 0.20 (EtOAc/Hexanes 1/1).

Elemental Analysis:

Calculated for C$_9$H$_7$O$_7$P·H$_2$O: C, 38.86; H, 3.99.

Found: C, 38.74; H, 4.08

Example 2
Preparation of 5-[-(hydroxyamino)carbonyl]-1,3-benzenedicarboxylic Acid (Scheme II Compound 39)
Preparation of diethyl 5-[[(phenylmethoxy)amino]carbonyl]-1,3-benzenedicarboxylate To a solution of diethyl 1,3,5-benzenetricarboxylate (3.192 g, 20 mol) and O-benzylhydroxyamine hydrochloride (4.789 g, 19 mmol) in 40 mL were added N-methylmorpholine (2.2 mL, 20 mmol) and EDC (3.834 g, 20 mmol) at 0° C., and the mixture was stirred at room temperature for 20 hours. The solvent was removed by evaporator and the residue was dissolved in EtOAc (150 mL). The organic solution was washed with 1 N HCL (150 mL), washed with saturated aqueous $NaHCO_3$ (50 mL), dried over $Na_2SO_4$, and concentrated to give white solid. This material was recrystallized from EtOAc to give 4.154 g of white powder (59% yield).

$^1$H NMR: ($CDCl_3$) δ 1.41 (t, 6H), 4.40 (q, 4H), 5.05 (s, 2H), 7.3–7.5 (m, 5H), 8.52 (s, 2H), 8.76 (s, 1H), 9.1 (br, 1H).

TLC: $R_f$ 0.62 (EtOAc/Hexanes 1/1).

Preparation of diethyl 5-[(hydroxyamino)carbonyl]-1,3-benzenedicarboxylate

To a solution of diethyl 5-[[(phenylmethoxy)amino]-carbonyl]-1,3-benzenedicarboxylate (0.742 g, 2.0 mmol) in ethanol (10 mL) was added a suspension of Pd/C in ethanol (5 mL), and the mixture was shaken under hydrogen (50 psi) for 20 hours. The catalyst was removed by filtration through a pad of celite and the filtrate was concentrated to give white powder. This material was washed with ethanol (10 mL×2) and dried under vacuum to give 0.380 g of white powder (67% yield).

$^1$H NMR: ($CD_3OD$) 6 1.44 (t, 6H), 4.45 (q, 4H), 8.60 (s, 2H), 8.72 (s, 1H).

TLC: $R_f$ 0.20 (EtOAc/Hexanes 1/1).

Preparation of 5-[(hydroxyamino)carbonyl]-1,3-benzenedicarboxylic Acid (39)

To a solution of diethyl 5-[(hydroxyamino)carbonyl]-1,3-benzenedicarboxylate (0.281 g, 1.0 mmol) in acetone (5 mL) was added 1.0 N NaOH (5 mL) at room temperature, and the mixture was stirred at room temperature for 2 hours. The solvent was removed under reduced pressure and the residue was taken up with 1 N HCl (15 nL) to give white precipitate. This material was dried under vacuum to give 0.096 g of white solid (43% yield).

$^1$H NMR: ($D_2O$) δ 8.52 (s, 2H), 8.76 (s, 1H).

Elemental Analysis:

Calculated for $C_9H_7NO_6H_2O$: C, 44.45; H, 3.73; N, 5.76. Found: C, 44.47; H, 3.78; N, 5.74.

Example 3
Preparation of 4-(2-mercaptoethyl)-1,3-benzenedicarboxylic acid (Scheme III, Compound 22)
Preparation of dimethyl 4-trifluoromethanesulfonyloxy-1.3-benzenedicarboxylate To a solution of dimethyl 4-hydroxy-isophthalate (0.850 g, 4.04 mmol) in $CH_2Cl_2$ (15 mL) were added triethylamine (0.6 mL, 4.3 mmol) and triflic anhydride (0.8 mL, 4.76 mmol) at 0° C., and the mixture was stirred at 0° C. for 18 hours. The solvent was evaporated and the residue was diluted with ether (30 mL). The organic solution was washed with 1 N HCl (30 mL×3), dried over $MgSO_4$, and concentrated to give 1.30 g of dark yellow oil (93% yield).

$^1$H NMR: ($CDCl_3$) δ 3.97 (s, 3H), 4.00 (s, 3H), 7.4 (d, 1H), 8.3 (d, 1H), 8.74 (s, 1H).

Preparation of dimethl 4-ethenyl-1,3-benzenedicarboxylate

To a solution of dimethyl 4-trifluoromethanesulfonyl-oxy-1,3-benzenedicarboxylate (1.5 g, 4.38 mmol) in dioxane (50 mL) were added $Pd(PPh_3)_4$ (510 mg, 0.44 mmol), lithium chloride (1.3 g, 30.7 nunol) and tributyl(vinyl)tin (1.5 mL, 5.13 mmol) at room temperature. The mixture was heated at 100° C. for 5 hours. The reaction mixture was filtered and the filtrate was concentrated and passed through a column of silica gel (Hexanes/EtOAc=10: 1) to give 1.1 g of colorless oil (84% yield).

$^1$H NMR: ($CDCl_3$) δ 3.92 (s, 3H), 3.93 (s, 3H), 5.45 (d, 1H), 5.73 (d, 1H), 7.49 (m, 1H), 7.66 (d, 1H), 8.13 (d, 1H), 8.53 (s, 1H).

Preparation of dimethyl 4-[2-(acetylthio)ethyl]-1,3-benzenedicarboxylate

To a degassed solution of dimethyl 4-ethenyl-1,3-benzenedicarboxylate (415 mg, 1.88 mmol) in benzene (6 mL) were added AIBN (33 mg, 0.21 mmol) and thioacetic acid (0.27 mL, 3.78 mmol), and the mixture was refluxed for 5 hours. The reaction mixture was diluted with aqueous $NaHCO_3$ solution (15 mL) and extracted with EtOAc (15 mL). The organic layer was dried over $MgSO_4$ and concentrated. The residual material was purified by silica gel chromatography (hexanes/EtOAc=10:1) to give 0.150 g of colorless oil (27% yield).

$^1$H NMR: ($CDCl_3$) δ 2.32 (s, 3H), 3.16 (t, 2H), 3.28 (t, 2H), 3.94 (s, 6H), 7.42 (d, 1H), 8.09 (d, 1H), 8.58 (s, 1H).

Preparation of 4-(2-mercaptoethyl)-1,3-benzenedicarboxylic acid (22)

To a degassed solution of dimethyl 4-[2-(acetylthio)ethyl]-1,3-benzenedicarboxylate (0.130 g, 0.44 mmol) in THF (5 mL) was added a degassed solution of 5 N NaOH (5 mL). The reaction mixture was stirred under nitrogen overnight. The reaction mixture was diluted with $H_2O$ (10 mL) and extracted with EtOAC (10 mL). The organic layer was dried over $MgSO_4$ and concentrated to give 0.045 g of white solid (45% yield).

$^1$H NMR: (DMSO) δ 2.67 (t, 2H), 3.21 (t, 2H), 7.37 (d, 1H), 7.98 (d, 1H), 8.46 (s, 1H)

$^{13}$C NMR: (DMSO) δ 26.64, 40.60, 130.87, 132.05, 133.46, 133.81, 134.13, 148.53, 169.22, 170.20

Elemental Analysis:

Calculated for $C_{10}H_{10}SO_4 \cdot 0.3$ EtOAc: C, 53.24; H, 4.95; S, 12.69. Found: C, 53.37; H, 4.87; S, 12.84.

MS(FAB): 225

Example 4
In Vitro Inhibition of NAALADase Activity

Various compounds of formula I were tested for in vitro inhibition of NAALADase activity, and the results are provided below in Table IV.

TABLE IV

| Compound | $K_i$ (nM) |
| --- | --- |
| 4-[4-(2,4-dicarboxybenzoyl)phenoxy]-1,2-benzenedicarboxylic acid (13) | 1170 |
| 2-[(4-carboxyphenyl)sulfonyl]-1,4-benzenedicarboxylic acid (1) | 2370 |
| 2-[(2,5-dicarboxyphenyl)sulfonyl]-1,4-benzenedicarboxylic acid (2) | 1870 |
| 4-[(2-carboxyphenyl)thio]-1,3-benzenedicarboxylic acid (18) | 3980 |
| 2-[(2-carboxyphenyl)thio]-1,4-benzenedicarboxylic acid (4) | 572 |
| 4-[3-[[3-(2,4-dicarboxyphenoxy)-propyl]-dithio]propoxy]-1,3-benzenedicarboxylic acid (19) | 3750 |
| 5-(3-mercaptopropoxy)-1,3-benzenedicarboxylic acid (36) | 3300 |
| 5-(2-mercaptoethoxy)-1,3-benzenedicarboxylic acid (38) | 14500 |
| 5-[(hydroxyamino)-carbonyl]-1,3-benzenedicarboxylic acid (39) | 1000 |
| 5-phosphono-1,3-benzenedicarboxylic acid (40) | 14000 |
| 5-mercaptomethyl-1,3-benzenedicarboxylic acid (41) | 6500 |

TABLE IV-continued

| Compound | $K_i$ (nM) |
| --- | --- |
| 5-phosphonomethyl-1,3-benzenedicarboxylic acid (42) | 3100 |
| 5-[(carboxymethyl)amino]-1,3-benzenedicarboxylic acid (44) | 100000 |
| 5-[[(2-furanylmethyl)amino]methyl]-1,3-benzenedicarboxylic acid (45) | 50000 |
| 2-carboxymethyl-1,4-benzenedicarboxylic acid (9) | 9000 |
| 5-[2-(hydroxyamino)-2-oxoethyl]-1,3-benzenedicarboxylic acid (46) | 12000 |
| 4-(2-mercaptoethyl)-1,3-benzenedicarboxylic acid (22) | 116 |
| 5-(2-mercaptoethyl)-1,3-benzenedicarboxylic acid (47) | 5100 |

Protocol for Assaying In Vitro Inhibition of NAALADase Activity

The following were combined in each assay tube: 100 μL of 10 mM $CoCl_2$, 250 μL of 200 mM Tris chloride, 100 μL tissue, 100 μL of 10 mM NAALADase inhibitor in Bakers $H_2O$, and Bakers $H_2O$ to make a total volume of 950 μL. Each tube was then incubated for 10 minutes in a 37° C. water bath. 50 μL of 3-H-NAAG was then added to each assay tube and incubated for an additional 15 minutes in a 37° C. water bath. The assay was stopped by adding 1.0 ml of 0.1 M sodium phosphate.

Glutamate released by the action of the NAALADase enzyme was separated from the assay solution using an anion exchange resin. The resin was equilibrated to 25° C., 2.0 ml of the resin was added to a Pasteur pipette pre-loaded with a single glass bead, and each column was washed twice with distilled $H_2O$. A column was placed over a scintillation vial and 200 μL of an assay sample was loaded onto the column. After draining, glutamate was eluted using two 1.0 ml washes of 1 M fornic acid. After addition of 10 ml of scintillation cocktail, each sample was counted for 2 minutes on a scintillation counter.

Example 5
In Vitro Assay on Ischemia

To examine the in vitro effect of the compounds of formula I on ischemia, cortical cell cultures were treated with various compounds of formula I during an ischemic insult utilizing potassium cyanide and 2-deoxyglucose, and for one hour thereafter (for experimental details, see Vornov et al., *J. Neurochem.*, Vol. 65, No. 4, pp. 1681–1691 (1995)). The results are provided below in Table V. Neuroprotective effect is expressed as $EC_{50}$, the concentration of the compound, which is required to cause a 50% reduction in glutamate toxicity following an ischemic insult.

TABLE V

| Compound | $EC_{50}$ (nM) |
| --- | --- |
| 4-[3-[[3-(2,4-dicarboxyphenoxy)-propyl]dithio]propoxy]-1,3-benzenedicarboxylic acid (19) | 2490 |
| 5-(3-mercaptopropoxy)-1,3-benzenedicarboxylic acid (36) | 1240 |
| 5-[(hydroxyamino)-carbonyl]-1,3-benzenedicarboxylic acid (39) | 473 |
| 5-mercaptomethyl-1,3-benzenedicarboxylic acid (41) | 172 |
| 4-(2-mercaptoethyl)-1,3-benzenedicarboxylic acid (22) | 60 |

Figure 2:
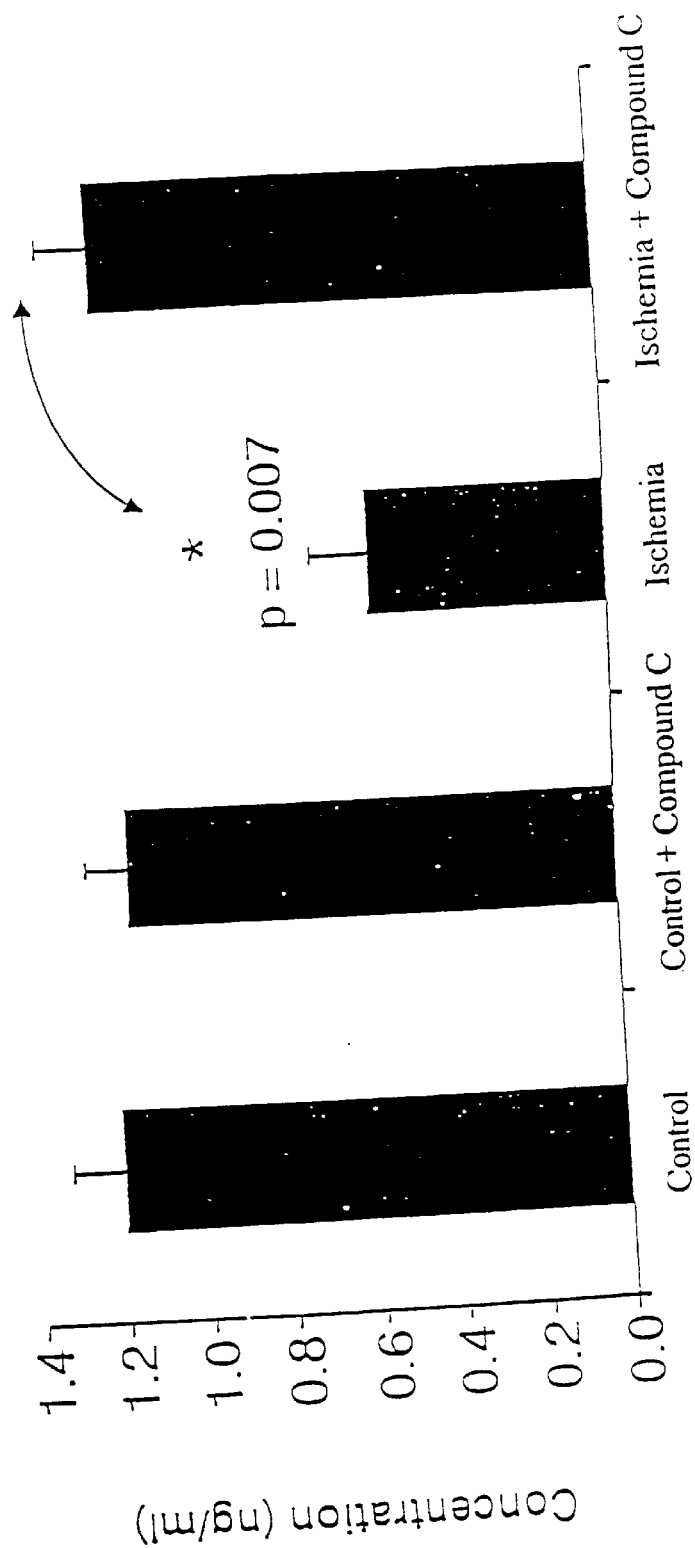
FIG. 2 is a bar graph showing the effect of Compound C on TGF-β2 concentrations in ischemic cell cultures.

Example 6
Effect of NAALADase Inhibition on TGF-β in In Vitro Ischemia Model A NAALADase inhibitor, Compound C, was added to ischemia cell cultures to determine its effect on TGF-β levels during stroke. The experimental data, set forth in FIGS. 1 and 2, show increased concentrations of TGF-β1 (FIG. 1) and TGF-β2 (FIG. 2) in ischemic cell cultures treated with Compound C. The results indicate that NAALADase inhibition promotes the release of endogenous TGF-β's from glial cells, which in turn provides neuroprotection for neighboring neurons.

Figure 3:
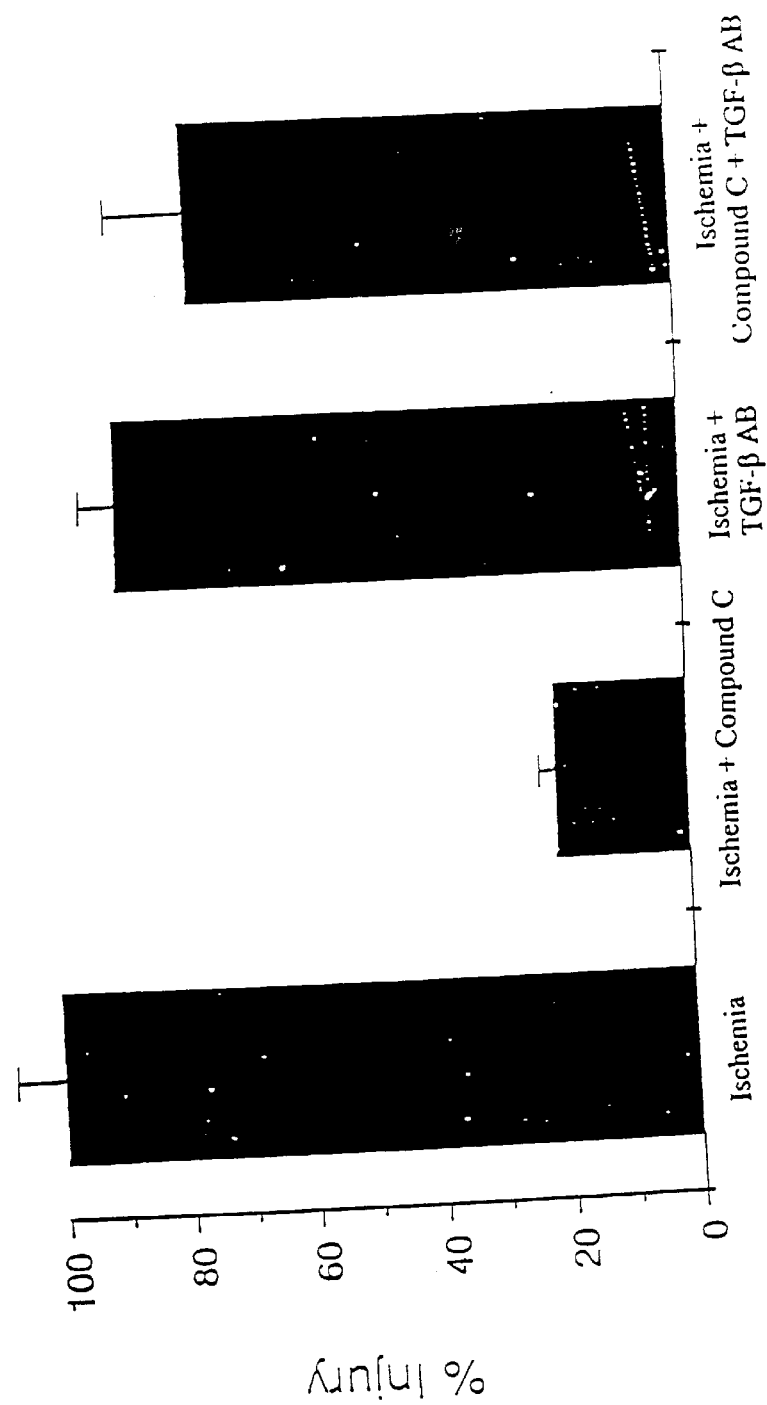
FIG. 3 is a bar graph showing the reversal of the neuroprotective effect of Compound C by TGF-β neutralizing antibodies in ischemic cell cultures.
Figure 4:
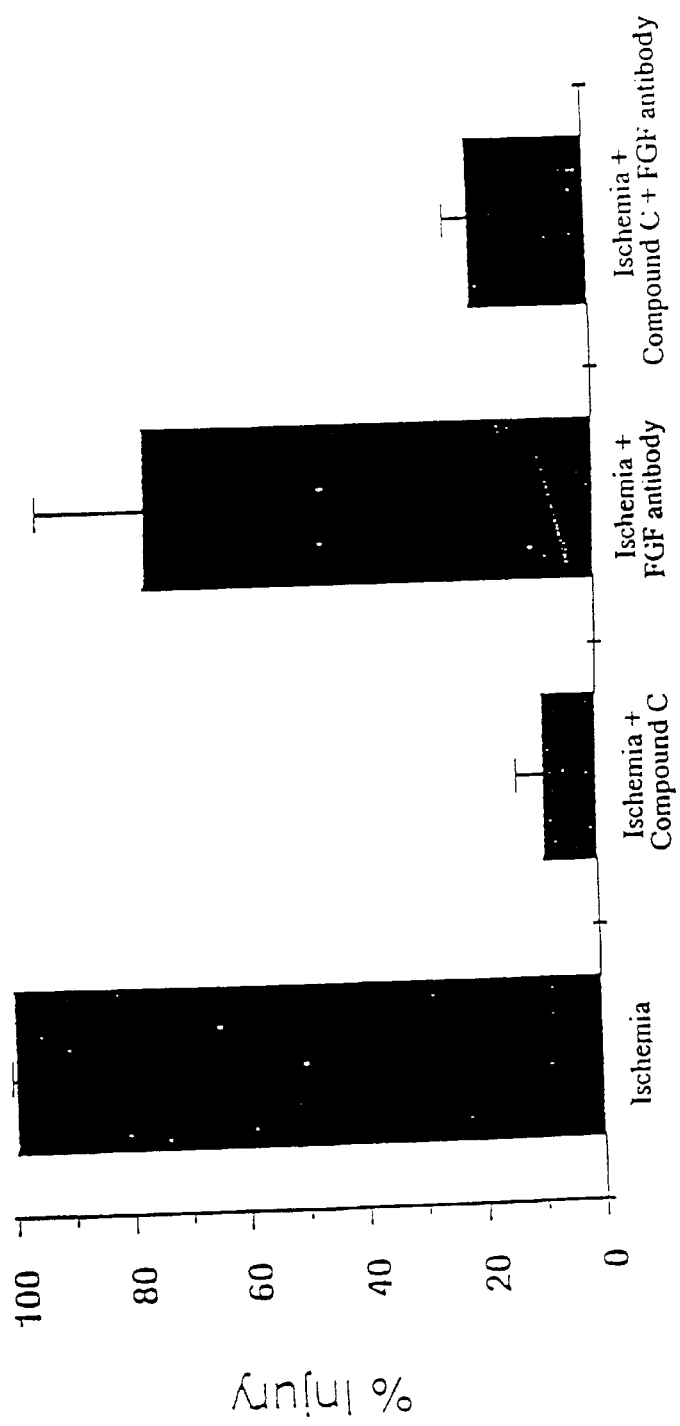
FIG. 4 is a bar graph showing the non-reversal of the neuroprotective effect of Compound C by FGF neutralizing antibodies in ischemic cell cultures

TGF-β neutralizing antibodies were then added to the ischemic cell cultures. FIG. 3 shows that the TGF-β neutralizing antibodies blocked the neuroprotective effect of Compound C in the in vitro ischemia model. By contrast, FIG. 4 shows that the addition of another growth factor antibody, FGF antibody, did not block the neuroprotective effect of Compound C. The results indicate that NAALADase inhibition specifically affects TGF-β levels during stroke.

Example 7
Effect of NAALADase Inhibition on TGF-β in In Vivo Ischemia Model

Figure 6:
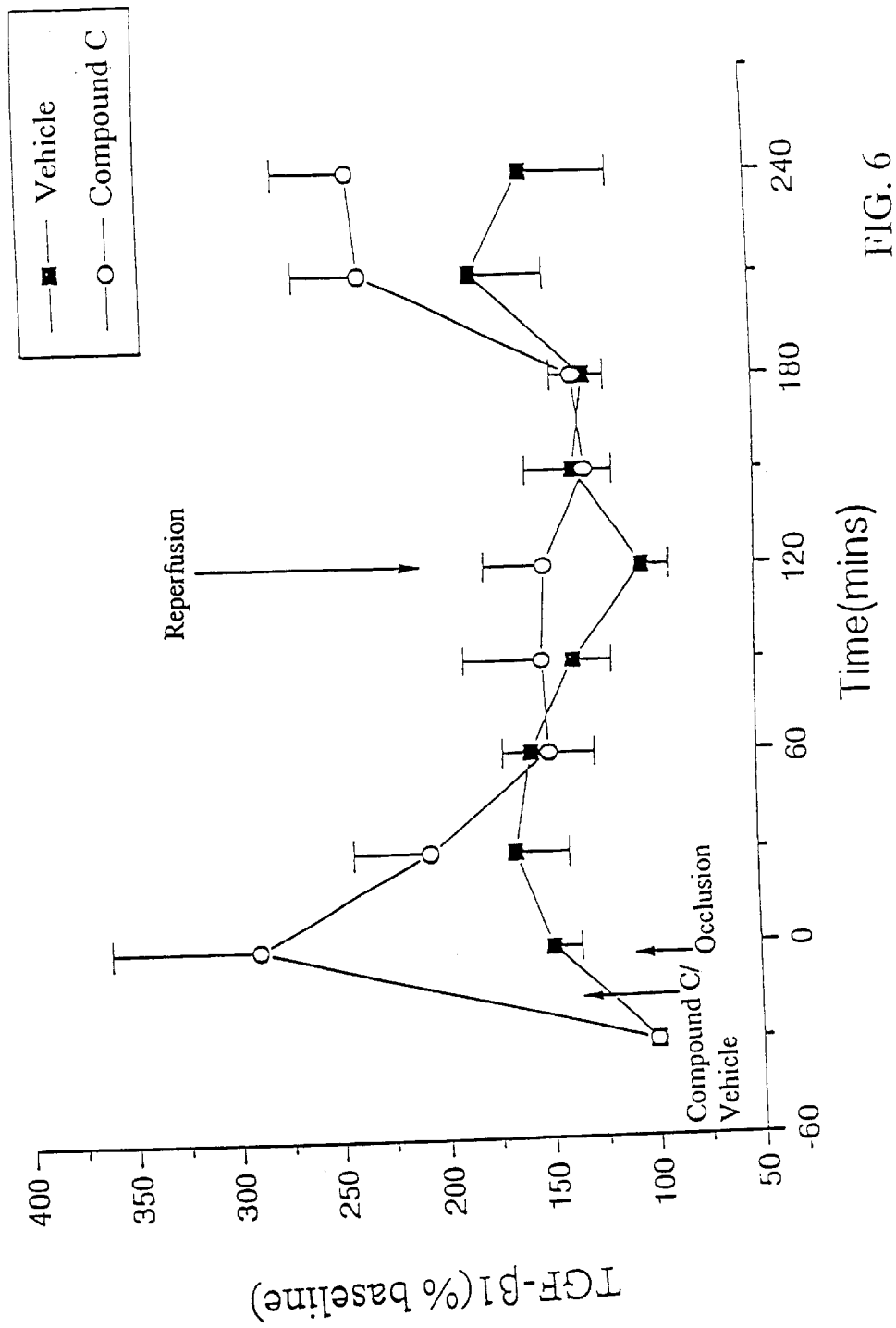
FIG. 6 is a bar graph showing the effect of Compound C on TGF-β1 levels during occlusion and reperfusion in rats subjected to MCAO.
Figure 7:
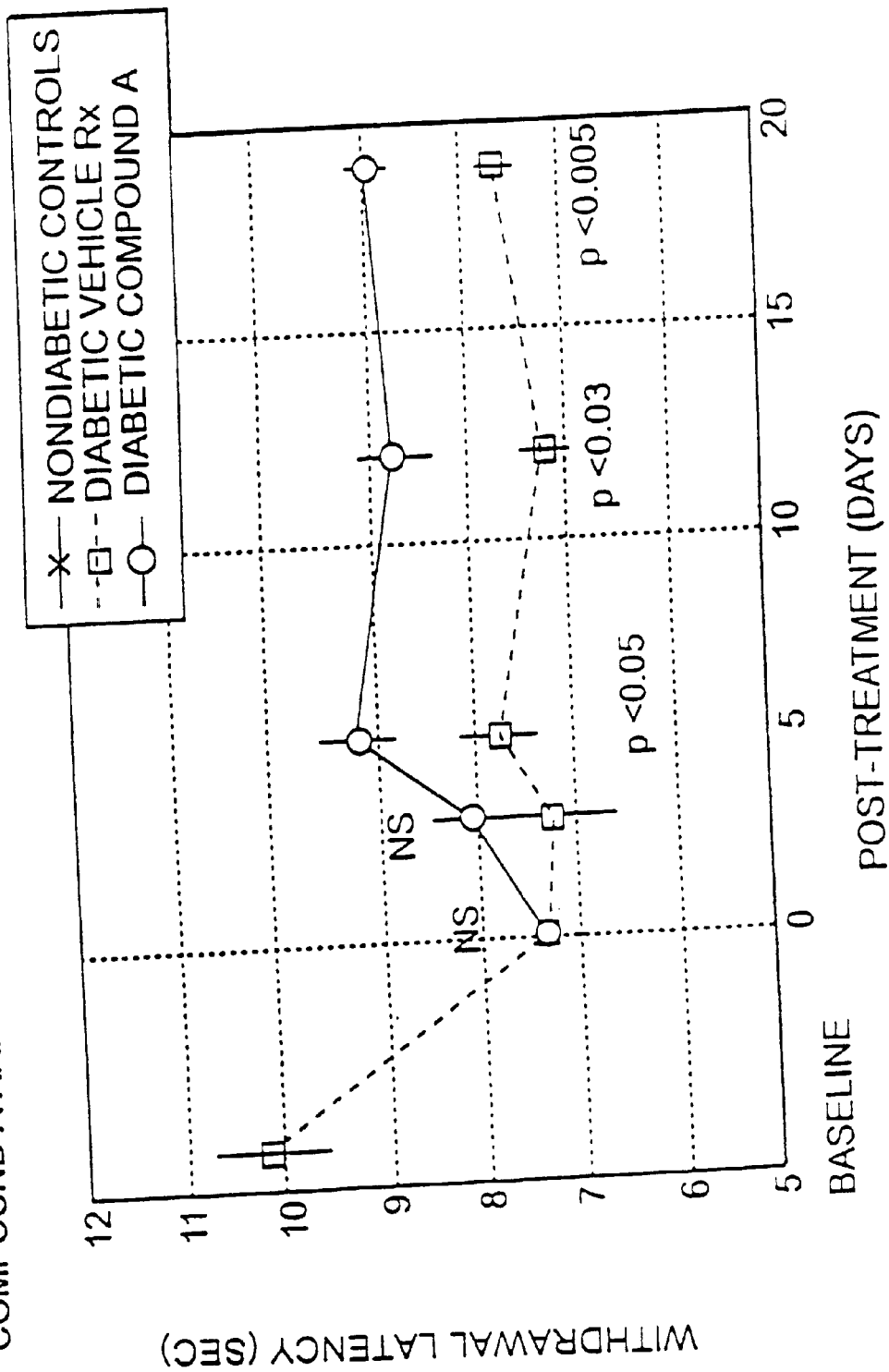
FIG. 7 is a graph plotting withdrawal latency of diabetic rats against the days following treatment with Compound A.
Figure 8:
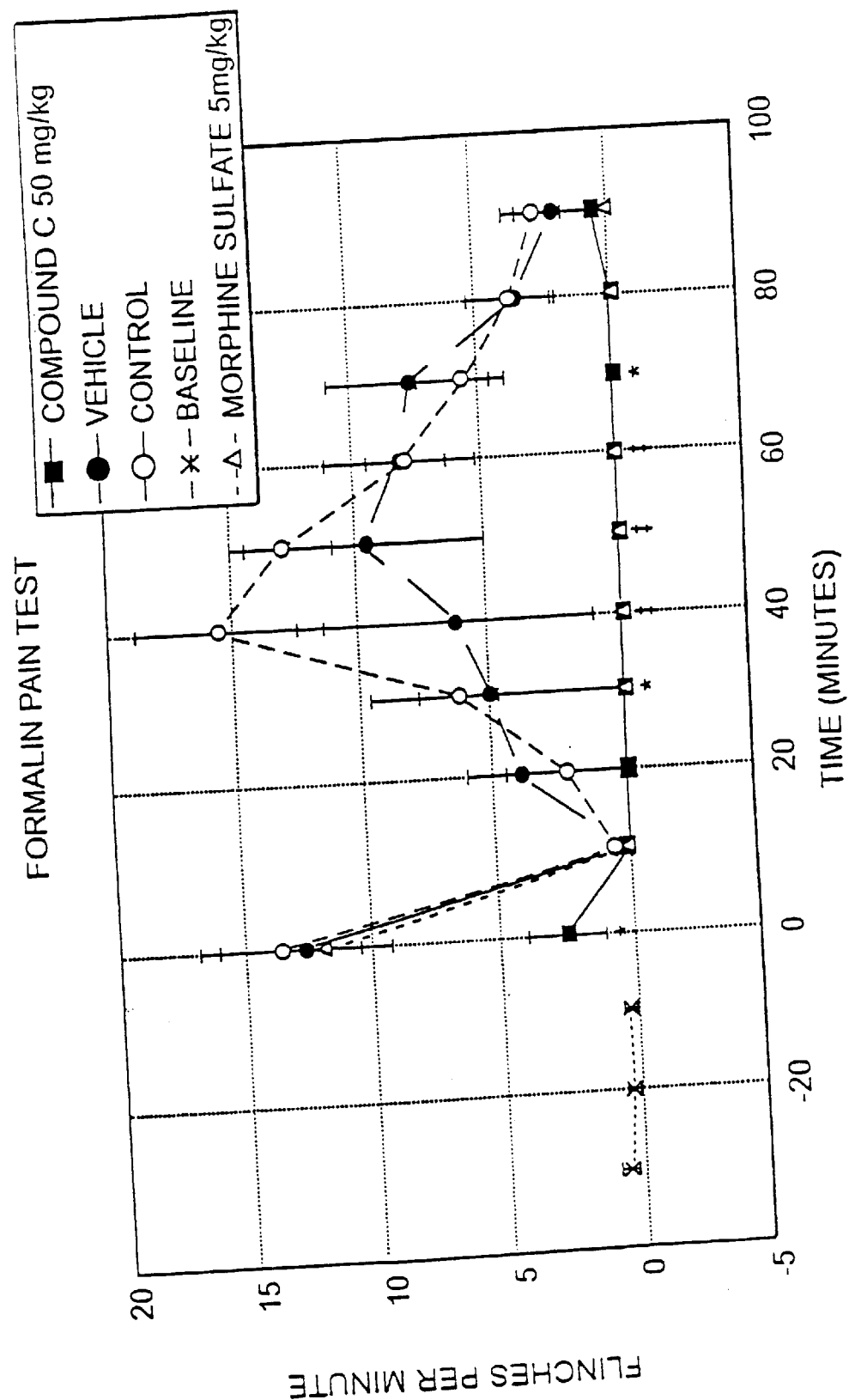
FIG. 8 is a graph plotting the formalin-induced flinching behavior of rats treated with a vehicle or Compound C against the time following treatment.
Figure 9:
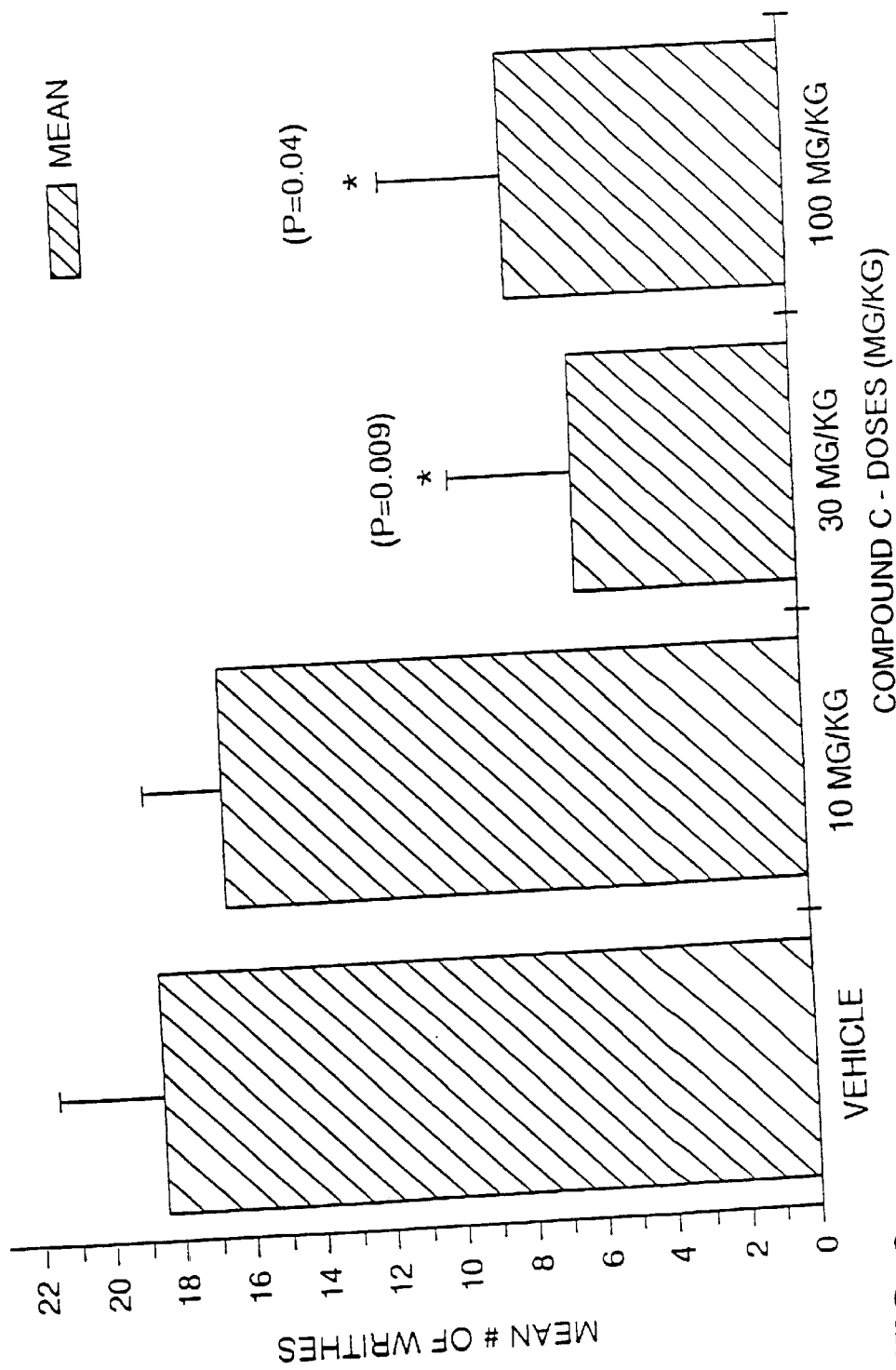
FIG. 9 is a bar graph plotting the acetic acid-induced writhing of rats treated with various doses of Compound C or a vehicle.
Figure 10:
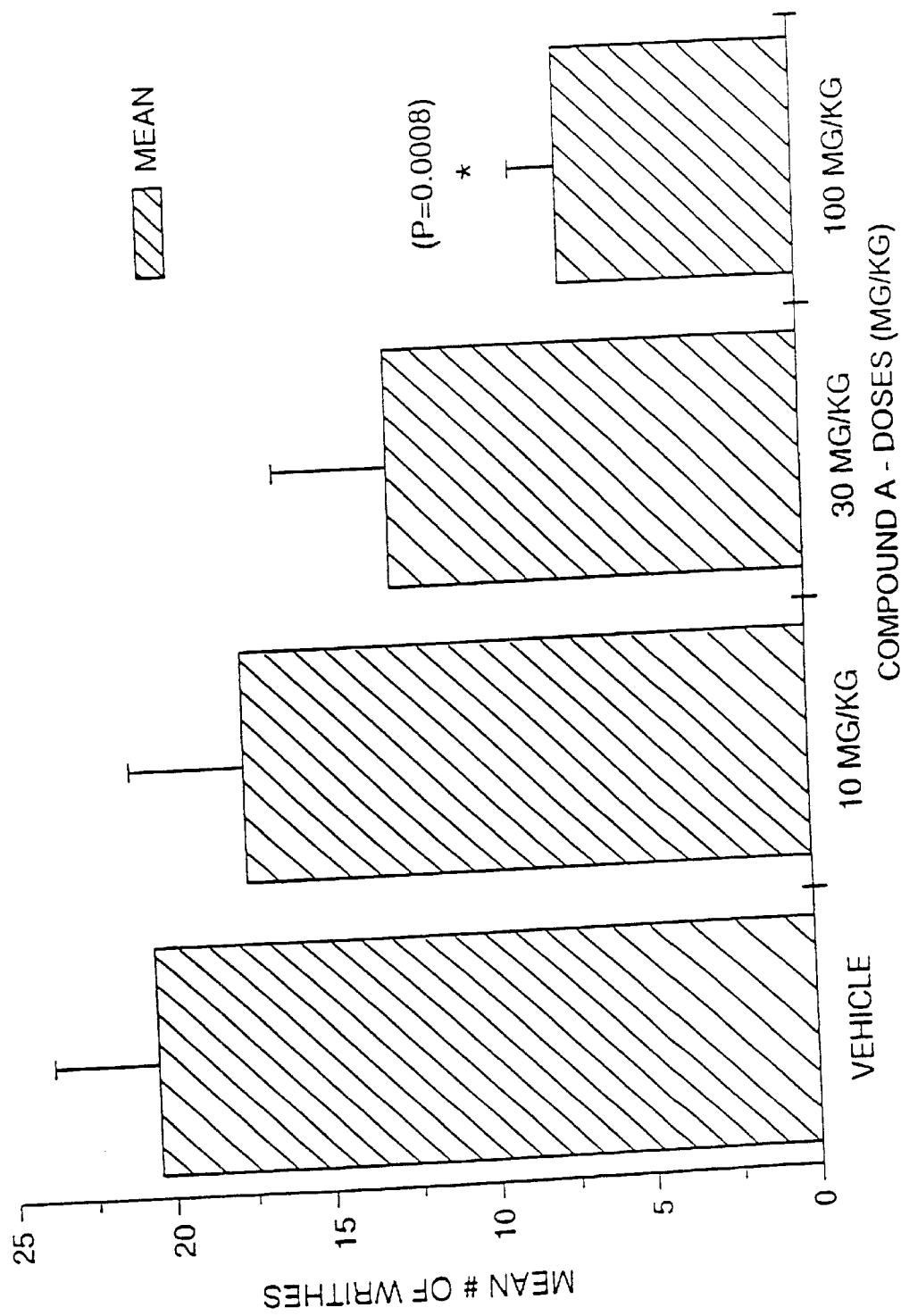
FIG. 10 is a bar graph plotting the acetic acid-induced writhing of rats treated with various doses of Compound A or a vehicle.
Figure 11:
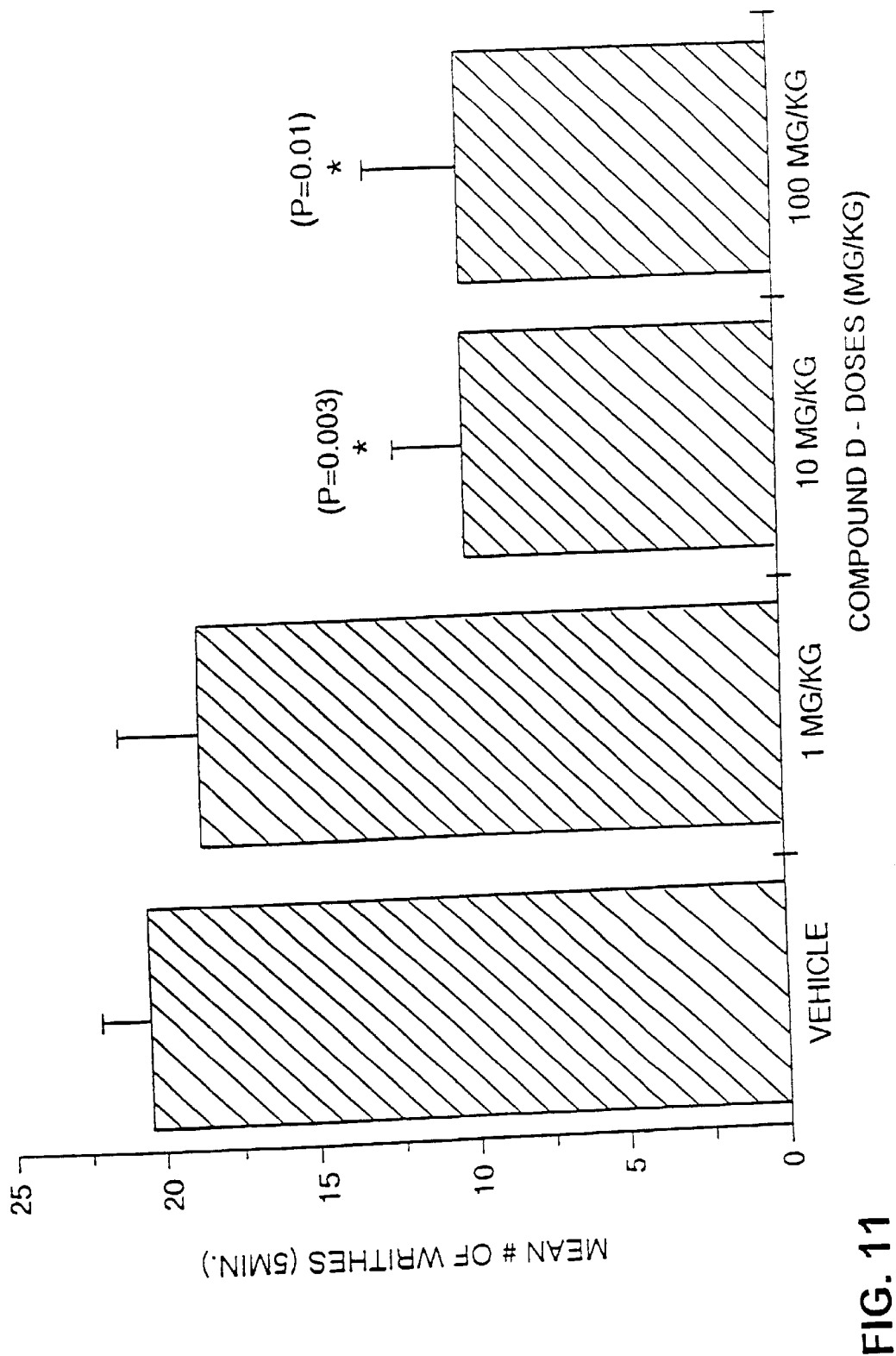
FIG. 11 is a bar graph plotting the acetic acid-induced writhing of rats treated with various doses of Compound D or a vehicle.
Figure 12:
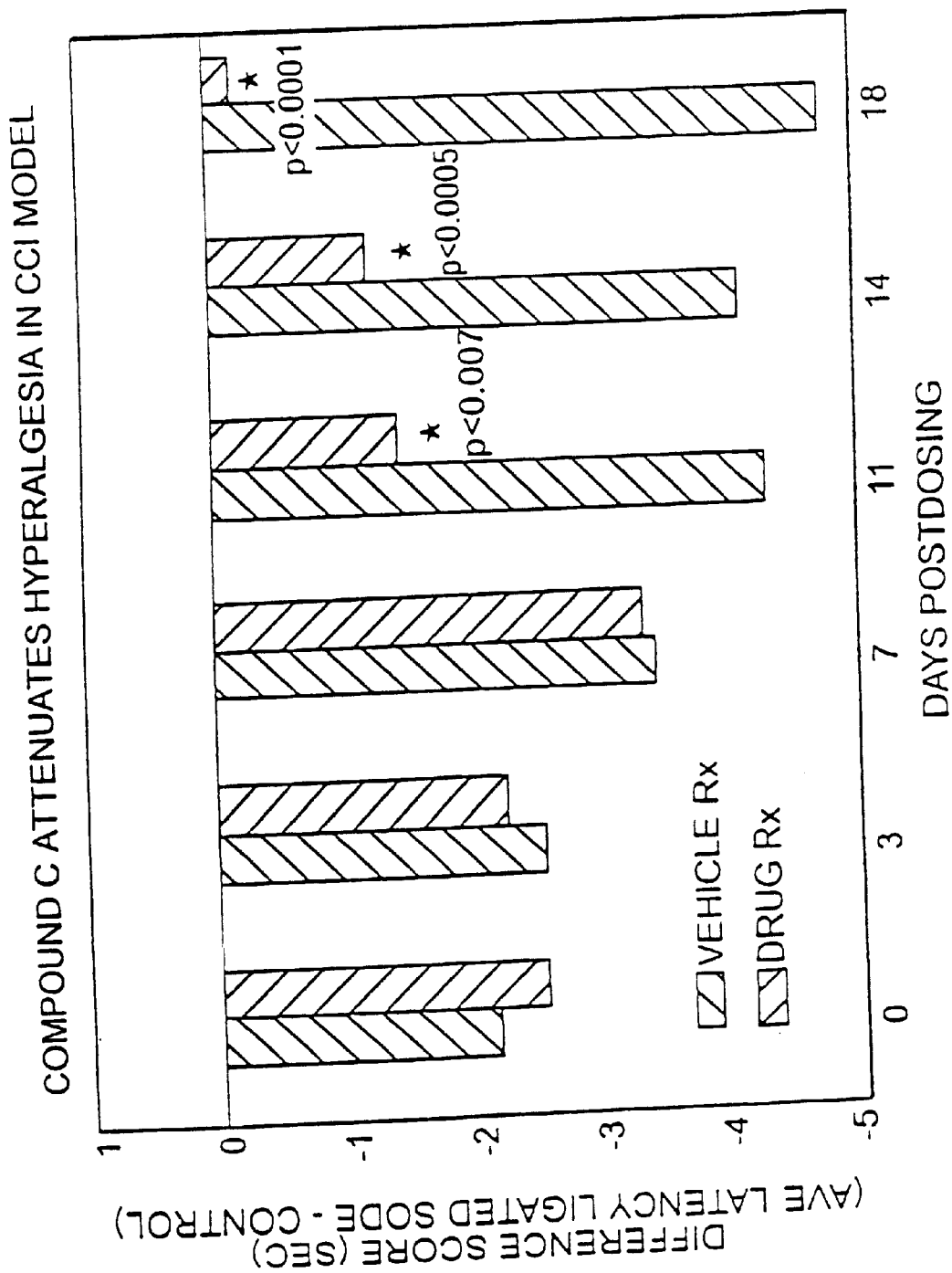
FIG. 12 is a bar graph plotting the chronic constrictive injury-induced hyperalgesia of rats treated with a vehicle or Compound C against the days after dosing.

The effect of TGF-β neutralizing antibodies on the neuroprotective effect of Compound C was also studied in rats following MCAO. FIG. 6 shows that treatment of MCAO rats with Compound C caused a significant rise in TGF-β1 levels during both occlusion and reperfusion, as assessed by microdialysis. The results indicate that NAALADase inhibition provides neuroprotection, at least in part, by regulating endogenous TGF-β's.

Figure 5:
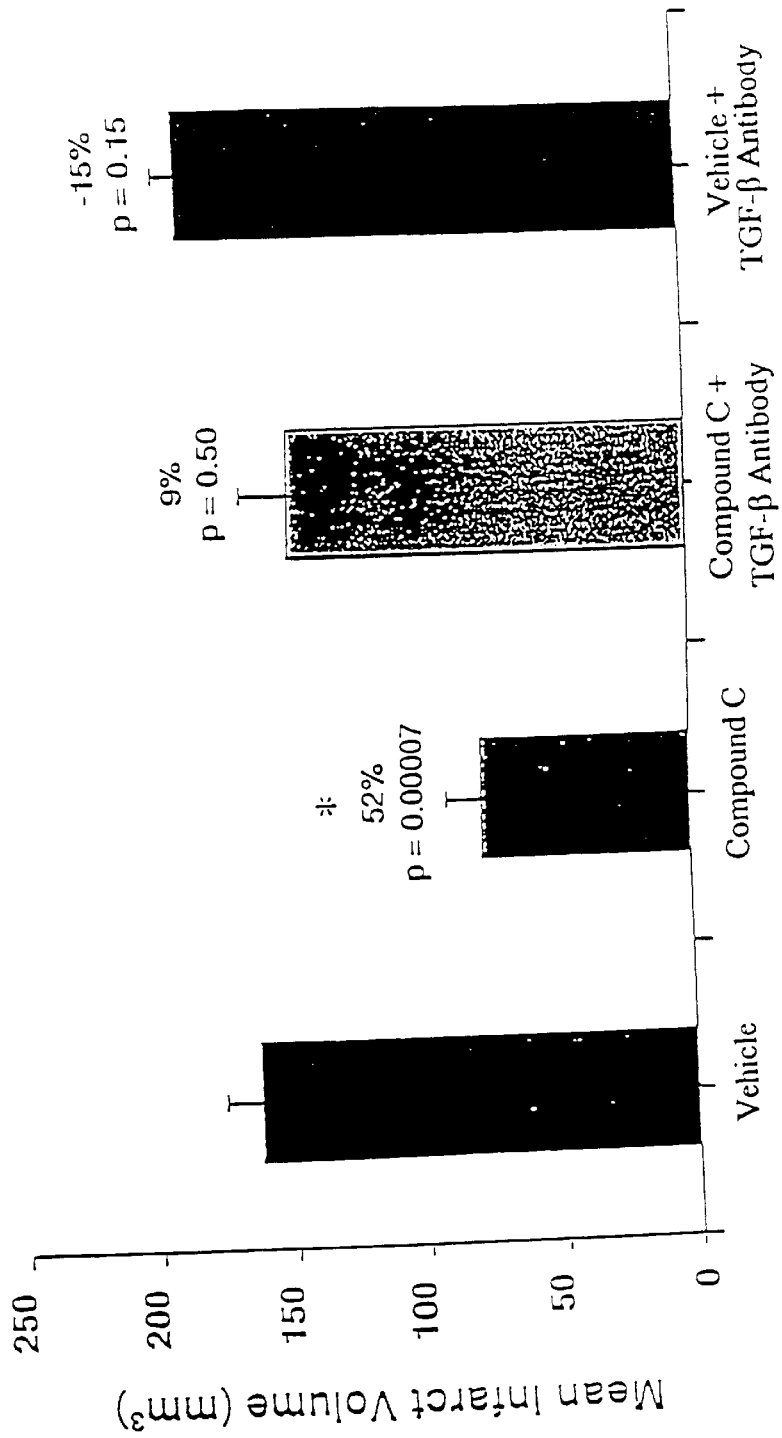
FIG. 5 is a bar graph showing the reversal of the neuroprotective effect of Compound C by TGF-β neutralizing antibodies in rats subjected to middle cerebral artery occlusion ("MCAO").

Additionally, FIG. 5 shows that TGF-β neutralizing antibodies significantly attenuated the neuroprotective effect of Compound C in vivo. One of ordinary skill in the art can appreciate that the regulation of TGF-β's by NAALADase inhibitors may have implications not only in stroke, but also in other diseases, disorders and conditions including, without limitation, neurological diseases, psychiatric diseases, demyelinating diseases, prostate cancer, inflammation, and angiogenesis.

Example 8
In Vivo Assay of NAALADase Inhibitors on Neuropathic Pain

Figure 13A:
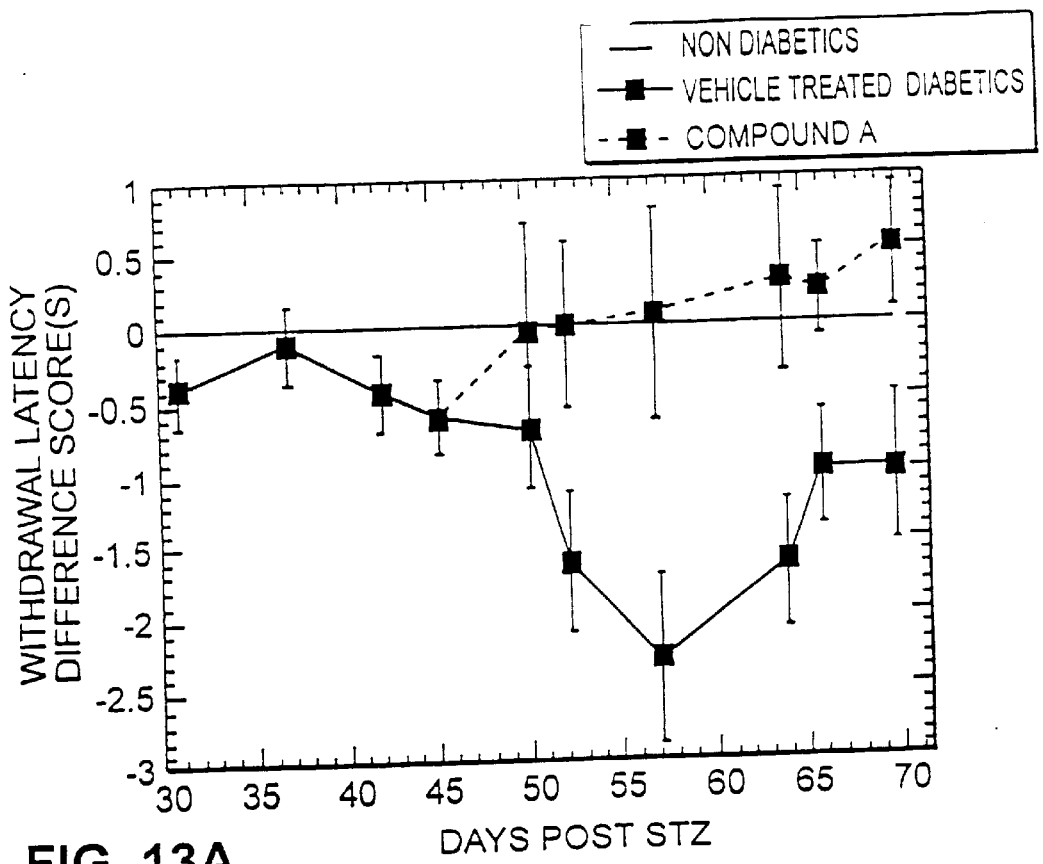
FIG. 13A is a bar graph plotting the withdrawal latency difference scores of non-diabetic rats and STZ-diabetic rats treated with a vehicle or Compound A, against the days following administration with STZ.
Figure 13B:
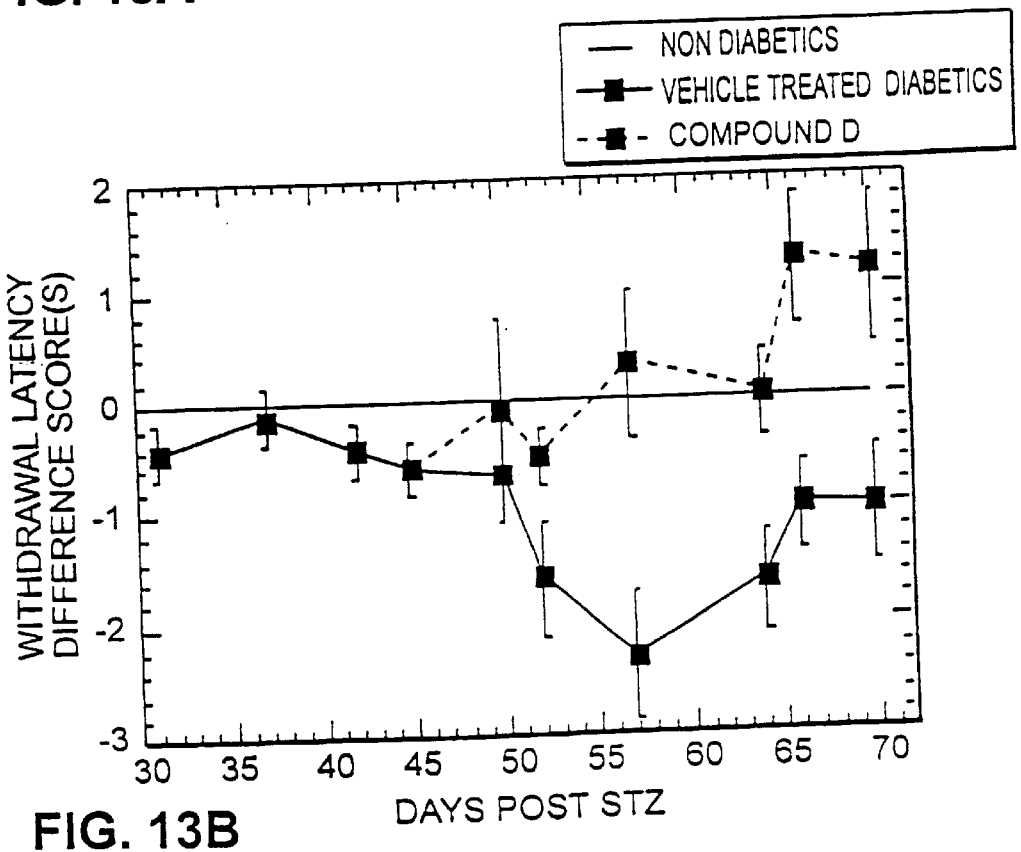
FIG. 13B is a bar graph plotting the withdrawal latency difference scores of non-diabetic rats and STZ-diabetic rats treated with a vehicle or Compound D, against the days following administration with STZ.

Male Sprague-Dawley rats (200–225 g) were rendered diabetic by intravenous administration of streptozotocin ("STZ", 70 mg/kg in phosphate buffered saline). Diabetic animals were divided into five groups: one group receiving Compound A (10 mg/kg or 1 mg/kg), Compound D (10 mg/kg or 1 mg/kg) or vehicle. Another group of animals (non-STZ treated) served as non-diabetic controls. Drug/vehicle treatment was started in diabetic animals 45 days post-STZ administration. STZ-induced diabetic rats were tested for sensitivity to a heat source as soon as blood glucose levels rose to 320 mg/dl or above (30 days post STZ). The rats were then acclimated to the Hargreaves apparatus and thermal nociception was monitored using an infrared heat source directed into the dorsal surface of the hindpaw, and the time taken for the animal to remove its paw noted to the nearest 0.1 seconds (for detailed method, see Hargreaves et al., *J. Biol. Chem.* (1988) 263(36):19392–7). The intensity of the beam source was adjusted such that the mean latency for control animals (non-STZ treated) was approximately 10 seconds. Each animal was tested 8 times and the mean difference score (between mean non-diabetic control latency and mean diabetic latency) are graphically presented in FIGS. 13A and 13B. Diabetic rats displayed a hyperalgesia (shorter response latency) compared to non-diabetic controls, starting 30 days post STZ treatment and progressively worsening in vehicle treated rats. This hyperalgesic response was completely reversed in diabetic rats receiving treatment with Compound D or A (10 mg/kg i.p.

daily). Thus, the results show that NAALADase inhibition attenuates neuropathic pain.

Example 9

In Vivo Assay of NAALADase Inhibitors on Neuropathic Pain Progression CCI Model

Sciatic nerve ligation, consisting of 4 ligatures tied loosely around the sciatic nerve at 1 mm intervals proximal to the nerve trifurcation, was performed on rats. Following sciatic nerve ligation, the rats exhibited a thermal hyperalgesia and allodynia. The rats were habituated to a Hargreaves apparatus. An infrared heat source was directed onto the dorsal surface of each rat's hindpaws and the time taken for the rat to withdraw its paws was noted. The difference in scores between the latency of the response for the paw on the operated side versus the paw on the unoperated control side was determined.

Compound C

Figure 14:
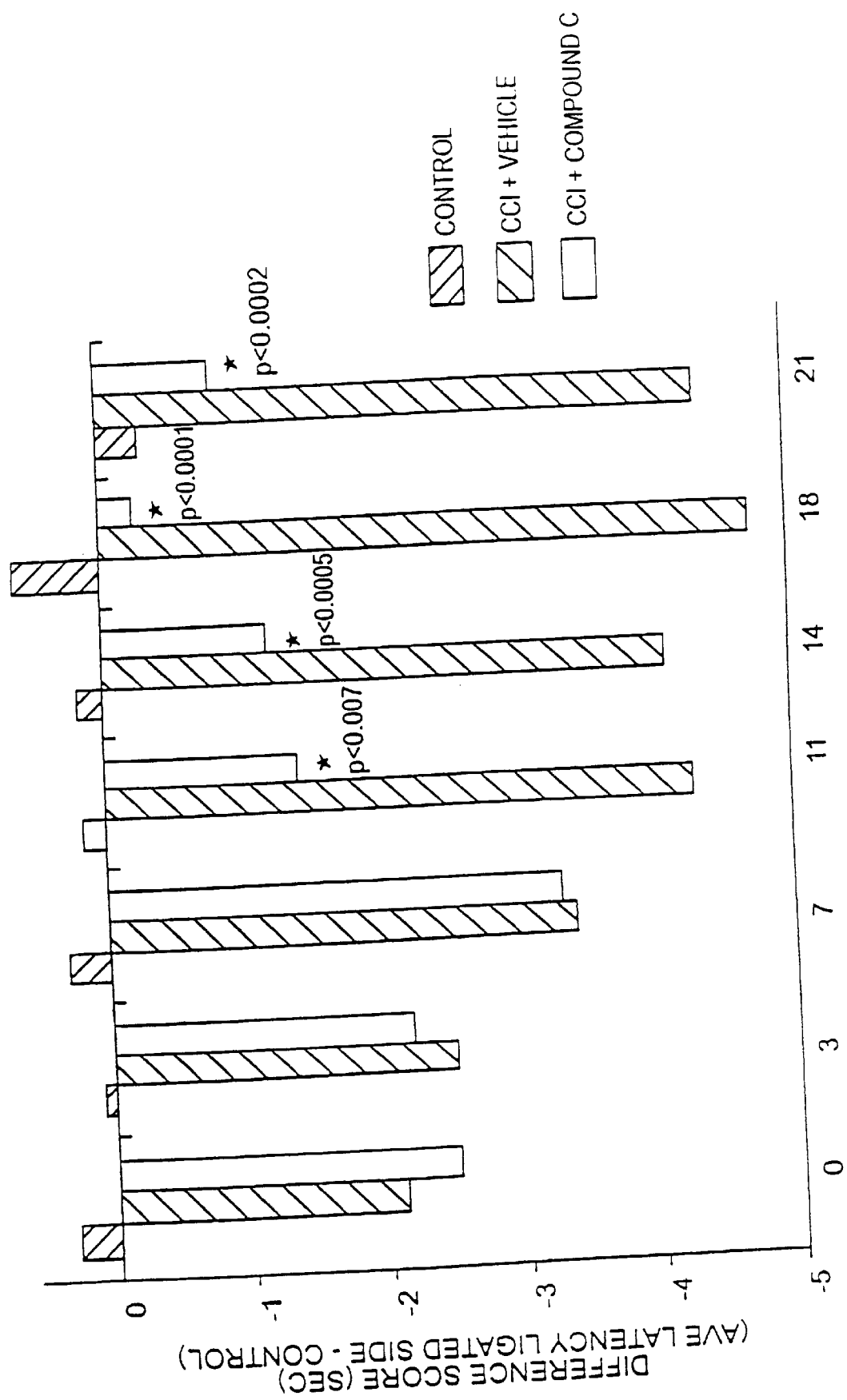
FIG. 14 is a bar graph plotting the withdrawal latency difference scores of normal (unoperated) rats and chronic constrictive injury-induced rats treated with a vehicle or Compound C, against the days following surgery.

Animals received Compound C (50 mg/kg i.p. daily) or vehicle, starting 10 days post surgery. Treatment with Compound C dramatically normalized the difference scores between the two paws compared to the continued hyperalgesic vehicle-treated controls. Normal (unoperated) rats had approximately equal latencies for both paws. This effect was significant starting at 11 days of drug treatment and persisted through to the end of the study (for 21 days of daily dosing). The difference scores are graphically presented in FIG. 14. The results show that NAALADase inhibition attenuates CCI-associated hyperalgesia.

Compounds D and A

Male BB/W rats (BRI, Mass) spontaneously develop a cell mediated autoimmune destruction of pancreatic B cells, resulting in onset of insulin-dependent (Type I) diabetes (Awata and Guberski et al., *Endocrinology* 1995 Dec; 136 (12):5731–5). These rats have been characterized and shown to demonstrate neuropathies with accompanying neural deficits such as fiber loss and degeneration, changes which are correlative with those seen in peripheral nerve of human diabetic patients (Yagihasi, *J. Peripher. Nerv. Syst.* 1997; 2(2):113–32). This renders them valuable for experimental trials of new compounds for future treatments of this major disorder. In the present study, Compound D and Compound A were examined for their ability to alter the progression of diabetic neuropathy. The rats received daily injection of Compound D or Compound A (10 mg/kg i.p.) or vehicle, starting at the onset of diabetes (hyperglycemia) and up to 6 months thereafter. Another group of non-diabetic rats also receiving vehicle were tested. All animals were continuously monitored for body weight, urine volume, blood sugar and glycated haemoglobin. In the first month of the study, all animals were tested for thermal nociception in a Hargreaves apparatus, weekly. After the first month this was done biweekly and then monthly. The testing consists of directing an infrared heat source onto the dorsal surface of the rat hindpaw and noting the time taken for the animal to remove its paw (for detailed method, see Hargreaves et al., *J. Biol. Chem.* 1988 Dec 25; 263 (36):19392–7). Each animal was tested 8 times and the mean withdrawal latency noted.

Figure 17:
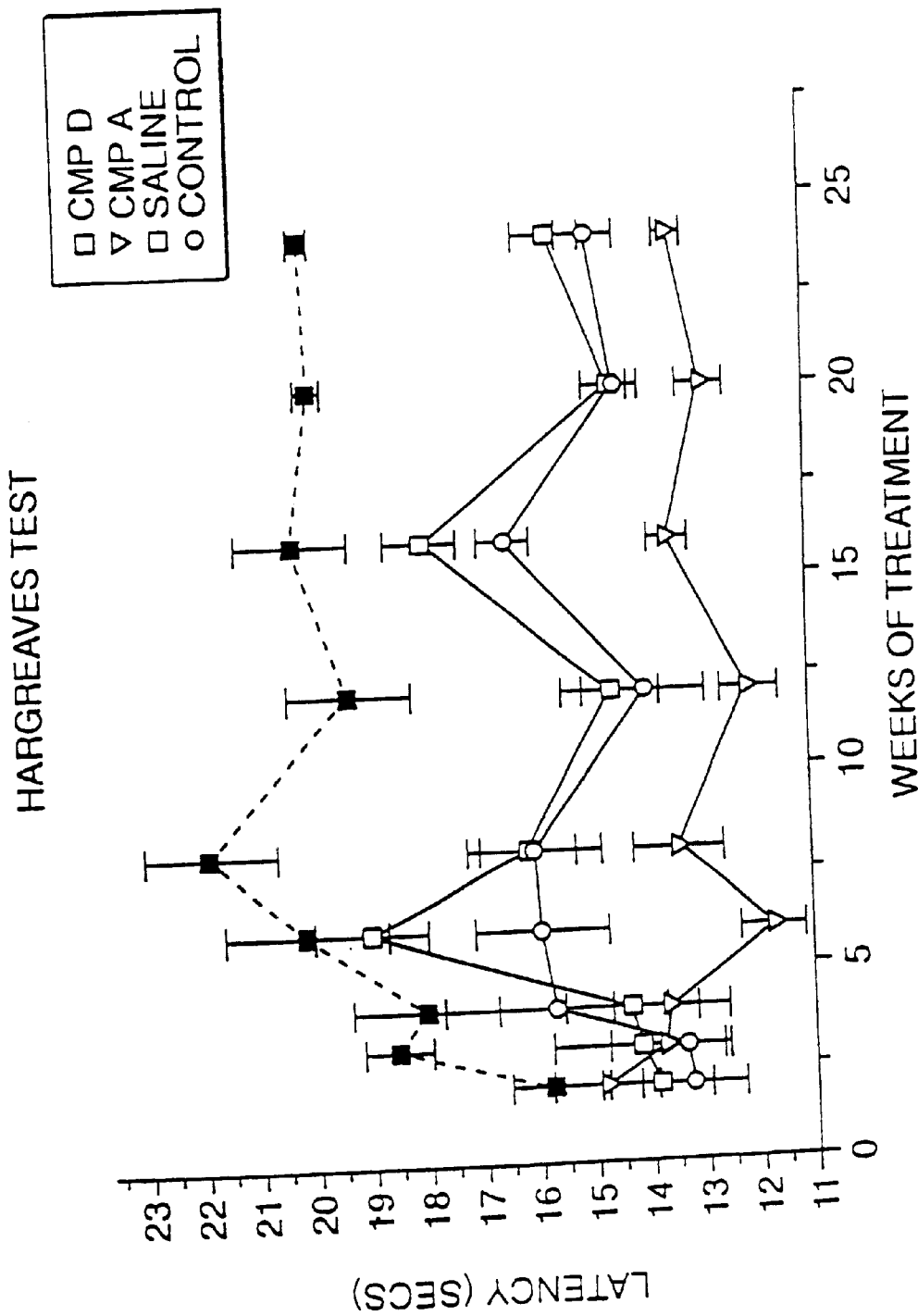
FIG. 17 is a graph plotting the withdrawal latency of non-diabetic rats and BB/W diabetic rats treated with a vehicle, Compound D, or Compound A, against the weeks of treatment.

The results are graphically presented in FIG. 17. The results show that diabetic rats displayed a hyperalgesia (shorter response latency) compared to non-diabetic controls. Diabetic drug-treated rats (both Compound D and Compound A) displayed longer withdrawal latencies than diabetic vehicle-treated rats, starting after 4 weeks of treatment and persisting through the six months of treatment.

Figure 18:
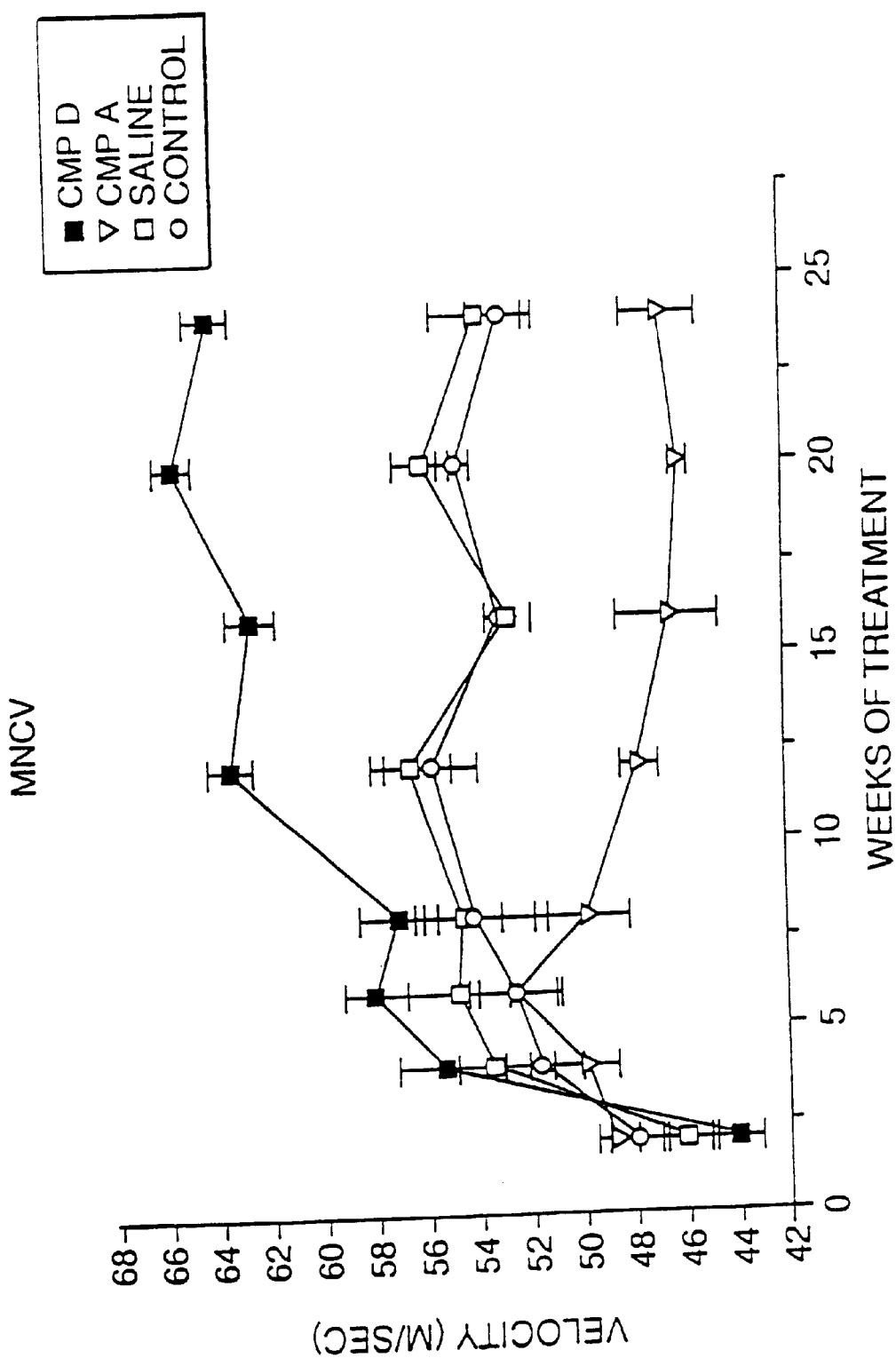
FIG. 18 is a graph plotting the nerve conduction velocity of non-diabetic rats and BB/W diabetic rats treated with a vehicle, Compound D, or Compound A, against the weeks of treatment.

Nerve conduction velocity was also measured every two weeks through the first eight weeks of treatment and every month thereafter through to the six months of treatment. For detailed method, see De Koning et al., *Peptides* 1987 May-Jun; 8(3):415–22. The results are graphically presented in FIG. 18. Diabetic animals generally showed a reduction in nerve conduction velocity compared to non-diabetic controls. However, diabetic animals receiving daily injections of NAALADase inhibitor (either Compound D or Compound A at a dose of 10 mg/kg) showed significantly less severe nerve conduction deficits than did the diabetic controls receiving vehicle treatment. This was apparent starting at 8 weeks of treatment and persisted to a similar degree through to the six month termination point of the study. Diabetic vehicles, on the other hand, showed a progressive deterioration in nerve conduction velocity from 6 to 16 weeks after start of vehicle administration which was maintained through to six months.

Example 10

In Vivo Assay of NAALADase Inhibitors on Diabetic Neuropathy

Figure 15A:
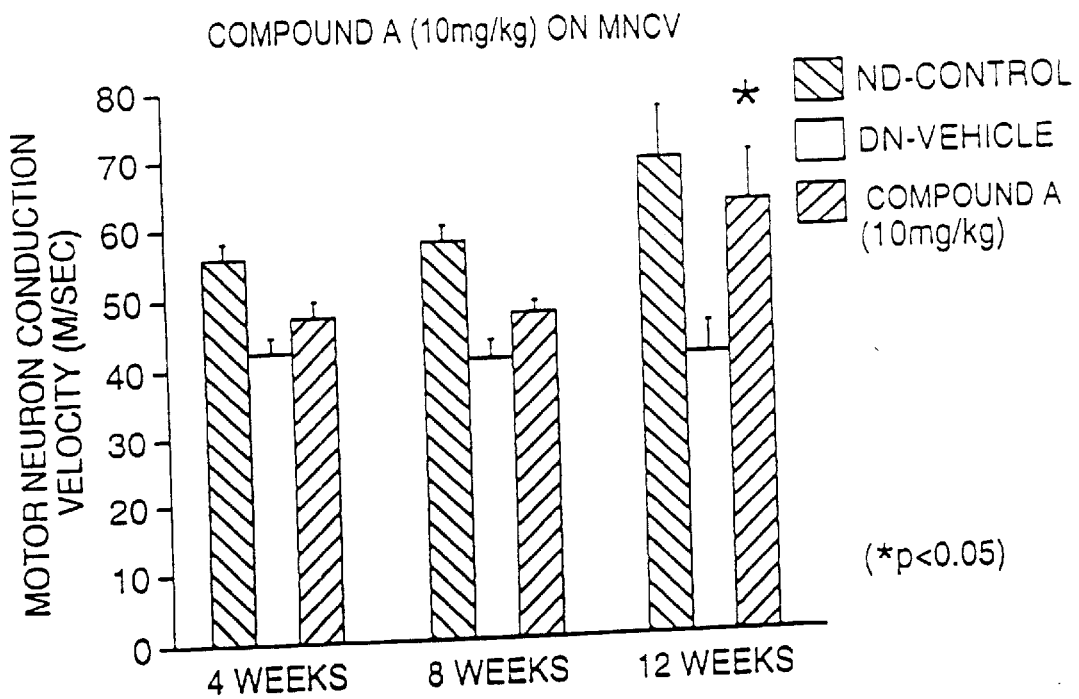
FIG. 15A is a bar graph plotting the motor nerve conduction velocity of non-diabetic rats and STZ-diabetic rats treated with a vehicle or Compound A, against the weeks following administration with STZ.
Figure 15B:
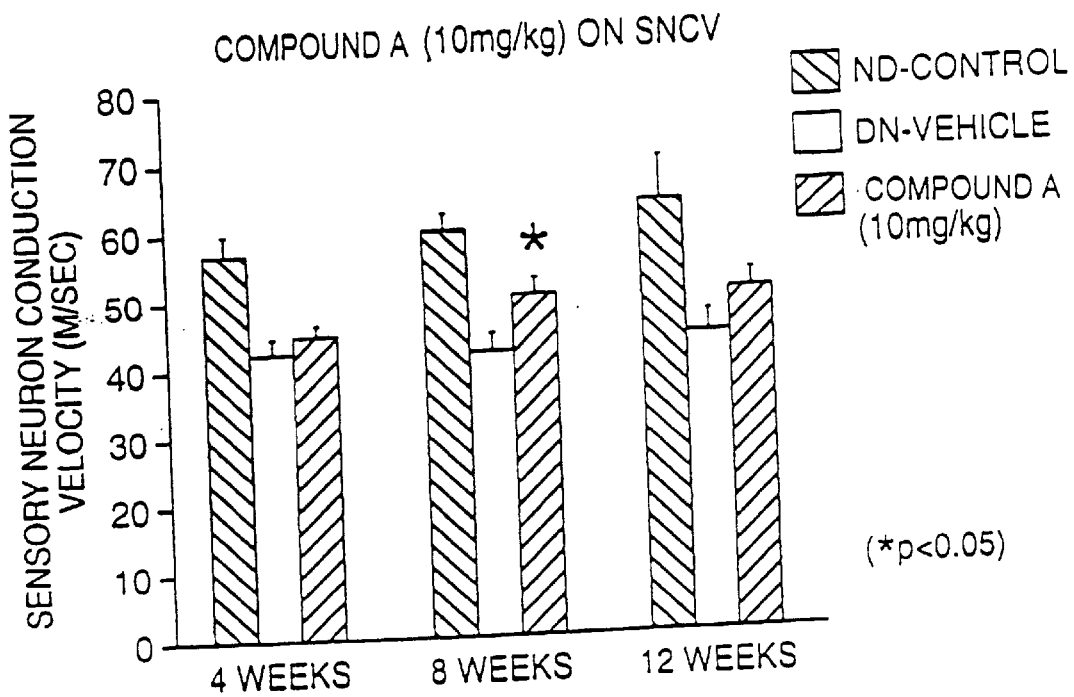
FIG. 15B is a bar graph plotting the sensory nerve conduction velocity of non-diabetic rats and STZ-diabetic rats treated with a vehicle or Compound A, against the weeks following administration with STZ.
Figure 16A:
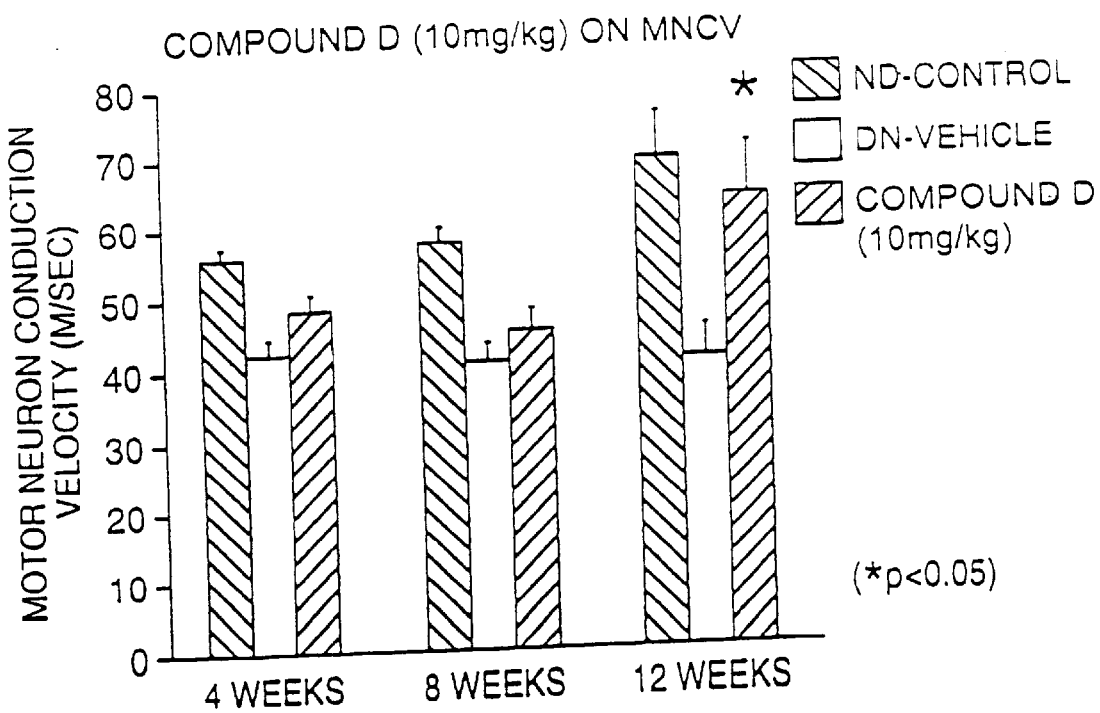
FIG. 16A is a bar graph plotting the motor nerve conduction velocity of non-diabetic rats and STZ-diabetic rats treated with a vehicle or Compound D, against the weeks following administration with STZ.
Figure 16B:
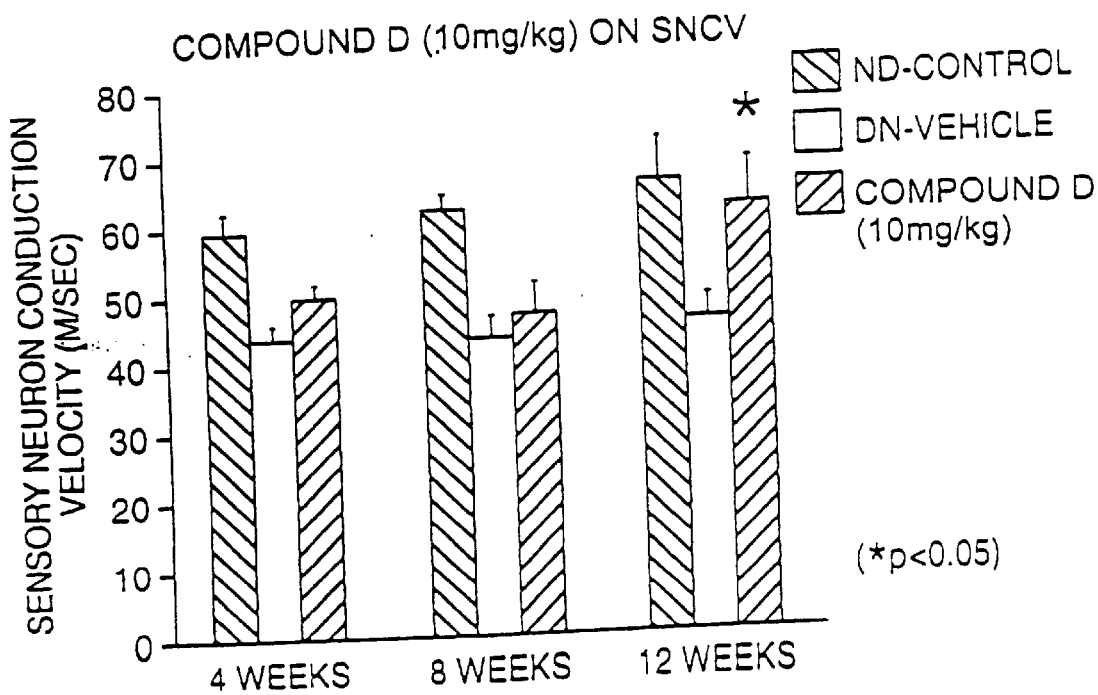
FIG. 16B is a bar graph plotting the sensory nerve conduction velocity of non-diabetic rats and STZ-diabetic rats treated with a vehicle or Compound D, against the weeks following administration with STZ.

Motor and sensory nerve conduction velocity was also measured in STZ-diabetic animals after 4, 8 and 12 weeks of treatment. For detailed method, see De Koning et al., Peptides 1987 May-Jun; 8(3):415–22. Briefly, stimulating needle electrodes were inserted close to the sciatic and tibial nerves with recording electrodes being placed subcutaneously over the distal foot muscles, in anesthetized rats. The results are graphically presented in FIGS. 15A, 15B, 16A and 16B. Diabetic animals receiving vehicle showed a significant reduction in both motor and sensory nerve conduction compared to non-diabetic animals. Treatment with 10 mg/kg of Compound A daily for 4, 8 and 12 weeks all tended to improve (increase) both motor and sensory nerve conduction velocities, with a significant improvement being observed after 12 weeks and 8 weeks for motor and sensory nerve conduction velocity, respectively (FIGS. 15A and 15B). A lower dose of Compound A tested (1 mg/kg) had similar effects. Treatment of animals with Compound D at either dose also increased both motor and sensory nerve conduction velocities above that of diabetic controls, significantly so after 12 weeks of treatment for the 10 mg/kg treatment group (FIGS. 16A and 16B) and at the earlier time periods after treatment with the 1 mg/kg dose. Thus, the results show that NAALADase inhibition alters the progression of diabetic neuropathy.

Example 11

A patient is suffering from any disease, disorder or condition mediated by NAALDase enzyme activity, including any of the diseases, disorders or conditions described above. The patient may then be administered an effective amount of a compound of formula 1. It is expected that after such treatment, the patient would not suffer any significant injury due to, would be protected from further injury due to, or would recover from the disease, disorder or condition.

All publications, patents and patent applications identified above are herein incorporated by reference, as though set forth herein in full.

Those skilled in the art will recognize that the invention may be varied in many ways without departing from the invention's spirit and scope. Such variations are included within the scope of the following claims.

We claim:
1. A compound of formula I

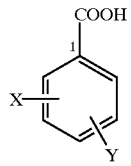

or a pharmaceutically acceptable equivalent, wherein:
X is —(CR$_1$R$_2$)$_n$NH(CR$_3$R$_4$)$_m$COOH, —PO(OH)OR$_5$, —(CR$_1$R$_2$)$_n$P(O)(OH)OR$_5$, —NH(P(O)(OH)R$_6$), —(CR$_1$R$_2$)$_n$NHP(O)(OH)R$_6$), —CON(R$_5$)(OH), —(CR$_1$R$_2$)$_n$CON(R$_5$)(OH), —(CR$_1$R$_2$)$_n$SH, —O(CR$_3$R$_4$)$_m$SH, —SO$_2$NH-aryl, —N(C=O)—CH$_2$(C=O)-aryl, —SO$_2$NH-aryl-N(C=O)—CH$_2$(C=O)-aryl, —O-aryl wherein aryl in —SO$_2$NH-aryl is substituted by halogen, —NR$_{(C=O)-(CR1}$R$_2$)(C=O)-aryl, —SO$_2$NH-aryl-N(C=O)-aryl, or —O-aryl wherein aryl in —O-aryl is substituted by at least one nitro group,
wherein X is oriented meta or para to C-1;
m and n are indepenently 1–3, provided that when X is —O(CR$_3$R$_4$)$_m$SH, then m is 2 or 3;
R$_1$, R$_2$, R$_3$, R$_4$, R$_5$, and R$_6$ are independently hydrogen, C$_1$–C$_6$ alkyl, C$_2$–C$_6$ alkenyl, C$_2$–C$_6$ alkynyl, aryl, carbocycle, heterocycle, halo, hydroxy, sulfhydryl, nitro, amino or C$_1$–C$_6$ alkoxy, wherein said alkyl, alkenyl, alkynyl, aryl, carbocycle, or alkoxy is independently unsubstituted or substituted with one or more substituent(s); and
Y is —COOH oriented meta or para relative to C-1;
provided that:
when X is —PO(OH)OR$_5$, or —(CR$_1$R$_2$)$_n$P(O)(OH)OR$_5$, then R$_5$ is not H or methyl,
when X is —NH(P(O)(OH)R$_6$), or —(CR$_1$R$_2$)$_n$NHP(O)(OH)R$_6$), then R$_6$ is not benzyl unsubstituted or substituted with amino or nitro, and
when X is —CON(R$_5$)(OH), then R$_5$ is not H or methyl.
2. The compound of claim 1, wherein:
X is oriented meta relative to C-1; and
Y is oriented ortho relative to X and para relative to C-1.
3. The compound of claim 1, wherein:
X is oriented ortho relative to C-1; and
Y is oriented para relative to X and meta relative to C-1.
4. The compound of claim 3, wherein the compound is:
4-[3-[[3-(2,4-dicarboxyphenoxy)propyl]dithio]-propoxy]-1,3-benzenedicarboxylic acid (19);
4-(2-mercaptoethyl)-1,3-benzenedicarboxylic acid (22); or pharmaceutically acceptable equivalents.
5. The compound of claim 1, wherein:
x is oriented meta relative to C-1;
y is oriented meta relative to X and meta relative to C-1.
6. The compound of claim 5, wherein the compound is:
5-[[(4-chloro-3-nitrophenyl)amino]sulfonyl]-1,3-benzenedicarboxylic acid (25);
5-[[[4chloro-3-[[3-(2-methoxyphenyl)-1,3-dioxopropyl]amino]phenyl]amino]sulfonyl-1,3-benzenedicarboxylic acid (26);
5-[[3-[4-(acetylamino)phenyl]-1,3-dioxopropyl]amino]-1,3-benzenedicarboxylic acid (27);
5-(4-carboxy-2-nitrophenoxy)-1,3-benzenedicarboxylic acid (30);
5-[[(3-amino-4-chlorophenyl)amino]sulfonyl]-1,3-benzenedicarboxylic acid (35);
5-(3-mercaptopropoxy)-1,3-benzenedicarboxylic acid (36);
5-(2-mercaptoethoxy)-1,3-benzenedicarboxylic acid (38);
5-[(hydroxyamino)-carbonyl]-1,3-benzenedicarboxylic acid (39);
5-phosphono-1,3-benzenedicarboxylic acid (40);
5-mercaptomethyl-1,3-benzenedicarboxylic acid (41);
5-phosphonomethyl-1,3-benzenedicarboxylic acid (42);
5-[[(carboxyrnethyl)amino]-methyl]-1,3-benzenedicarboxylic acid (43);
5-[2-(hydroxyamino)-2-oxoethyl]-1,3-benzenedicarboxylic acid (46);
5-(2-mercaptoethyl)-1,3-benzenedicarboxylic acid (47);
or pharmaceutically acceptable equivalents.
7. A method for treating a glutamate abnormality in a mammal, comprising administering to said mammal an effective amount of a compound of formula I

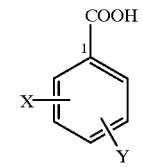

or a pharmaceutically acceptable equivalent, wherein:
X is —(CR$_1$R$_2$)$_n$NH(CR$_3$R$_4$)$_m$COOH, —PO(OH)OR$_5$, —(CR$_1$R$_2$)$_n$P(O)(OH)OR$_5$, —NH(P(O)(OH)R$_6$), —(CR$_1$R$_2$)$_n$NHP(O)(OH)R$_6$), —CON(R$_5$)(OH), —(CR$_1$R$_2$)$_n$CON(R$_5$)(OH), —(CR$_1$R$_2$)$_n$SH, —O(CR$_3$R$_4$)$_m$SH, —SO$_2$NH-aryl, —N(C=O)—CH$_2$(C=O)-aryl, —SO$_2$NH-aryl-N(C=O)—CH$_2$(C=O)-aryl, —O-aryl wherein aryl in —O-aryl is substituted by at least one of nitro or carboxy,
wherein X is oriented meta or para to C-1;
m and n are indepenently 1–3, provided that when X is —O(CR$_3$R$_4$)$_m$SH, then m is 2 or 3;
R$_1$, R$_2$, R$_3$, R$_4$, R$_5$, and R$_6$ are independently hydrogen, C$_1$–C$_6$ alkyl, C$_2$–C$_6$ alkenyl, C$_2$–C$_6$ alkynyl, aryl, carbocycle, halo, hydroxy, sulfhydryl, nitro, amino or C$_1$–C$_6$ alkoxy, wherein said alkyl, alkenyl, alkynyl, aryl, carbocycle, or alkoxy is independently unsubstituted or substituted with one or more substituent(s); and
Y is —COOH oriented meta or para relative to C-1;
provided that:
when X is —PO(OH)OR$_5$, or —(CR$_1$R$_2$)$_n$P(O)(OH)OR$_5$, then R$_5$ is not H or methyl,
when X is —NH(P(O)(OH)R$_6$), or —(CR$_1$R$_2$)$_n$NHP(O)(OH)R$_6$), then R$_6$ is not benzyl unsubstituted or substituted with amino or nitro, and
when X is —CON(R$_5$)(OH), then R$_5$ is not H or methyl.
8. The method of claim 7, wherein the glutamate abnormality is compulsive disorder, stroke, demyelinating disease, schizophrenia, Parkinson's disease, ALS, anxiety, anxiety disorder, or memory impairment.
9. The method of claim 8, wherein the glutamate abnormality is alcohol dependence.
10. The method of claim 8, wherein the glutamate abnormality is nicotine dependence.

11. The method of claim 8, wherein the glutamate abnormality is cocaine dependence.

12. A method for effecting a neuronal activity in a mammal, comprising administering to said mammal an effective amount of a compound of formula I

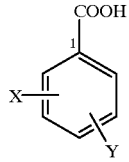

or a pharmaceutically acceptable equivalent, wherein:
X is —$(CR_1R_2)_nNH(CR_3R_4)_mCOOH$, —$PO(OH)OR_5$, —$(CR_1R_2)_nP(O)(OH)OR_5$, —$NH(P(O)(OH)R_6)$, —$(CR_1R_2)_nNHP(O)(OH)R_6$, —$CON(R_5)(OH)$, —$(CR_1R_2)_nCON(R_5)(OH)$, —$(CR_1R_2)_nSH$, —$O(CR_3R_4)_mSH$, —$SO_2NH$-aryl, —$N(C=O)$—$CH_2(C=O)$-aryl, —$SO_2NH$-aryl-$N(C=O)$—$CH_2(C=O)$-aryl, —O-aryl wherein aryl in —O-aryl is substituted by at least one of nitro or carboxy,
wherein X is oriented meta or para to C-1;
m and n are indepenently 1–3, provided that when X is —$O(CR_3R_4)_mSH$, then m is 2 or 3;
$R_1$, $R_2$, $R_3$, $R_4$, $R_5$, and $R_6$ are independently hydrogen, $C_1$–$C_6$ alkyl, $C_2$–$C_6$ alkenyl, $C_2$–$C_6$ alkynyl, aryl, carbocycle, halo, hydroxy, sulfhydryl, nitro, amino or $C_1$–$C_6$ alkoxy, wherein said alkyl, alkenyl, alkynyl, aryl, carbocycle, or alkoxy is independently unsubstituted or substituted with one or more substituent(s); and
Y is —COOH oriented meta or para relative to C-1;
provided that:
when X is —$PO(OH)OR_5$, or —$(CR_1R_2)_nP(O)(OH)OR_5$, then $R_5$ is not H or methyl,
when X is —$NH(P(O)(OH)R_6)$, or —$(CR_1R_2)_nNHP(O)(OH)R_6$, then $R_6$ is not benzyl unsubstituted or substituted with amino, and
when X is —$CON(R_5)(OH)$, then $R_5$ is not H or methyl.

13. The method of claim 12, wherein the neuronal activity is stimulation of damaged neurons, promotion of neuronal regeneration, prevention of neurodegeneration, or treatment of a neurological disorder.

14. The method of claim 13, wherein the neuronal activity is treatment of a neurological disorder that is pain, neuropathy, traumatic brain injury, physical damage to spinal cord, stroke associated with brain damage, demyelinating disease, or a neurological disorder relating to neurodegeneration.

15. The method of claim 14, wherein the method is treating peripheral neuropathy.

16. The method of claim 15, wherein the peripheral neuropathy is caused by Type I or Type II diabetes, HIV, vitamins, or non-vitamin chemicals.

17. The method of claim 14, wherein the method is treatment of neuropathic pain.

18. The method of claim 17, wherein the neuropathic pain is caused by Type I or Type II diabetes, HIV, vitamins, or non-vitamin chemicals.

19. The method of claim 17, wherein the compound of formula I is administered in combination with an effective amount of morphine.

20. The method of claim 14, wherein the neuronal activity is treatment of Parkinson's disease or ALS.

21. A method for effecting a neuronal activity in a mammal, comprising administering to said mammal an effective amount of a compound of formula I

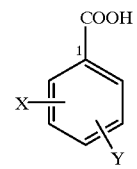

or a pharmaceutically acceptable equivalent, wherein:
X is —$(CR_1R_2)_nNH(CR_3R_4)_mCOOH$, —$PO(OH)OR_5$, —$(CR_1R_2)_nP(O)(OH)OR_5$, —$NH(P(O)(OH)R_6)$, —$(CR_1R_2)_nNHP(O)(OH)R_6$, —$CON(R_5)(OH)$, —$(CR_1R_2)_nCON(R_5)(OH)$, —$(CR_1R_2)_nSH$, —$O(CR_3R_4)_mSH$, —$SO_2NH$-aryl, —$N(C=O)$—$CH_2(C=O)$-aryl, —$SO_2NH$-aryl-$N(C=O)$—$CH_2(C=O)$-aryl, —O-aryl wherein aryl in —O-aryl is substituted by at least one of nitro or carboxy,
wherein X is oriented meta or para to C-1;
m and n are indepenently 1–3, provided that when X is —$O(CR_3R_4)_mSH$, then m is 2 or 3;
$R_1$, $R_2$, $R_3$, $R_4$, $R_5$, and $R_6$ are independently hydrogen, $C_1$–$C_6$ alkyl, $C_2$–$C_6$ alkenyl, $C_2$–$C_6$ alkynyl, aryl, carbocycle, halo, hydroxy, sulfhydryl, nitro, amino or $C_1$–$C_6$ alkoxy, wherein said alkyl, alkenyl, alkynyl, aryl, carbocycle, heterocycle, or alkoxy is independently unsubstituted or substituted with one or more substituent(s); and
Y is —COOH oriented meta or para relative to C-1,
provided that:
when X is —$PO(OH)OR_5$, or —$(CR_1R_2)_nP(O)(OH)OR_5$, then $R_5$ is not H or methyl,
when X is —$NH(P(O)(OH)R_6)$, or —$(CR_1R_2)_nNHP(O)(OH)R_6$, then $R_6$ is not benzyl unsubstituted or substituted with amino, and
when X is —$CON(R_5)(OH)$, then $R_5$ is not H or methyl.

22. The method of claim 21, wherein the prostate disease is prostate cancer.

23. A method for effecting a neuronal activity in a mammal, comprising administering to said mammal an effective amount of a compound of formula I

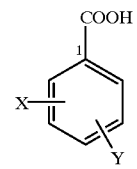

or a pharmaceutically acceptable equivalent, wherein:
X is —$(CR_1R_2)_nNH(CR_3R_4)_mCOOH$, —$PO(OH)OR_5$, —$(CR_1R_2)_nP(O)(OH)OR_5$, —$NH(P(O)(OH)R_6)$, —$(CR_1R_2)_nNHP(O)(OH)R_6$, —$CON(R_5)(OH)$, —$(CR_1R_2)_nCON(R_5)(OH)$, —$(CR_1R_2)_nSH$, —$O(CR_3R_4)_mSH$, —$SO_2NH$-aryl, —$N(C=O)$—$CH_2(C=O)$-aryl, —$SO_2NH$-aryl-$N(C=O)$—$CH_2(C=O)$-aryl, —O-aryl wherein aryl in —O-aryl is substituted by at least one of nitro or carboxy,
wherein X is oriented meta or para to C-1;
m and n are indepenently 1–3, provided that when X is —$O(CR_3R_4)_mSH$, then m is 2 or 3;

$R_1$, $R_2$, $R_3$, $R_4$, $R_5$, and $R_6$ are independently hydrogen, $C_1$–$C_6$ alkyl, $C_2$–$C_6$ alkenyl, $C_2$–$C_6$ alkynyl, aryl, heteroaryl, carbocycle, heterocycle, halo, hydroxy, sulfhydryl, nitro, amino or $C_1$–$C_6$ alkoxy, wherein said alkyl, alkenyl, alkynyl, aryl, heteroaryl, carbocycle, heterocycle, or alkoxy is independently unsubstituted or substituted with one or more substituent(s); and Y is —COOH oriented meta or para relative to C-1, provided that:

when X is —PO(OH)OR$_5$, or —(CR$_1$R$_2$)$_n$P(O)(OH)OR$_5$, then R$_5$ is not H or methyl, when X is —NH(P(O)(OH)R$_6$), or —(CR$_1$R$_2$)$_n$NHP(O)(OH)R$_6$), then R$_6$ is not benzyl unsubstituted or substituted with amino, and when X is —CON(R$_5$)(OH), then R$_5$ is not H or methyl.

24. The method of claim 23, wherein the cancer is of the brain, kidney, or testis.

25. A method for effecting a neuronal activity in a mammal, comprising administering to said mammal an effective amount of a compound of formula I

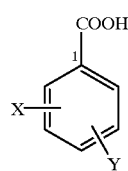

I or a pharmaceutically acceptable equivalent, wherein:

X is —(CR$_1$R$_2$)$_n$NH(CR$_3$R$_4$)$_m$COOH, —PO(OH)OR$_5$, —(CR$_1$R$_2$)$_n$P(O)(OH)OR$_5$, —NH(P(O)(OH)R$_6$), —(CR$_1$R$_2$)$_n$NHP(O)(OH)R$_6$), —CON(R$_5$)(OH), —(CR$_1$R$_2$)$_n$CON(R$_5$)(OH), —(CR$_1$R$_2$)$_n$SH, —O(CR$_3$R$_4$)$_m$SH, —SO$_2$NH-aryl, —N(C=O)—CH$_2$(C=O)-aryl, —SO$_2$NH-aryl-N(C=O)—CH$_2$(C=O)-aryl, —O-aryl wherein aryl in —O-aryl is substituted by at least one of nitro or carboxy, wherein X is oriented meta or para to C-1;

m and n are indepenently 1–3, provided that when X is —O(CR$_3$R$_4$)$_m$SH, then m is 2 or 3;

$R_1$, $R_2$, $R_3$, $R_4$, $R_5$, and $R_6$ are independently hydrogen, $C_1$–$C_6$ alkyl, $C_2$–$C_6$ alkenyl, $C_2$–$C_6$ alkynyl, aryl, carbocycle, halo, hydroxy, sulfhydryl, nitro, amino or $C_1$–$C_6$ alkoxy, wherein said alkyl, alkenyl, alkynyl, aryl, carbocycle, or alkoxy is independently unsubstituted or substituted with one or more substituent(s); and Y is —COOH oriented meta or para relative to C-1, provided that:

when X is —PO(OH)OR$_5$, or —(CR$_1$R$_2$)$_n$P(O)(OH)OR$_5$, then R$_5$ is not H or methyl, when X is —NH(P(O)(OH)R$_6$), or —(CR$_1$R$_2$)$_n$NHP(O)(OH)R$_6$), then R$_6$ is not benzyl unsubstituted or substituted with amino, and when X is —CON(R$_5$)(OH), then R$_5$ is not H or methyl.

26. A method for treating a TGF-β abnormality in a mammal, comprising administering to said mammal an effective amount of a compound of formula I

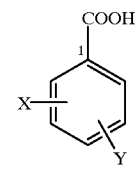

I or a pharmaceutically acceptable equivalent, wherein:

X is —(CR$_1$R$_2$)$_n$NH(CR$_3$R$_4$)$_m$COOH, —PO(OH)OR$_5$, —(CR$_1$R$_2$)$_n$P(O)(OH)OR$_5$, —NH(P(O)(OH)R$_6$), —(CR$_1$R$_2$)$_n$NHP(O)(OH)R$_6$), —CON(R$_5$)(OH), —(CR$_1$R$_2$)$_n$CON(R$_5$)(OH), —(CR$_1$R$_2$)$_n$SH, —O(CR$_3$R$_4$)$_m$SH, —SO$_2$NH-aryl, —N(C=O)—CH$_2$(C=O)-aryl, —SO$_2$NH-aryl-N(C=O)—CH$_2$(C=O)-aryl, —O-aryl wherein aryl in —O-aryl is substituted by at least one of nitro or carboxy, wherein X is oriented meta or para to C-1;

m and n are indepenently 1–3, provided that when X is —O(CR$_3$R$_4$)$_m$SH, then m is 2 or 3;

$R_1$, $R_2$, $R_3$, $R_4$, $R_5$, and $R_6$ are independently hydrogen, $C_1$–$C_6$ alkyl, $C_2$–$C_6$ alkenyl, $C_2$–$C_6$ alkynyl, aryl, heteroaryl, carbocycle, heterocycle, halo, hydroxy, sulfhydryl, nitro, amino or $C_1$–$C_6$ alkoxy, wherein said alkyl, alkenyl, alkynyl, aryl, heteroaryl, carbocycle, heterocycle, or alkoxy is independently unsubstituted or substituted with one or more substituent(s); and Y is —COOH oriented meta or para relative to C-1;

provided that:

when X is —PO(OH)OR$_5$, or —(CR$_1$R$_2$)$_n$P(O)(OH)OR$_5$, then R$_5$ is not H or methyl, when X is —NH(P(O)(OH)R$_6$), or —(CR$_1$R$_2$)$_n$NHP(O)(OH)R$_6$), then R$_6$ is not benzyl unsubstituted or substituted with amino, and when X is —CON(R$_5$)(OH), then R$_5$ is not H or methyl.

27. A method for inhibiting NAALADase in a mammal, comprising administering to said mammal an effective amount of a compound of formula I

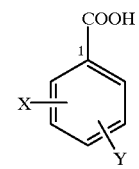

I or a pharmaceutically acceptable equivalent, wherein:

X is —(CR$_1$R$_2$)$_n$NH(CR$_3$R$_4$)$_m$COOH, —PO(OH)OR$_5$, —(CR$_1$R$_2$)$_n$P(O)(OH)OR$_5$, —NH(P(O)(OH)R$_6$), —(CR$_1$R$_2$)$_n$NHP(O)(OH)R$_6$), —CON(R$_5$)(OH), —(CR$_1$R$_2$)$_n$CON(R$_5$)(OH), —(CR$_1$R$_2$)$_n$SH, —O(CR$_3$R$_4$)$_m$SH, —SO$_2$NH-aryl, —N(C=O)—CH$_2$(C=O)-aryl, —SO$_2$NH-aryl-N(C=O)—CH$_2$(C=O)-aryl, —O-aryl wherein aryl in —O-aryl is substituted by at least one of nitro or carboxy, wherein X is oriented meta or para to C-1;

m and n are indepenently 1–3, provided that when X is —O(CR$_3$R$_4$)$_m$SH, then m is 2 or 3;

$R_1$, $R_2$, $R_3$, $R_4$, $R_5$, and $R_6$ are independently hydrogen, $C_1$–$C_6$ alkyl, $C_2$–$C_6$ alkenyl, $C_2$–$C_6$ alkynyl, aryl, carbocycle, halo, hydroxy, sulfhydryl, nitro, amino or $C_1$–$C_6$ alkoxy, wherein said alkyl, alkenyl, alkynyl, aryl, carbocycle, or alkoxy is independently unsubstituted or substituted with one or more substituent(s); and Y is —COOH oriented meta or para relative to C-1;

provided that:

when X is —PO(OH)OR$_5$, or —(CR$_1$R$_2$)$_n$P(O)(OH)OR$_5$, then R$_5$ is not H or methyl, when X is —NH(P(O)(OH)R$_6$), or —(CR$_1$R$_2$)$_n$NHP(O)(OH)R$_6$), then R$_6$ is not benzyl unsubstituted or substituted with amino, and when X is —CON(R$_5$)(OH), then R$_5$ is not H or methyl.

28. A method for treating nervous insult in a mammal, comprising administering to said mammal an effective amount of a compound of formula I

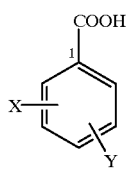

or a pharmaceutically acceptable equivalent, wherein:

X is —(CR$_1$R$_2$)$_n$NH(CR$_3$R$_4$)$_m$COOH, —PO(OH)OR$_5$, —(CR$_1$R$_2$)$_n$P(O)(OH)OR$_5$, —NH(P(O)(OH)R$_6$), —(CR$_1$R$_2$)$_n$NHP(O)(OH)R$_6$), —CON(R$_5$)(OH), —(CR$_1$R$_2$)$_n$CON(R$_5$)(OH), —(CR$_1$R$_2$)$_n$SH, —O(CR$_3$R$_4$)$_m$SH, —SO$_2$NH-aryl, —N(C=O)—CH$_2$(C=O)-aryl, —SO$_2$NH-aryl-N(C=O)—CH$_2$(C=O)-aryl, —O-aryl wherein aryl in —O-aryl is substituted by at least one of nitro or carboxy, wherein X is oriented meta or para to C-1;

m and n are indepenently 1–3, provided that when X is —O(CR$_3$R$_4$)$_m$SH, then m is 2 or 3;

R$_1$, R$_2$, R$_3$, R$_4$, R$_5$, and R$_6$ are independently hydrogen, C$_1$–C$_6$ alkyl, C$_2$–C$_6$ alkenyl, C$_2$–C$_6$ alkynyl, aryl, carbocycle, halo, hydroxy, sulfhydryl, nitro, amino or C$_1$–C$_6$ alkoxy, wherein said alkyl, alkenyl, alkynyl, aryl, carbocycle, heterocycle, or alkoxy is independently unsubstituted or substituted with one or more substituent(s); and Y is —COOH oriented meta or para relative to C-1;

provided that:

when X is —PO(OH)OR$_5$, or —(CR$_1$R$_2$)$_n$P(O)(OH)OR$_5$, then R$_5$ is not H or methyl, when X is —NH(P(O)(OH)R$_6$), or —(CR$_1$R$_2$)$_n$NHP(O)(OH)R$_6$), then R$_6$ is not benzyl unsubstituted or substituted with amino, and when X is —CON(R$_5$)(OH), then R$_5$ is not H or methyl.

29. The method of claim 28, wherein the nervous insult comprises a cognitive disorder.

30. A pharmaceutical composition comprising:

(i) an effective amount of a compound formula I

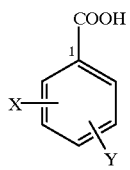

or a pharmaceutically acceptable equivalent, wherein:

X is —(CR$_1$R$_2$)$_n$NH(CR$_3$R$_4$)$_m$COOH, —PO(OH)OR$_5$, —(CR$_1$R$_2$)$_n$P(O)(OH)OR$_5$, —NH(P(O)(OH)R$_6$), —(CR$_1$R$_2$)$_n$NHP(O)(OH)R$_6$), —CON(R$_5$)(OH), —(CR$_1$R$_2$)$_n$CON(R$_5$)(OH), —(CR$_1$R$_2$)$_n$SH, —O(CR$_3$R$_4$)$_m$SH, —SO$_2$NH-aryl, —N(C=O)—CH$_2$(C=O)-aryl, —SO$_2$NH-aryl-N(C=O)—CH$_2$(C=O)-aryl, —O-aryl wherein aryl in —SO$_2$NH-aryl is substituted by halogen, —NR$_{(C=O)-(CR_1}$R$_2$)(C=O)-aryl, —SO$_2$NH-aryl-N(C=O)-aryl, or —O-aryl wherein aryl in —O-aryl is substituted by at least one nitro group, wherein X is oriented meta or para to C-1;

m and n are indepenently 1–3, provided that when X is —O(CR$_3$R$_4$)$_m$SH, then m is 2 or 3;

R$_1$, R$_2$, R$_3$, R$_4$, R$_5$, and R$_6$ are independently hydrogen, C$_1$–C$_6$ alkyl, C$_2$–C$_6$ alkenyl, C$_2$–C$_6$ alkynyl, aryl, carbocycle, halo, hydroxy, sulfhydryl, nitro, amino or C$_1$–C$_6$ alkoxy, wherein said alkyl, alkenyl, alkynyl, aryl, carbocycle, or alkoxy is independently unsubstituted or substituted with one or more substituent(s); and Y is —COOH oriented meta or para relative to C-1;

provided that when X is —NH(PO(OH)OR$_6$), or —(CR$_1$R$_2$)$_n$NH(P(O)(OH)OR$_6$), then R$_6$ is not benzyl unsubstituted or substituted with amino or nitro; and (ii) a pharmaceutically acceptable carrier.

31. The composition of claim 30, wherein:

X is oriented meta relative to C-1; and

Y is oriented ortho relative to X and para relative to C-1.

32. The composition of claim 33, wherein the compound of formula I is selected from the group consisting of:

2-[(4-carboxyphenyl)sulfonyl]-1,4-benzene-dicarboxylic acid (1);

2-[(2,5-dicarboxyphenyl)sulfonyl]-1,4-benzene-dicarboxylic acid (2);

1,2,4-benzenetricarboxylic acid (3);

2-[(2-carboxyphenyl)thio]-1,4-benzenedicarboxylic acid (4);

2-nitro-1,4-benzenedicarboxylic acid (5);

2-bromo-1,4-benzenedicarboxylic acid (6);

2-amino-1,4-benzenedicarboxylic acid (7);

2-sulfoterephthalic acid, monosodium salt (8);

2-carboxymethyl-1,4-benzenedicarboxylic acid (9);

2-[(2-furanylmethyl)-amino]-1,4-benzenedicarboxylic acid (10);

2-[(carboxymethyl)amino]-1,4-benzenedicarboxylic acid (11); and pharmaceutically acceptable equivalents.

33. The composition of claim 30, wherein:

X is oriented ortho relative to C-1; and

Y is oriented para relative to X and meta relative to C-1.

34. The composition of claim 33, wherein the compound of formula I is selected from the group consisting of:

4-(4-nitrobenzoyl)-1,3-benzenedicarboxylic acid (12);

4-[4-(2,4-dicarboxybenzoyl)phenoxy]-1,2-benzene-dicarboxylic acid (13);

4-[[(2,4,6-trimethylphenyl)amino]carbonyl]-1,3-benzenedicarboxylic acid (14);

4-nitro-1,3-benzenedicarboxylic acid (15);

4-[(1-naphthalenylamino)-carbonyl]-1,3-benzene-dicarboxylic acid (16);

1,2,4-benzenetricarboxylic acid (17);

4-[(2-carboxyphenyl)thio]-1,3-benzenedicarboxylic acid (18);

4-[3-[[3-(2,4-dicarboxyphenoxy)propyl]dithio]-propoxy]-1,3-benzenedicarboxylic acid (19);

4-hydroxy-1,3-benzenedicarboxylic acid (20);

4-(2-mercaptoethyl)-1,3-benzenedicarboxylic acid (22); and pharmaceutically acceptable equivalents.

35. The composition of claim 30, wherein:

X is oriented meta relative to C-1; and

Y is oriented meta relative to X and meta relative to C-1.

36. The composition of claim 35, wherein the compound of formula I is selected from the group consisting of:

5-[[(4-chloro-3-nitrophenyl)amino]sulfonyl]-1,3-benzenedicarboxylic acid (25);

5-[[[4-chloro-3-[[3-(2-metioxyphenyl)-1,3-dioxopropyl]amino]phenyl]amino]sulfonyl-1,3-benzenedicarboxylic acid (26);

5-[[3-[4-(acetylamino)phenyl]-1,3-dioxopropyl]amino]-1,3-benzenedicarboxylic acid (27);

5-acetylamino-1,3-benzenedicarboxylic acid (28); 5-[[(1-hydroxy-2-naphthalenyl)carbonyl]-methylamino]-1,3-benzenedicarboxylic acid (29);

5-(4carboxy-2-nitrophenoxy)-1,3-benzenedicarboxylic acid (30);

5-sulfo-1,3-benzenedicarboxylic acid (31);

5-nitro-1,3-benzenedicarboxylic acid (32);

5-amino-1,3-benzenedicarboxylic acid (33);

1,3,5-benzenetricarboxylic acid (34);

5-[[(3-amino-4-chlorophenyl)amino]sulfonyl]-1,3-benzenedicarboxylic acid (35);

5-(3-mercaptopropoxy)-1,3-benzenedicarboxylic acid (36);

5-hydroxy-1,3-benzenedicarboxylic acid (37);

5-(2-mercaptoethoxy)-1,3-benzenedicarboxylic acid (38);

5-[(hydroxyamino)carbonyl]-1,3-benzenedicarboxylic acid (39);

5-mercaptomethyl-1,3-benzenedicarboxylic acid (41);

5-[[(carboxymethyl)amino]-methyl]-1,3-benzenedicarboxylic acid (43);

5-[(carboxymethyl)amino]-1,3-benzenedicarboxylic acid (44);

5-[2-(hydroxyamino)-2-oxoethyl]-1,3-benzenedicarboxylic acid (46);

5-(2-mercaptoethyl)-1,3-benzenedicarboxylic acid (47); and pharmaceutically acceptable equivalents.

37. A method for detecting a disease, disorder, or condition where NAALADase levels are altered, comprising (i) contacting a sample of bodily tissue or fluid with a compound of formula I,

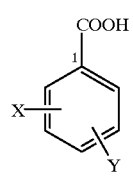

or a pharmaceutically acceptable equivalent, wherein:

X is —(CR$_1$R$_2$)$_n$NH(CR$_3$R$_4$)$_m$COOH, —PO(OH)OR$_5$, —(CR$_1$R$_2$)$_n$P(O)(OH)OR$_5$, —NH(P(O)(OH)R$_6$), —(CR$_1$R$_2$)$_n$NHP(O)(OH)R$_6$), —CON(R$_5$)(OH), —(CR$_1$R$_2$)$_n$CON(R$_5$)(OH), —(CR$_1$R$_2$)$_n$SH, —O(CR$_3$R$_4$)$_m$SH, —SO$_2$NH-aryl, —NR$_5$(C=O)—(CR$_1$R$_2$)(C=O)-aryl, —SO$_2$NH-aryl-N(C=O)—CH$_2$(C=O)-aryl, —O-aryl wherein aryl in —O-aryl is substituted by at least one of nitro or carboxy, wherein X is oriented meta or para to C-1;

m and n are indepenently 1–3, provided that when X is —O(CR$_3$R$_4$)$_m$SH, then m is 2 or 3;

R$_1$, R$_2$, R$_3$, R$_4$, R$_5$, and R$_6$ are independently hydrogen, C$_1$–C$_6$ alkyl, C$_2$–C$_6$ alkenyl, C$_2$–C$_6$ alkynyl, aryl, carbocycle, halo, hydroxy, sulfhydryl, nitro, amino or C$_1$–C$_6$ alkoxy, wherein said alkyl, alkenyl, alkynyl, aryl, carbocycle, or alkoxy is independently unsubstituted or substituted with one or more substituent(s); and Y is —COOH oriented meta or para relative to C-1, provided that:

when X is —PO(OH)OR$_5$, or —(CR$_1$R$_2$)$_n$P(O)(OH)OR$_5$, then R$_5$ is not H or methyl, when X is —NH(P(O)(OH)R$_6$), or —(CR$_1$R$_2$)$_n$NHP(O)(OH)R$_6$), then R$_6$ is not benzyl unsubstituted or substituted with amino, and when X is —CON(R$_5$)(OH), then R$_5$ is not H or methyl, wherein said compound binds to any NAALADase in said sample; and (ii) measuring the amount of any NAALADase bound to said sample, wherein the amount of NAALADase is diagnostic for said disease, disorder, or condition.

38. A method for detecting a disease, disorder, or condition where NAALADase levels are altered in an animal or a mammal, comprising:

(i) labeling a compound of formula I,

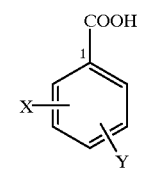

or a pharmaceutically acceptable equivalent, with an imaging reagent, wherein:

X is —(CR$_1$R$_2$)$_n$NH(CR$_3$R$_4$)$_m$COOH, —PO(OH)OR$_5$, —(CR$_1$R$_2$)$_n$P(O)(OH)OR$_5$, —NH(P(O)(OH)R$_6$), —(CR$_1$R$_2$)$_n$NHP(O)(OH)R$_6$), —CON(R$_5$)(OH), —(CR$_1$R$_2$)$_n$CON(R$_5$)(OH), —(CR$_1$R$_2$)$_n$SH, —O(CR$_3$R$_4$)$_m$SH, —SO$_2$NH-aryl, —N(C=O)—CH$_2$(C=O)-aryl, —SO$_2$NH-aryl-N(C=O)—CH$_2$(C=O)-aryl, —O-aryl wherein aryl in —O-aryl is substituted by at least one of nitro or carboxy, wherein X is oriented meta or para to C-1;

m and n are indepenently 1–3, provided that when X is —O(CR$_3$R$_4$)$_m$SH, then m is 2 or 3;

R$_1$, R$_2$, R$_3$, R$_4$, R$_5$, and R$_6$ are independently hydrogen, C$_1$–C$_6$ alkyl, C$_2$–C$_6$ alkenyl, C$_2$–C$_6$ alkynyl, aryl, carbocycle, halo, hydroxy, sulfhydryl, nitro, amino or C$_1$–C$_6$ alkoxy, wherein said alkyl, alkenyl, alkynyl, aryl, carbocycle, or alkoxy is independently unsubstituted or substituted with one or more substituent(s); and Y is —COOH oriented meta or para relative to C-1, provided that:

when X is —PO(OH)OR$_5$, or —(CR$_1$R$_2$)$_n$P(O)(OH)OR$_5$, then R$_5$ is not H or methyl, when X is —NH(P(O)(OH)R$_6$), or —(CR$_1$R$_2$)$_n$NHP(O)(OH)R$_6$), then R$_6$ is not benzyl unsubstituted or substituted with amino, and when X is —CON(R$_5$)(OH), then R$_5$ is not H or methyl, (ii) administering to said animal or mammal an effecive amount of the labeled compound;

(iii) allowing said labeled compound to localize and bind to NAALADase present in said animal or mammal; and (iv) measuring the amount of NAALADase bound to said labeled compound, wherein the amount of NAALADase is diagnostic for said disease, disorder or condition.

\* \* \* \* \*

UNITED STATES PATENT AND TRADEMARK OFFICE
CERTIFICATE OF CORRECTION

PATENT NO. : 6,452,044 B2
DATED : September 17, 2002
INVENTOR(S) : Paul F. Jackson et al.

It is certified that error appears in the above-identified patent and that said Letters Patent is hereby corrected as shown below:

Column 54,
Line 1, please delete "A method for effecting a neuronal activity in a mammal" and insert -- A method for treating a prostate disease in a mammal --.
Line 43, please delete "A method for effecting a neuronal activity in a mammal" and insert -- A method for treating cancer in a mammal --.

Column 55,
Line 21, please delete "A method for effecting a neuronal activity in a mammal" and insert -- A method for inhibiting angiogenesis in a mammal --.

Signed and Sealed this

Twenty-eighth Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,452,044 B2
APPLICATION NO. : 09/866758
DATED : September 17, 2002
INVENTOR(S) : Paul F. Jackson et al.

It is certified that error appears in the above-identified patent and that said Letters Patent is hereby corrected as shown below:

Col. 51, line 16, claim 1 change "NHP(O)" to --NH(P(O)--;
line 18, claim 1 delete "N(C=O)-$CH_2$";
line 19, claim 1 delete in its entirety;
line 20, claim 1 delete "aryl, -O-aryl";
line 21, claim 1 change "$NR_{(C=O)(CR_1R_2)}$" to --$NR_5$(C=O)-($CR_1R_2$)--;
line 21, claim 1 after "N(C=O)-aryl," insert -- -$CH_2$(C=O)-aryl--;
line 31, claim 1 delete "heterocycle,";
line 40, claim 1 change "NHP(O)" to --NH(P(O)--.

Col. 52, line 36, claim 7 change "NHP(O)(OH)$R_6$" to --NH(P(O)(OH)$R_6$)--;
line 38, claim 7 change "N(C=O)-$CH_2$" to --$NR_5$(C=O)-($CR_1R_2$)--;
line 56, claim 7 change "NHP(O)" to --NH(P(O)--.

Col. 53, line 18, claim 12 change "N(C=O)-$CH_2$" to --$NR_5$(C=O)-($CR_1R_2$)--;
line 38, claim 12 change "NHP(O)" to --NH(P(O)--.

Col. 54, line 16, claim 21 change "NHP(O)" to --NH(P(O)--;
line 18, claim 21 change "N(C=O)-$CH_2$" to --$NR_5$(C=O)-($CR_1R_2$)--;
line 30, claim 21 delete "heterocycle,";
line 37, claim 21 change "NHP(O)" to --NH(P(O)--;
line 59, claim 23 change "NHP(O)" to --NH(P(O)--;
line 61, claim 23 change "N(C=O)-$CH_2$" to --$NR_5$(C=O)-($CR_1R_2$)--.

Col. 55, line 3, claim 25 delete "heteroaryl," and delete "heterocycle,";
line 5, claim 25 delete "heteroaryl,";
line 6, claim 25 delete "heterocycle,";
line 14, claim 25 change "NHP(O)" to --NH(P(O)--;
line 38, claim 25 change "NHP(O)" to --NH(P(O)--;
line 40, claim 25 change "N(C=O)-$CH_2$" to --$NR_5$(C=O)-($CR_1R_2$)--;
line 60, claim 25 change "NHP(O)" to --NH(P(O)--.

UNITED STATES PATENT AND TRADEMARK OFFICE
CERTIFICATE OF CORRECTION

PATENT NO. : 6,452,044 B2
APPLICATION NO. : 09/866758
DATED : September 17, 2002
INVENTOR(S) : Paul F. Jackson et al.

It is certified that error appears in the above-identified patent and that said Letters Patent is hereby corrected as shown below:

Col. 56, line 14, claim 26 change "NHP(O)" to --NH(P(O)--;
line 16, claim 26 change "N(C=O)-CH$_2$" to --NR$_5$(C=O)-(CR$_1$R$_2$)--;
line 25, claim 26 delete "heteroaryl," and delete "heterocycle,";
line 27, claim 26 delete "hyteroaryl,";
line 28, claim 26 delete "heterocycle,";
line 35, claim 26 change "NHP(O)" to --NH(P(O)--;
line 55, claim 27 change "NHP(O)" to --NH(P(O)--;
line 58, claim 27 change "N(C=O)-CH$_2$" to --NR$_5$(C=O)-(CR$_1$R$_2$)--.

Col. 57, line 8, claim 27 change "NHP(O)" to --NH(P(O)--;
line 29, claim 28 change "NHP(O)" to --NH(P(O)--;
line 31, claim 28 change "N(C=O)-CH$_2$" to --NR$_5$(C=O)-(CR$_1$R$_2$)--;
line 51, claim 28 change "NHP(O)" to --NH(P(O)--.

Col. 58, line 4, claim 31 change "NHP(O)" to --NH(P(O)--;
line 6, claim 31 delete ""-N(C+O)-CH$_2$";
line 7, claim 31 delete in its entirety;
line 8, claim 31 delete "aryl, -O-aryl";
line 9, claim 31 change "NR$_{(C=O)-(CR_1}$R$_2$)" to --NR$_5$(C=O)-(CR$_1$R$_2$)--;
line 10, claim 31 after "N(C=O)" insert -- -CH$_2$(C=O)--;
line 24, claim 31 change "NH(PO(OH)OR$_6$)" to --NH(P(O)(OH)OR$_6$)--;
line 47, claim 32 delete in its entirety;
line 48, claim 32 delete in its entirety;
line 50, claim 32 begin a new paragraph with "pharmaceutically".

UNITED STATES PATENT AND TRADEMARK OFFICE
CERTIFICATE OF CORRECTION

PATENT NO.         : 6,452,044 B2
APPLICATION NO. : 09/866758
DATED                 : September 17, 2002
INVENTOR(S)       : Paul F. Jackson et al.

It is certified that error appears in the above-identified patent and that said Letters Patent is hereby corrected as shown below:

Col. 59, line 21, claim 36 begin a new paragraph with "5-[[(1".

Col. 60, line 1, claim 37 change "NHP(O)" to --NH(P(O)--;
        line 22, claim 37 change "NHP(O)" to --NH(P(O)--;
        line 24, claim 37 change "N(C=O)-CH$_2$" to --NR$_5$(C=O)-(CR$_1$R$_2$)--.

Col. 61, line 4, claim 38 change "NHP(O)" to --NH(P(O)--.

Signed and Sealed this

Third Day of February, 2009

JOHN DOLL
*Acting Director of the United States Patent and Trademark Office*